US009096834B2

(12) United States Patent
Seshadri et al.

(10) Patent No.: US 9,096,834 B2
(45) Date of Patent: Aug. 4, 2015

(54) RECOMBINANT MICROORGANISMS COMPRISING THIOESTERASE AND LYSOPHOSPHATIDIC ACID ACYLTRANSFERASE GENES FOR FATTY ACID PRODUCTION

(75) Inventors: Rekha Seshadri, San Diego, CA (US); Jennie Lau Kit, Encinitas, CA (US); Nicholas Bauman, San Diego, CA (US); Robert Christopher Brown, San Diego, CA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 13/404,717

(22) Filed: Feb. 24, 2012

(65) Prior Publication Data
US 2013/0224810 A1 Aug. 29, 2013

(51) Int. Cl.
C12P 7/64 (2006.01)
C12N 1/20 (2006.01)
C12N 1/00 (2006.01)
C12N 1/12 (2006.01)
C12N 9/16 (2006.01)
C12N 9/10 (2006.01)

(52) U.S. Cl.
CPC ............... *C12N 9/1029* (2013.01); *C12N 9/16* (2013.01); *C12P 7/6409* (2013.01); *C12Y 203/01051* (2013.01)

(58) Field of Classification Search
None
See application file for complete search history.

(56) References Cited

U.S. PATENT DOCUMENTS

| | | | |
|---|---|---|---|
| 5,447,858 A | 9/1995 | Key et al. | 435/172.3 |
| 5,455,167 A | 10/1995 | Voelker et al. | 435/172.3 |
| 5,464,758 A | 11/1995 | Gossen et al. | 435/69.1 |
| 5,563,058 A | 10/1996 | Davies et al. | 435/193 |
| 5,639,952 A | 6/1997 | Quail et al. | 800/205 |
| 5,654,495 A | 8/1997 | Voelker et al. | 800/250 |
| 5,661,017 A | 8/1997 | Dunahay et al. | 435/172.3 |
| 5,689,044 A | 11/1997 | Ryals et al. | 800/205 |
| 5,750,385 A | 5/1998 | Shewmaker et al. | 435/172.3 |
| 5,814,618 A | 9/1998 | Bujard et al. | 514/44 |
| 5,824,858 A | 10/1998 | Davies et al. | 800/205 |
| 5,851,796 A | 12/1998 | Schatz | 435/69.1 |
| 5,910,630 A | 6/1999 | Davies et al. | 800/295 |
| 5,968,791 A | 10/1999 | Davies et al. | 435/134 |
| 6,051,755 A | 4/2000 | Zou et al. | 800/281 |
| 6,093,568 A | 7/2000 | Davies et al. | 435/419 |
| 6,143,538 A | 11/2000 | Somerville et al. | 435/189 |
| 6,379,945 B1 | 4/2002 | Jepson et al. | 435/243 |
| 6,410,828 B1 | 6/2002 | Armstrong et al. | 800/287 |
| 7,118,896 B2 | 10/2006 | Kalscheuer et al. | 435/134 |
| 7,135,290 B2 | 11/2006 | Dillon | 435/6 |
| 7,229,815 B2 | 6/2007 | Rajaskharan | 435/195 |
| 7,294,506 B2 | 11/2007 | Daniell et al. | 435/320.1 |
| 7,524,658 B2 | 4/2009 | Damude et al. | 435/134 |
| 7,537,920 B2 | 5/2009 | Renz et al. | 435/194 |
| 7,608,443 B2 | 10/2009 | Kinney et al. | 435/193 |
| 7,871,804 B2 | 1/2011 | Cirpus et al. | 435/193 |
| 8,048,654 B2 | 11/2011 | Berry et al. | 435/134 |
| 2006/0094088 A1 | 5/2006 | Picataggio et al. | 435/134 |
| 2006/0174376 A1* | 8/2006 | Renz et al. | 800/281 |
| 2007/0184538 A1 | 8/2007 | Damude et al. | 435/134 |
| 2009/0209774 A1 | 8/2009 | Renz et al. | 554/20 |
| 2009/0271892 A1 | 10/2009 | Thomasset et al. | 800/281 |
| 2009/0298143 A1 | 12/2009 | Roessler et al. | 435/134 |
| 2010/0105963 A1 | 4/2010 | Hu | 568/840 |
| 2010/0317882 A1 | 12/2010 | Yadav et al. | 554/224 |
| 2011/0020883 A1 | 1/2011 | Roessler et al. | 435/134 |
| 2011/0023185 A1 | 1/2011 | Renz et al. | 800/281 |
| 2011/0250659 A1 | 10/2011 | Roberts et al. | 435/134 |
| 2011/0321195 A1 | 12/2011 | Taylor et al. | 800/281 |
| 2012/0060242 A1 | 3/2012 | Senger et al. | 800/298 |

FOREIGN PATENT DOCUMENTS

| | | |
|---|---|---|
| WO | WO 00/62601 | 10/2000 |
| WO | WO 03/091413 | 11/2003 |
| WO | WO 2005/005643 | 1/2005 |
| WO | WO 2006/052807 | 5/2006 |
| WO | WO 2007/133558 | 11/2007 |
| WO | WO 2007/141257 | 12/2007 |
| WO | WO 2008/157827 | 12/2008 |
| WO | WO 2009/076559 | 6/2009 |
| WO | WO 2009/140696 | 11/2009 |
| WO | WO 2010/042664 | 4/2010 |
| WO | WO 2010/075483 | 7/2010 |
| WO | WO 2010/088426 | 8/2010 |
| WO | WO 2010/135624 | 11/2010 |
| WO | WO 2011/066137 | 6/2011 |

OTHER PUBLICATIONS

UniProtKB Accession P73054, Jan. 2011, 1 page.*
Lu et al., "A perspective: Photosynthetic production of fatty acid-based biofuels in genetically engineered cyanobacteria", Biotechnol. Advances 28:742-746, 2010.*
Liu et al., PNAS 108:6905-6908, 2011.*
Lu, X., Biotechnol. Adv. 28:742-746, 2010.*
Han, M., et al. (2008), "Proteome-level responses of *Escherichia coli* to long-chain fatty acids and use of fatty acid inducible promoter in protein production", *Journal of Biomedicine and Biotechnology*, 2008:735101, doi: 10.1155/2008/735101.

(Continued)

*Primary Examiner* — David J Steadman
(74) *Attorney, Agent, or Firm* — Harness, Dickey & Pierce, P.L.C.

(57) ABSTRACT

The present invention provides for the improved production of fatty acid products in a recombinant microorganism or host cell engineered to express a non-native gene encoding a thioesterase and a non-native gene encoding a lysophosphatidic acid acyltransferase (LPAAT), in which the LPAAT is overexpressed in the recombinant microorganism compared to an otherwise identical microorganism that does not include the non-native LPAAT gene. The invention also provides methods of producing fatty acid products using such recombinant microorganisms.

32 Claims, 6 Drawing Sheets

(56) References Cited

OTHER PUBLICATIONS

Quintana, N., et al. (2011), "Renewable energy from cyanobacteria: energy production optimization by metabolic pathway engineering", *Appl Microbiol Biotechnol*, 91: 471-490.

Abe, J., et al. (2008), "Expression of exogenous genes under the control of endogenous HSP70 and CAB promoters in the closterium peracerosum-strigosum-littorale complex", *Plant Cell Physiol*, 49(4): 625-632.

Altschul, S., et al. (1997), "Gapped BLAST and PSI-BLAST: a new generation of protein database search programs", *Nucleic Acids Research*, 25(17): 3389-3402.

Athenstaedt, K., et al. (1999), "Phosphatidic acid, a key intermediate in lipid metabolism", *Eur. J. Biochem*, 266: 1-16.

Bateman, A., et al. (2000), "The pfam protein families database", *Nucleic Acids Research*, 28(1):263-266.

Bateman, A., et al. (2004), "The pfam protein families database", *Nucleic Acids Research*, 32: Database Issue: D138-D141.

Bourgis, F., et al. (1999), "A plastidial lysophosphatidic acid acyltransferase from oilseed rape[1]", *Plant Physiology*, 120: 913-921.

Brown, A., et al. (1995), "Identification of a cDNA that encodes a 1-acyl-sn-glycerol-3-phosphate acyltransferase from *Limnanthes douglasii*", *Plant Molecular Biology*, 29: 267-278.

Buikema, W., et al. (2000), "Expression of the anabaena hetR gene from a copper-regulated promoter leads to heterocyst differentiation under repressing conditions", *Proc. Natl. Acad. Sciences USA* 98(5): 2729-2734.

Finn, R., et al. (2006), "Pfam: clans, web tools and services", *Nucleic Acids Research*, 34: Database Issue 34:D247-D251.

Finn, R., et al. (2010), "The pham protein families database", *Nucleic Acids Research*, 38: Database Issue 38:D211-D222.

Ghosh, A., et al. (2009), "At4g24160, a soluble acyl-coenzyme a-dependent lysophosphatidic acid acyltransferase", *Plant Physiology*, 151: 869-881.

Hallmann, A., et al. (1997), "Gene replacement by homologous recombination in the multicellular green alga volvox carteri", *Proc. Natl. Acad. Sci USA*, 94:7469-7474.

Handke, P., et al. (2011), "Application and engineering of fatty acid biosynthesis in *Escherichia coli* for advanced fuels and chemicals", *Metabolic Engineering*: 13: 28-37.

Henikoff, S., et al. (1992), "Amino acid substitution matrices from protein blocks", *Proc. Natl. Acad. Sci USA*, 89:10915-10919.

International Search Report for PCT/US12/26566 dated Jun. 18, 2012.

Iwai, M., et al. (2004), "Improved genetic transformation of the thermophilic cyanobacterium, thermosynechoccus elongates BP-1", *Plant Cell Physiol*. 45(2):171-175.

Kaczmarzyk, D., et al. (2010), "Fatty acid activation in cyanobacteria mediated by acyl-acyl carrier protein synthetase enables fatty acid recycling", *Plant Physiology*, 152: 1598-1610.

Karlin, S., et al., (1990), "Methods for assessing the statistical significance of molecular sequence features by using general scoring schemes", *Proc. Natl. Acad. Sci. USA*, 87: 2264-2268.

Kim, H., et al. (2004), "Plastid lysophosphatidyl acyltransferase is essential for embryo development in arabidopsis" *Plant Physiology*, 134: 1206-1216.

Kim, H., et al. (2005), "Ubiquitous and endoplasmic reticulum-located lysophosphatidyl acyltransferase, LPAT2, is essential for female but not male gametophyte development in arabidopsis" *The Plant Cell*. 17: 1073-1089.

Kindle, K., et al. (1989), "Stable nuclear transformation of chlamydomonas using the *Chlamydomonas* gene for nitrate reductase", *The Journal of Cell Biology*, 109 (6, Part 1), 2589-2601.

Knutzon, D., et al. (1995), "Cloning of a coconut endosperm cDNA encoding a 1-Acyl-sn-glycerol-3-phosphate acyltransferase that accepts medium-chain-length substrates" *Plant Physiol*. 109: 999-1006.

Lassner, M., et al. (1995), "Lysophosphatidic acid acyltransferase from meadowfoam mediates insertion of erucic acid at the sn-2 position of triacylglycerol in transgenic rapeseed oil", *Plant Physiol*. 109: 1389-1394.

Liu, X., et al. (2009), "Nickel-inducible lysis system in *Synechocystis* sp. PCC 6803", *Proc. Natl. Acad. Sciences USA* 106: 21550-21554.

Maisonneuve, S., et al. (2010), "Expression of rapeseed microsomal lysophosphatidic acid acyltransferase isozymes enhances seed oil content in arabidopsis[1]", *Plant Physiology*, 152: 670-684.

Méndez-Alvarez, S., et al. (1994), "Transformation of chlorobium limicola by a plasmid that confers the ability to utilize thiosulfate" *Journal of Bacteriology*,176(23):7395-7397.

No, D., et al. (1996), "Ecdysone-inducible gene expression in mammalian cells and transgenic mice", *Proc. Natl. Acad. Sci USA*, 93: 3346-3351.

Ohnuma M., et al. (2008), "Polyethylene glycol (PEG)-mediated transient gene expression in a red alga, cyanidioschyzon merolae 10D", *Plant Cell Physiol*. 49(1):117-120.

Okazaki, K., et al. (2006), The significance of C16 fatty acids in the sn-2 Positions of glycerolipids in the photosynthetic growth of *Synechocystis* sp. PCC6803, *Plant Physiology*, 141: 546-556.

Perrone, C., et al. (1998), "The chlamydomonas IDA7 locus encodes a 140 kDa dynein intermediate chain required to assemble the I1 inner arm complex", *Molecular biology of the Cell*, 9:3351-3365.

Quinn, J., et al. (2003), "Copper response element and crrl-dependent $Ni^2$—responsive promoter for induced, reversible gene expression in *Chlamydomonas reinhardtii*", *Eukaryotic Cell*, 2(5): 995-1002.

Rajasekharan, R., et al., "Fatty acid biosynthesis and regulation in plants", *Plant Developmental Biology*, 6: 105-115, 2010.

Ramesh, V., et al. (2004), "A simple method for chloroplast transformation in *Chlamydomonas reinhardtii*" Methods in Molecular Biology, 274:301-307.

Ravindran, C., et al. (2006), "Electroporation as a tool to transfer the plasmid pRL489 in *Oscillatoria* MKU 277" *Journal of Microbiological Methods*, 66:174-176.

Schroda, M., et al. (2000), "The HSP70A promoter as a tool for improved expression of transgenes in *Chlamydomonas*", *The plant journal* 21(2):121-131.

Shindou, H., et al. (2009), "Acyl-coa:lysophospholipid acyltransferases", *Journal of Biological Chemistry*, 284(1): 1-5.

Shui, G., et al. (2010), "Characterization of substrate preference for Slc1p and Cst26p in *Saccharomyces cerevisiae* using lipidomic approaches and an LPAAT activity assay", *PLoS One*, 5(8): e11956.

Sonnhammer, E., et al. (1998), "Pfam: multiple sequence alignments and HMM-profiles of protein domains" *Nucleic Acids Research* 26(1):320-322.

Steinbrenner, J., et al. (2006), "Transformation of the Green Alga *Haematococcus pluvialis* with a phytoene Desaturase for accelerated astaxanthin biosynthesis" *Applied and Environmental Microbiology* 72(12):7477-7484.

Stemmer, W. (1994), "DNA shuffling by random fragmentation and reassembly: In vitro recombination for molecular evolution", *Proc. Natl. Acad. Sciences USA*, 91: 10747-10751.

Tan, C., et al. (2005), "Establishment of a micro-particle bombardment transformation system for *Dunaliella saline*", *The Journal of Microbiology* 43:361-365.

Wiberg, E., et al. (2000), "The distribution of caprylate, caprate and laurate in lipids from developing and mature seeds of transgenic *Brassica napus* L.", *Planta* 212: 33-40.

Weier, D., et al. (2005), "Characterisation of acyltransferases from *Synechocystis* sp. PCC6803", *Biochem. Biophys. Res. Commun*, 334(4): 1127-1134.

Yu, B., et al. (2004), "Loss of plastidic lysophosphatidic acid acyltransferase causes Embryo-Lethality in *Arabidopsis*" *Plant Cell Physiol*., 45(5): 503-510.

Zhang, Y., et al. (2008), "Acyltransferases in bacterial glycerophospholipid synthesis", *Journal of Lipid Research*, 49: 1867.

Zheng, Z., et al. (2003), "Arabidopsis AtGPAT1, a Member of the membrane-bound glycerol-3-phosphate acyltransferase gene family, is essential for tapetum differentiation and male fertility", 15: 1872-1887.

Zou, J., et al. (1997), "Modification of seed oil content and acyl composition in the Brassicaceae by expression of a yeast sn-2", *The Plant Cell*, 9: 909-923.

(56) References Cited

OTHER PUBLICATIONS

Sun, Y., et al. (2006), "Functional complementation of a nitrate reductase defective mutant of a green alga dunaliella viridis by introducing the nitrate reductase gene", *Gene* 377:140-149.

Knutzon, D.S., et al. Lysophosphatidic Acid Acyltransferase from Coconut Endosperm Mediates the Insertion of Laurate at the *sn*-2 Position of Triacylglycerols in Lauric Rapeseed Oil and Can Increase Total Laurate Levels, *Plant Physiology*, 1999, vol. 120, pp. 739-746.

Thelen, J.J. & J.B. Ohlrogge Metabolic Engineering of Fatty Acid Biosynthesis in Plants, *Metabolic Engineering*, 2002, vol. 4, pp. 12-21.

International Preliminary Report on Patentability dated Aug. 26, 2014 issued in PCT Patent Application No. PCT/US2012/026566.

\* cited by examiner

| Strain | C8:0 | C10:0 | C12:0 | C14:0 | C16:0 | C16:1 cis9 | C18:0 | C18:1 cis9 | C18:2 cis9,12 | C18:3 cis6,9,12 | C18:3 cis9,12,15 |
|---|---|---|---|---|---|---|---|---|---|---|---|
| Control 1A Rep 1 | 1.37 | 0.82 | 22.97 | 75.88 | 85.21 | 2.31 | 16.63 | 16.15 | 5.77 | 4.57 | 3.90 |
| Control 1A Rep 2 | 0.90 | 0.75 | 23.61 | 78.32 | 86.03 | 3.71 | 16.67 | 20.28 | 6.82 | 4.32 | 3.80 |
| Control 1A Rep 3 | 1.13 | 0.62 | 22.28 | 76.91 | 81.96 | 2.51 | 15.45 | 16.56 | 6.69 | 4.23 | 3.28 |
| sll1752 Rep 1 | 0.53 | 0.00 | 0.64 | 1.77 | 13.46 | 1.40 | 14.12 | 16.45 | 4.87 | 1.33 | 3.22 |
| sll1752 Rep 2 | 0.46 | 0.00 | 0.00 | 1.28 | 13.18 | 1.62 | 14.34 | 16.74 | 4.42 | 0.00 | 3.19 |
| sll1752 | 0.68 | 0.00 | 0.00 | 1.93 | 13.71 | 1.45 | 16.29 | 18.22 | 4.71 | 1.58 | 3.00 |
| AASKO Rep 1 | 0.41 | 0.00 | 0.00 | 1.72 | 14.43 | 2.02 | 14.27 | 18.23 | 5.75 | 3.08 | 3.16 |
| AASKO Rep 2 | 0.79 | 0.00 | 0.00 | 1.38 | 14.90 | 2.07 | 13.42 | 17.75 | 5.77 | 2.81 | 3.24 |
| AASKO Rep 3 | 0.62 | 0.00 | 0.00 | 1.41 | 15.21 | 2.64 | 13.37 | 18.47 | 4.92 | 2.78 | 3.43 |
| 1A/sll1752 Clone 3, Rep 1 | 1.10 | 0.85 | 28.51 | 112.56 | 155.83 | 3.19 | 30.77 | 22.35 | 13.17 | 5.57 | 3.35 |
| 1A/sll1752 Clone 3, Rep 2 | 0.93 | 0.76 | 30.64 | 111.08 | 159.53 | 3.98 | 31.21 | 21.88 | 12.38 | 5.80 | 3.22 |
| 1A/sll1752 Clone 3, Rep 3 | 0.97 | 0.76 | 31.48 | 114.99 | 156.71 | 3.23 | 29.84 | 22.48 | 12.74 | 4.98 | 3.66 |
| 1A/sll1752 Clone 5, Rep 1 | 1.05 | 0.77 | 29.86 | 111.62 | 155.21 | 2.90 | 30.53 | 21.05 | 12.36 | 5.69 | 4.04 |
| 1A/sll1752 Clone 5, Rep 2 | 1.04 | 0.60 | 29.26 | 104.85 | 150.17 | 2.40 | 30.17 | 20.72 | 12.05 | 5.27 | 3.39 |
| 1A/sll1752 Clone 5, Rep 3 | 0.98 | 0.88 | 29.08 | 109.42 | 154.44 | 2.58 | 31.04 | 22.16 | 12.59 | 6.10 | 3.87 |
| 1A/sll1752 Clone 6, Rep 1 | 0.91 | 0.78 | 31.26 | 108.22 | 145.40 | 2.82 | 28.43 | 20.77 | 12.76 | 6.40 | 3.21 |
| 1A/sll1752 Clone 6, Rep 2 | 1.21 | 1.07 | 30.79 | 113.20 | 160.87 | 2.84 | 32.69 | 21.68 | 12.60 | 5.81 | 4.06 |
| 1A/sll1752 Clone 6, Rep 3 | 1.08 | 0.71 | 32.38 | 117.78 | 159.10 | 2.94 | 32.07 | 21.88 | 12.81 | 5.69 | 4.40 |
| sll1752/AASKO Rep 1 | 0.59 | 0.42 | 0.80 | 2.20 | 17.74 | 3.13 | 8.25 | 16.86 | 8.10 | 4.29 | 3.05 |
| sll1752/AASKORep 2 | 0.56 | 0.00 | 0.78 | 2.07 | 19.08 | 3.23 | 10.58 | 20.58 | 9.04 | 5.82 | 2.83 |
| sll1752/AASKO Rep 3 | 0.57 | 0.41 | 0.77 | 1.79 | 17.98 | 3.33 | 9.88 | 19.36 | 8.17 | 5.25 | 3.52 |

RECOMBINANT MICROORGANISMS COMPRISING THIOESTERASE AND LYSOPHOSPHATIDIC ACID ACYLTRANSFERASE GENES FOR FATTY ACID PRODUCTION

REFERENCE TO A SEQUENCE LISTING

This application contains references to amino acid sequences and/or nucleic acid sequences which have been submitted concurrently herewith as the sequence listing text file "61099863_1.txt", file size 127 KiloBytes (KB), created on May 10, 2013. The aforementioned sequence listing is hereby incorporated by reference in its entirety pursuant to 37 C.F.R. §1.52(e)(5).

FIELD OF THE INVENTION

The present invention relates to the fields of bioengineering, metabolic biochemistry, and molecular biology. In particular, the invention relates to the production of fatty acid products in a recombinant microorganism or host cell engineered to reduce or minimize feedback inhibition of fatty acid synthesis enzymes and to methods of producing fatty acid products using such recombinant microorganisms or host cells.

BACKGROUND OF THE INVENTION

Producing renewable sources for a variety of fuels and chemicals is of great importance to a world with increasing demand for such products. While petroleum is a product of decayed plant and other matter that has been incubated beneath the earth's surface for millions of years, some efforts today focus on the direct use of plants and other organisms to generate, e.g., lipids, which can include fatty acids and derivatives thereof, for use in the fuel and chemical industries. Fatty acids are composed of long alkyl chains, similar to petroleum, and are a primary metabolite used by cells for both chemical and energy storage functions. Improving the scalability, controllability, and cost-effectiveness of producing fatty acids and fatty acid derivatives (collectively "fatty acid products") would be beneficial to the development of renewable energy and chemical sources.

Fatty acid synthesis in a cell is a repeating cycle where malonyl-acyl carrier protein (malonyl-ACP) is condensed with a carbon substrate to form a growing chain of acyl-ACP. Fatty acid production by engineered cyanobacteria has been described in U.S. Appl. Pub. No. 2009/0298143, which discloses introducing a non-native gene encoding a fatty-acyl-ACP thioesterase to release fatty acids from ACP. However, as with many cellular processes, feedback inhibition by intermediates and/or various end-products may limit production of fatty acids. For example, feedback inhibition of key fatty acid synthesis enzymes, such as ACCase, FabH, and FabI, is mediated by medium- to long-chain acyl-ACPs. See Handke et al., Metabolic Eng. 13:28-37 (2011); FIG. 1 (dashed line).

SUMMARY OF THE INVENTION

The present invention describes additional genetic modifications for improving fatty acid product yields in a microorganism or host cell engineered to express a non-native gene encoding a thioesterase. Such modifications include expression of an additional non-native gene encoding lysophosphatidic acid acyltransferase (LPAAT), which uses acyl-ACP or acyl-CoA substrates to acylate the sn-2 hydroxyl group of lysophosphatidic acid to form phosphatidic acid, a precursor of membrane lipids. The LPAAT preferably has a different acyl chain length substrate preference than the acyl chain length substrate preference of the thioesterase produced by expression of a non-native gene by the recombinant microorganism. Additional modifications of the host microorganism can optionally include attenuation of an acyl-ACP synthetase gene or an acyl-CoA synthetase gene, which participate in recycling and degradation, respectively, of fatty acids, and/or overexpression of one or more polypeptides having lipolytic activity (e.g., lipases) that can release fatty acids from lipids (see e.g., FIG. 1).

In one aspect the invention provides a recombinant microorganism that includes a non-native thioesterase gene, in which the recombinant microorganism further includes a non-native nucleic acid molecule that includes a sequence encoding a lysophosphatidic acid acyltransferase (LPAAT), in which the microorganism produces a fatty acid product. A fatty acid product can be, for example, a free fatty acid, a fatty aldehyde, a fatty alcohol, a fatty acid ester, a wax ester, an alkane, or an alkene. The thioesterase gene can be independently synthesized using synthetic genomic techniques, or alternatively derived from the same or a different species with respect to the host microorganism, and can encode an acyl-ACP thioesterase, an acyl-CoA thioesterase, or a 4-hydroxybenzoyl thioesterase. The thioesterase can be, for example, a thioesterase derived from a prokaryotic species or a plant species. Alternatively or in addition, a non-native thioesterase gene expressed by the host microorganism can be an endogenous thioesterase gene that is operably linked to a heterologous promoter. For example, the thioesterase gene may be an endogenous thioesterase gene, and a heterologous promoter can be introduced into the microorganism to regulate expression of the endogenous thioesterase gene.

The recombinant microorganism that includes a non-native thioesterase gene further includes a non-native nucleic acid molecule that includes a sequence encoding an LPAAT, where the LPAAT-encoding sequence can be homologous (originating from the same species) or heterologous (originating from a different species) with respect to the host microorganism. For example, a non-native LPAAT gene from the same or a different species, preferably operably linked to a heterologous promoter, can be introduced into the host microorganism, or alternatively, a homologous or heterologous LPAAT gene can be introduced into the host microorganism such that the LPAAT gene recombines into the host genome and becomes operably linked to a promoter that is endogenous to the host. Further alternatively, a recombinant microorganism that includes a non-native LPAAT gene can comprise an endogenous LPAAT gene residing in the genome of the host microorganism operably linked to a heterologous promoter introduced into the microorganism and integrated into the genome, for example, by homologous recombination. In further examples, a non-native nucleic acid molecule that includes an LPAAT gene in a microorganism provided herein can encode an LPAAT derived from a prokaryotic or eukaryotic LPAAT (e.g., an LPAAT derived from a higher plant, bryophyte, algal, cyanobacterial, bacterial, fungal, or heterokont (stramenopile) LPAAT, or derived from an animal LPAAT, e.g., a mammalian or insect LPAAT), where a eukaryotic LPAAT gene can encode a plastidal, mitochondrial, or microsomal LPAAT or an LPAAT derived from the sequence of a plastidal, mitochondrial, or microsomal LPAAT.

The recombinant microorganism can comprise at least one non-native LPAAT gene and can further comprise at least one non-native thioesterase gene that can cleave an acyl thioester substrate, in which the LPAAT and the thioesterase preferably have different acyl chain length substrate specificities. For example, the recombinant microorganism can include a non-native nucleic acid molecule encoding an LPAAT that has a substrate preference for one or more long chain acyl substrates (e.g., C16 and/or C18 acyl-ACP or acyl-CoA) and a non-native gene encoding a thioesterase that has a substrate preference for one or more medium chain acyl substrates (e.g., C8, C10, C12, and/or C14 acyl-ACP substrates). Alternatively, the recombinant microorganism can include a non-native nucleic acid molecule encoding an LPAAT that has a substrate preference for one or more medium chain acyl substrates (e.g., C8, C10, C12, and/or C14 acyl-ACP substrates) and a non-native gene encoding a thioesterase that has a substrate preference for one or more long chain acyl substrates (e.g., C16 and/or C18 acyl-ACP or acyl-CoA). In another example, the recombinant microorganism can include a non-native gene encoding an LPAAT that has a substrate preference for a C16 acyl substrate (e.g., C16 acyl-ACP and/or C16 acyl-CoA) and a non-native gene encoding a thioesterase that has a substrate preference for one or more of a C8, C10, C12, or C14 acyl substrate (e.g., C8, C10, C12, and/or C14 acyl-ACP). Alternatively, the recombinant microorganism can include a non-native gene encoding an LPAAT that has a substrate preference for C18 acyl substrates (e.g., C18 acyl-ACP and/or C18 acyl-CoA) and a non-native gene encoding a thioesterase that has a substrate preference for one or more of a C8, C10, C12, C14, or C16 acyl substrate (e.g., C8, C10, C12, C14, and/or C16 acyl-ACP). In further non-limiting examples, a recombinant microorganism can include a non-native gene encoding an LPAAT that has a substrate preference for a C18 acyl substrate and a non-native gene encoding a thioesterase that has a substrate preference for a C16 acyl substrate; a recombinant microorganism can include a non-native gene encoding an LPAAT that has a substrate preference for a C18 acyl substrate and a non-native gene encoding a thioesterase gene that has a substrate preference for C14 and C16 acyl substrates; or a recombinant microorganism can include a non-native gene encoding an LPAAT that has a substrate preference for a C18 acyl substrate and a non-native gene encoding a thioesterase that has a substrate preference for C12, C14, and C16 acyl substrates. In further examples, a microorganism can include a non-native gene encoding an LPAAT that has a substrate preference for a C16 acyl substrate and a non-native gene encoding a thioesterase that has a substrate preference for a C14 acyl substrate; a microorganism can include a non-native gene encoding an LPAAT that has a substrate preference for a C16 acyl substrate and a non-native gene encoding a thioesterase that has a substrate preference for a C12 acyl substrate, and a microorganism can include a non-native gene encoding an LPAAT that has a substrate preference for a C16 acyl substrate and a non-native gene encoding a thioesterase that has a substrate preference for C12 and C14 acyl substrates.

A recombinant microorganism can include a non-native nucleic acid molecule that includes a nucleic acid sequence that encodes an LPAAT that is independently synthesized using synthetic genomic techniques, or alternatively derived from any of a variety of organisms including, for example, animals, fungi, heterokonts, plants, algae, and bacteria, including cyanobacteria. For example, a recombinant microorganism can include a non-native nucleic acid molecule that includes a nucleic acid sequence that encodes an LPAAT derived from a cyanobacterial, bacterial, or plant species, for example, a recombinant microorganism can include a nucleic acid molecule encoding a sequence that encodes an LPAAT that has at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, or SEQ ID NO:26. The LPAAT can be homologous with respect to the host microorganism, for example, the host microorganism can be a cyanobacterial species and the LPAAT produced by expression of the non-native nucleic acid sequence can be an LPAAT derived from the same cyanobacterial species. In an alternative, a host microorganism can be a cyanobacterial species and can include a non-native gene encoding an LPAAT derived from a different cyanobacterial species or from a non-cyanobacterial species.

Additionally to any of the foregoing, a recombinant microorganism that produces a fatty acid product as disclosed herein can include a recombinant nucleic acid molecule that includes a sequence that encodes an LPAAT, in which the LPAAT-encoding sequence is operably linked to a heterologous promoter. The heterologous promoter can be a regulatable promoter, and can optionally be an inducible promoter. For example, the promoter can be induced by light, temperature, or the addition or removal of a compound to the growth media, such as for example, a sugar or sugar analogue, a hormone, a salt, a metal, etc. In particular examples a nucleic acid sequence encoding a thioesterase gene expressed by recombinant microorganism is operably linked to a heterologous promoter that can be, for example, regulatable, and can optionally be inducible. Additionally, an LPAAT-encoding nucleic acid sequence and a thioesterase-encoding nucleic acid sequence can be operably linked to different copies of the same promoter, or to different promoters regulated by the same or different conditions or compound(s). Alternatively, an LPAAT-encoding nucleic acid sequence and a thioesterase-encoding nucleic acid sequence can be operably linked to the same promoter, for example, the LPAAT-encoding nucleic acid sequence and the thioesterase-encoding sequence can be organized as an operon.

Additionally, a recombinant microorganism as provided herein that includes a non-native thioesterase gene and a non-native LPAAT gene can optionally further comprise an attenuated or disrupted acyl-ACP synthetase gene or acyl-CoA synthetase gene. For example, the endogenous acyl-ACP synthetase gene or acyl-CoA synthetase gene can be targeted by antisense RNA, one or more micro RNAs, an siRNA (e.g., generated by a shRNA construct), or one or more ribozymes, to reduce expression of the acyl-ACP synthetase gene or acyl-CoA synthetase gene. Alternatively, the endogenous acyl-ACP synthetase gene or acyl-CoA synthetase gene can be interrupted, truncated, or deleted, for example, by insertional mutagenesis, meganuclease genome modification, and/or homologous recombination.

The recombinant microorganism that includes a non-native LPAAT gene and a non-native thioesterase gene can further optionally include a non-native gene encoding a polypeptide having lipolytic activity, which can be, for example, a lipase, an esterase, a cutinase, or an amidase. Additionally or alternatively, the recombinant microorganism can have an attenuated gene that encodes an acyl-ACP synthetase, an acyl-CoA synthetase, or an acyl-CoA oxidase.

Further additionally or alternatively, a recombinant microorganism that includes a non-native LPAAT gene and a non-native thioesterase gene can further optionally include one or more non-native genes that encode enzymes for producing fatty acid derivatives such as fatty aldehydes, fatty alcohols, fatty acid esters, wax esters, alkanes, and alkenes. Non-limiting examples of such enzymes are aldehyde-forming acyl-ACP reductases, aldehyde-forming acyl-CoA reductases, carboxylic acid reductases, aldehyde-forming fatty acid reductases, alcohol-forming acyl-ACP reductases, alcohol-forming acyl-CoA reductases, acyltransferases, wax synthases, fatty aldehyde decarbonylases, and fatty acid decarboxylases.

The recombinant microorganism that includes a non-native LPAAT gene and a non-native thioesterase gene can produce at least 10% more of a fatty acid product that a microorganism identical in all respects except that it lacks a non-native nucleic acid molecule that comprises a nucleic acid sequence encoding an LPAAT. For example, a recombinant microorganism can produce at least 20%, at least 30%, at least 40%, at least 50%, at least 60%, at least 70%, at least 80%, at least 90%, at least 100%, at least 150%, at least 200%, at least 400%, at least 600%, at least 800%, or at least 1000% more than the amount of the fatty acid product produced by an otherwise identical microorganism not including the non-native nucleic acid molecule that comprises a nucleic acid sequence encoding an LPAAT cultured under identical conditions.

The recombinant microorganism can be any microorganism, for example, a eubacterium, archaebacterium, *cyanobacterium*, microalga, fungus, yeast, or heterokont. The recombinant microorganism can be a photosynthetic microorganism, for example, a microalga or *cyanobacterium*. In some examples a microalga can be a member of the genus *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* or *Volvox*. Alternatively, the recombinant microorganism can be a *cyanobacterium*, for example, of the genus *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus*.

Also provided herein are methods for producing a fatty acid product, where the method includes culturing any of the microorganisms disclosed herein under conditions in which at least one fatty acid product is produced. For example, a recombinant microorganism that includes at least one non-native gene encoding a thioesterase and at least one non-native gene encoding an LPAAT can be cultured in a suitable culture medium such that the non-native genes are expressed to produce at least one free fatty acid or at least one fatty acid derivative. The methods can be used to produce a free fatty acid or a fatty acid derivative such as a fatty aldehyde, a fatty alcohol, a fatty acid ester, a wax ester, or a hydrocarbon. In some examples, the recombinant microorganism produces at least one $C_8$ to $C_{24}$ free fatty acid, such as at least one $C_{12}$ to $C_{18}$ free fatty acid, such as, for example, a $C_{12}$ to $C_{16}$ free fatty acid. Alternatively or in addition, the fatty acid or fatty acid derivative produced using the methods provided herein comprises at least one $C_8$ to $C_{24}$ fatty alcohol or fatty aldehyde, such as at least one $C_{12}$ to $C_{18}$ fatty alcohol or fatty aldehyde, such as a $C_{12}$ to $C_{16}$ fatty alcohol or fatty aldehyde; or at least one wax ester having an A chain of $C_8$ to $C_{24}$ or $C_{12}$ to $C_{18}$, or for example, an A chain of $C_{12}$ to $C_{16}$, and a B chain of $C_8$ to $C_{24}$ or $C_{12}$ to $C_{18}$, or for example, a B chain of $C_{12}$ to $C_{16}$; or at least one $C_{11}$ to $C_{23}$ alkane or alkene, such as a $C_{11}$ to $C_{15}$ alkane or alkene. The method can further include isolating a fatty acid product from the microorganism, the culture medium, or a combination thereof. Additionally, the recombinant microorganism may secrete at least a portion of the fatty acid product into the culture medium, and optionally all or a portion of the secreted product can be isolated from the culture medium.

In various methods, the amount of fatty acid product produced by the recombinant microorganism can be at least 10% greater, at least 20% greater, at least 30% greater, at least 40% greater, at least 50% greater, at least 60% greater, at least 70% greater, at least 80% greater, at least 90% greater, or at least 100% greater than the amount produced by an otherwise identical microorganism lacking the non-native nucleic sequence encoding an LPAAT that is cultured under the same conditions.

Further provided is a fatty acid product made using the methods of the invention. The fatty acid product can be, for example, a fatty acid, a fatty alcohol, a fatty aldehyde, an alkane, an alkene, a fatty acid ester, or a wax ester. The fatty acid product can have at least one carbon chain having a length of $C_7$ to $C_{24}$, and in some preferred embodiments, the fatty acid product includes one or more free fatty acids, fatty aldehydes, fatty alcohols, alkanes, or alkenes having $C_{12}$ to $C_{18}$ chain lengths, for example, chain lengths of $C_{12}$ to $C_{16}$, or one or more fatty acid esters having one or both of an A chain and a B chain of $C_8$ to $C_{24}$, or of $C_{12}$ to $C_{18}$, for example, $C_{12}$ to $C_{16}$. For example, a wax ester produced using the methods provided herein can have an A and a B chain of $C_8$ to $C_{24}$, or of $C_{12}$ to $C_{18}$, or in some examples of $C_{12}$ to $C_{16}$.

BRIEF DESCRIPTION OF THE DRAWINGS

FIG. 6 is a table providing the amounts (μg/mL) of free fatty acids of particular chain lengths and degree of saturation produced by *Synechocystis* sp. PCC 6803 strains comprising the Cc1FatB1 acyl-ACP thioesterase gene (Control 1A), the recombinant sll1752 gene encoding a C18:0 LPAAT (sll1752), an attenuated acyl-ACP synthetase gene (AASKO), three separate clones (Clone 3, Clone 5, Clone 6) containing the Cc1FatB1 acyl-ACP thioesterase gene as well as the recombinant sll1752 gene (1A/sll1752), and the recombinant sll1752 gene in combination with the attenuated acyl-ACP synthetase gene (sll1752/AASKO).

DETAILED DESCRIPTION OF THE INVENTION

Definitions

Figure 1:
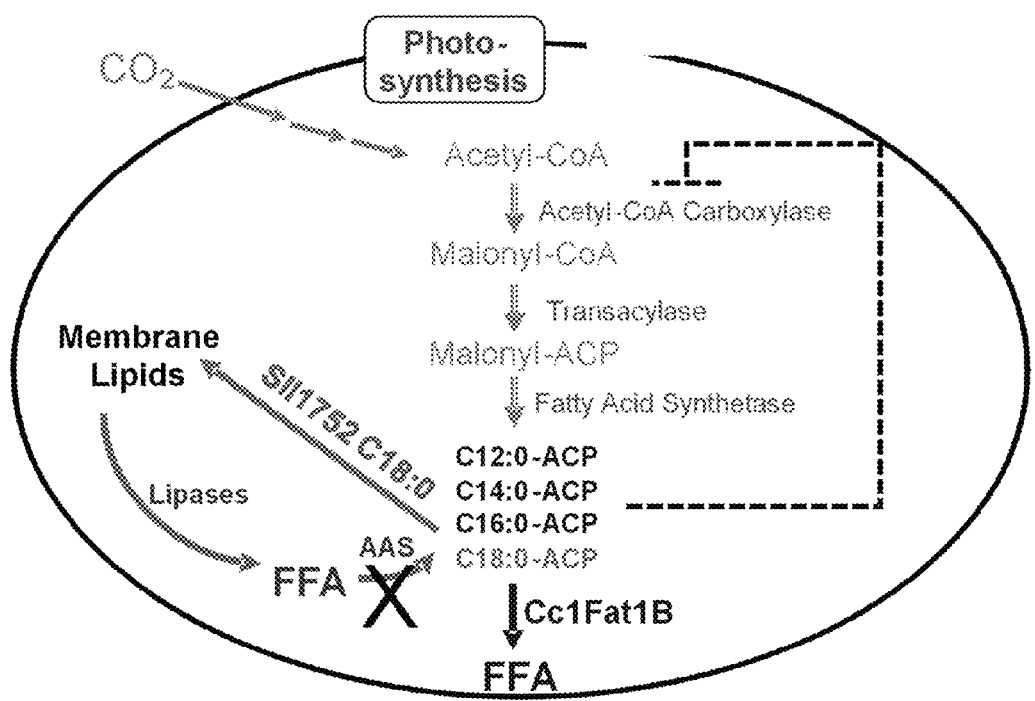
FIG. 1 is a schematic depicting genetic modifications proposed to relieve feedback inhibition of fatty acid biosynthesis by reducing the pool of C18-ACP. Abbreviations are FFA: free fatty acid, AAS: acyl-ACP synthase, Cc1FatB1: *Cuphea carthagenensis* acyl-ACP thioesterase with a C12, C14, and C16 substrate preference, and Sll1752 C18:0: LPAAT of *Synechocystis* sp. 6803 with a C18 acyl substrate preference.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

To facilitate an understanding of the present invention, a number of terms and phrases are defined below.

As used in the present disclosure and claims, the singular forms "a," "an," and "the" include plural forms unless the context clearly dictates otherwise.

Wherever embodiments are described herein with the language "comprising," otherwise analogous embodiments described in terms of "consisting of" and/or "consisting essentially of" are also provided.

The term "and/or" as used in a phrase such as "A and/or B" herein is intended to include "A and B", "A or B", "A", and "B".

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences). Genes may further comprise the regulatory sequences required for their expression. Genes can be obtained from a variety of sources, including cloning from a source of interest or synthesizing from known or predicted sequence information, and may include sequences designed to have desired parameters.

The term "nucleic acid" or "nucleic acid molecule" refers to, e.g., DNA or RNA (e.g., mRNA). The nucleic acid molecules can be double-stranded or single-stranded; single stranded RNA or DNA can be the coding (sense) strand or the non-coding (antisense) strand.

A nucleic acid molecule may be "derived from" an indicated source, which includes the isolation (in whole or in part) of a nucleic acid segment from an indicated source or the purification of a polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can incur one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other molecular biology techniques, or by chemical synthesis. A gene or nucleic acid molecule that is derived from a referenced gene or nucleic acid molecule that encodes a functional RNA or polypeptide can encode a functional RNA or polypeptide having at least 70%, at least 75%, at least 80%, at least 85%, at least 90%, at least 95%, at least 96%, at least 97%, at least 98%, or at least 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, or insertional mutation) or having decreased expression due to alteration of gene regulatory sequences.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule that: 1) has been synthesized or modified in vitro, for example, using chemical or enzymatic techniques (for example, by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering.

When applied to organisms, the term recombinant, engineered, or genetically engineered refers to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. The heterologous or recombinant nucleic acid molecule can be integrated into the recombinant/genetically engineered organism's genome or in other instances are not integrated into the recombinant/genetically engineered organism's genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in both directions off of opposite strands). A promoter may be a constitutive promoter, a repressible promoter, or an inducible promoter. Non-limiting examples of promoters include, for example, the T7 promoter, the cytomegalovirus (CMV) promoter, the SV40 promoter, and the RSV promoter. Examples of inducible promoters include the lac promoter, the pBAD (araA) promoter, the Tet promoter (U.S. Pat. Nos. 5,464,758 and 5,814,618), and the Ecdysone promoter (No et al., Proc. Natl. Acad. Sci. (1996) 93 (8): 3346-3351).

The term "heterologous" when used in reference to a polynucleotide, a gene, a nucleic acid, a polypeptide, or an enzyme refers to a polynucleotide, gene, a nucleic acid, polypeptide, or an enzyme not naturally found in the host organism. When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology.

Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a pre-selected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least 65%, 70%, 75%, 80%, or 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, at least 75, at least 100, at least 125, at least 150 or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

The term "secreted" includes movement of polypeptides or fatty acid products produced by the recombinant microorganisms or methods of the invention to the periplasmic space or extracellular milieu. "Increased secretion" includes secretion in excess of the naturally-occurring amount of secretion, e.g., that is at least 1%, 2%, 3%, 4%, 5%, 6%, 7%, 8%, 9%, or 10%, or at least 20%, 30%, 40%, 50%, 60%, 70%, 80%, 90%, 100%, 200%, 300%, 400%, 500%, 600%, 700%, 800%, 900%, 1000%, or more, as compared to the naturally-occurring level of secretion.

Embodiments of the present invention provide for the "insertion," e.g., the addition, integration, incorporation, or introduction, the activation, or up-regulation of certain nucleic acid molecules or particular polynucleotide sequences, with or without additional regulatory sequences, within microorganisms or host cells in order to affect the activity, such as the expression of an enzyme, of certain nucleic acid molecules or particular polynucleotide sequences. In certain embodiments, a microorganism of interest may be engineered by site directed homologous recombination to insert a particular gene of interest or a promoter that affects the expression of a particular gene or set of genes.

Embodiments of the present invention provide recombinant microorganisms in which the nucleic acid molecules or particular polynucleotide sequences are partially, substantially, or completely deleted, silenced, inactivated, or down-regulated in order to affect the activity for which they encode, such as the expression of an enzyme. Genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination to knockout a particular gene of interest. In still other embodiments, RNAi or antisense DNA (asDNA) may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se/ (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 26.0 (November 2011) based on the UniProt protein database release 15.6, a composite of Swiss-Prot release 57.6 and TrEMBL release 40.6. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) *Nucleic Acids Research* 26, 263-266; Bateman (2004) *Nucleic Acids Research* 32, Database Issue, D138-D141; Finn (2006) *Nucleic Acids Research Database Issue* 34, D247-251; Finn (2010) *Nucleic Acids Research* Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a Pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

An enzyme such as an LPAAT or a thioesterase that acts on acyl thioester substrates (e.g., uses acyl-ACP and/or acyl-CoA substrates) often has activity on substrates of different chain lengths, but can have greater activity on one or more substrates than on others. For example, "substrate preference" refers to the substrate or substrates an enzyme is most active on. Different acyl-ACP thioesterases may have different degrees of chain length specificity, sometimes referred to as the enzyme's "preference" for cleaving a particular length of fatty acid from ACP, and thioesterases are typically most active in cleaving a particular chain length fatty acid while having lesser activity in cleaving one or more other chain length fatty acids. Similarly, an LPAAT can have a substrate preference for one or more acyl substrates, such as acyl-ACP or acyl-CoA substrates of particular carbon chain lengths.

As used herein, a "medium chain length" fatty acid or acyl-ACP is a fatty acid or acyl-ACP having a chain length of from 8-14 carbons.

As used herein, a "long chain length" fatty acid or acyl-ACP is a fatty acid or acyl-ACP having a chain length of greater than 14 carbons.

As used herein, the term "fatty acid product" includes free fatty acids; mono-, di- or triglycerides; fatty aldehydes; a fatty alcohols; fatty acid esters (including, but not limited to, wax esters); and hydrocarbons (including, but not limited to, alkanes and alkenes).

Metabolic Pathways for Producing Fatty Acids

The fatty acid biosynthesis pathway is highly conserved in prokaryotes and in the chloroplasts of eukaryotic algae and higher plants. The fatty acid biosynthesis pathway starts from the central metabolite acetyl-CoA. Fatty acid biosynthesis is initiated by the conversion of acetyl-CoA to malonyl-CoA, catalyzed by acetyl-CoA carboxylase (ACCase). Malonyl-CoA is then converted to malonyl-ACP, catalyzed by malonyl-CoA-ACP transacylase (FabD in *E. coli*). Finally, malonyl-ACP is converted to acyl-ACP, catalyzed by the enzyme complex fatty acid synthase (FAS). The fatty acid synthase complex initiates the elongation cycle by first condensing malonyl-ACP with acetyl-ACP, catalyzed by a beta-ketoacyl-ACP synthase III (e.g., FabH of *E. coli*). The β-ketoacyl-ACP (3-ketoacyl-ACP) formed by the FabH reaction is reduced to a β-hydroxyacyl-ACP (3-hydroxyacyl-ACP) by 3-ketoacyl-ACP reductase (e.g. FabG). The β-hydroxyacyl-ACP is then acted on by a β-hydroxyacyl-ACP dehydratase (e.g. FabA, FabZ) to form trans-2-enoyl-ACP, which in turn is reduced by enoyl-ACP reductase (e.g. Fab I, Fab K, FabL) to form the 2 carbon-elongated acyl-ACP product. Subsequent cycles are initiated by a beta-ketoacyl-ACP synthase I or II (e.g., FabB or FabF) catalyzed condensation of malonyl-ACP with acyl-ACP. The cycles of condensation, reduction, dehydration, and reduction are repeated, with each cycle adding two carbons from malonyl-ACP, until the acyl chain is transferred to another molecule (e.g. glycerol 3-phosphate) by a transacylase or cleaved from ACP by a thioesterase, such as FatA or FatB in chloroplasts, to form free fatty acids.

Unlike plant chloroplasts, cyanobacteria do not produce free fatty acids, and unlike *E. coli* and other heterotrophic bacteria, cyanobacteria do not produce acyl-CoA. After fatty acid elongation with the acyl chain covalently bound to acyl carrier protein, acyl transferases of cyanobacteria transfer the acyl chain to a glycerol backbone to produce membrane lipids.

To produce fatty acid derivatives such as fatty alcohols, fatty aldehydes, wax esters, alkanes, or alkenes in microorganisms, it is typically necessary to introduce one or more genes encoding one or more enzymes to convert acyl-thioester intermediates (e.g., acyl-CoA or acyl-ACP) to the desired end product (e.g., an alcohol, aldehyde, alkane, alkene, or wax ester). For example, if fatty aldehydes and/or alkanes are the desired end product, a gene encoding an aldehyde-forming fatty aldehyde reductase (e.g., aldehyde-forming acyl-CoA reductase, 1.2.1.42 or 1.2.1.50; see also U.S. Pat. No. 6,143,538) may be introduced to reduce acyl-CoA to fatty aldehydes; additionally or alternatively, a carboxylic acid reductase gene (see, e.g., WO 2010/135624 and WO 2010/042664) may be introduced to reduce free fatty acids to fatty aldehydes. Further, a gene encoding a fatty alcohol oxidase (e.g., 1.1.3.20) or a fatty alcohol dehydrogenase (e.g., 1.1.1.164) may be introduced to convert fatty alcohols to fatty aldehydes. Fatty aldehydes may be processed further to alkanes with the introduction of a gene encoding a fatty aldehyde decarbonylase (e.g., 4.1.99.5). If fatty alcohols, alkenes and/or wax esters are the desired end product, a gene encoding an alcohol-forming fatty acyl reductase (e.g., alcohol-forming acyl-CoA reductase, 1.2.1.50) may be introduced into the host cell. Further, a fatty aldehyde reductase gene may be introduced to reduce fatty aldehydes to fatty alcohols. Fatty alcohols may be processed further to alkenes with the introduction of one or more genes encoding a fatty alcohol dehydratase. Fatty acid esters, including wax esters, may be formed by introducing genes encoding polypeptides that catalyze condensation of an alcohol with a fatty acyl thioester, such as acyltransferases and wax synthases.

In some embodiments of the invention described above, the conversion of acyl-ACP to fatty alcohol may occur via synthesis of a fatty aldehyde, wherein an acyl reductase (e.g., an aldehyde-forming acyl-CoA reductase or aldehyde-forming acyl-ACP reductase) expressed in the host cell first reduces acyl-ACP to a fatty aldehyde. For example, in certain embodiments, the host cell can be engineered to overexpress an endogenous fatty aldehyde-forming reductase (e.g., by inserting promoter and/or enhancer transcriptional control elements near the fatty aldehyde-forming reductase gene). In other embodiments, the host cell may be engineered to express an exogenous fatty aldehyde-forming reductase.

Lysophosphatidic Acid Acyltransferases

As used herein, the term "lysophosphatidic acid acyltransferase" or "LPAAT", or "1-acyl-sn-glycerol-3-phosphate acyltransferase" or "AGPAT" (encoded by plsC in *E. coli* and other prokaryotes), includes those enzymes capable of converting a lysophosphatidic acid to a phosphatidic acid by transferring an acyl chain from an acyl substrate such as acyl-CoA or acyl-ACP to the sn2 position of lysophosphatidic acid. LPAAT includes those enzymes that correspond to Enzyme Commission Number 2.3.1.51.

LPAAT and the enzyme glycerol-3-phosphate acyltransferase (glycerolphosphate acyltransferase; GPAT; encoded by plsB in *E. coli*) which catalyzes the conversion of glycerol-3-phosphate to lysophosphatidic acid, share canonical acyltransferase signatures such as HXXXXD or NHXXXXD and XXXXXXG, where X is an arbitrary amino acid, separated by 60 to 83 amino acid residues (Okazaki, K., et al. (2006) *Plant Physiol.* 141:546-56). Nucleic acids that encode GPATs and LPAATs having these signature sequences have been identified in many organisms, including *Arabidopsis thaliana* (Zheng et al. (2003) *Plant Cell* 15:1872-87; Kim and Huwang (2004) *Plant Physiol.* 134:1206-16; Yu et al. (2003) *Plant Cell Physiol.* 15:1872-87) and *Synechocystis* sp. PCC6803 (Weier et al. (2005) *Biochem. Biophys. Res. Commun.* 334: 1127-34; Okazaki, K., et al. (2006) *Plant Physiol.* 141:546-56). For example, an endoplasmic reticulum-located (microsomal) LPAAT, which is encoded by the LAT2 gene from *Limnanthes douglasii* or by the LPAT2 gene from *A. thaliana*, have 68 or 69 amino acid residues between the canonical acyltransferase signatures and can use C18 acyl substrates, such as C18:1 CoA, for membrane lipid synthesis (Brown et al. (1995) *Plant Mol. Biol.* 29:267-78; Kim et al. (2005) *Plant Cell* 17:1073-89). Other seed-specific endoplasmic reticulum-located LPAATs may have 63 amino acid residues or approximately 63 amino acid residues between the canonical acyltransferase signatures and may use unusual acyl substrates, e.g., C12:0 or C22:1 acyl substrates which in various plant species are incorporated into seed storage lipids (Brown et al. (1995) *Plant Mol. Biol.* 29:267-78; Knutzon et al. (1995) *Plant Physiol.* 109:999-1006; Lassner et al. (1995) *Plant Physiol.* 109:1389-94).

LPAATs useful in the microorganisms and methods provided herein may have one or more conserved domains found in cyanobacterial LPAAT sll1752 (SEQ ID NO:2), as characterized in the Conserved Domain Database maintained by the National Center for Biotechnology Information (available at ncbi.nlm.nih.gov/Structure/cdd/cdd.shtml), such as but not limited to: cd07992 (Lysophospholipid Acyltransferases (LPLATs) of Glycerophospholipid Biosynthesis: Unknown AAK14816-like), cd07989 (Lysophospholipid Acyltransferases (LPLATs) of Glycerophospholipid Biosynthesis: AGPAT-like), cd06551 (Lysophospholipid acyltransferases (LPLATs) of glycerophospholipid biosynthesis), cd07993 (Lysophospholipid Acyltransferases (LPLATs) of Glycerophospholipid Biosynthesis: GPAT-like), cd07988 (Lysophospholipid Acyltransferases (LPLATs) of Glycerophospholipid Biosynthesis: Unknown ABO13168), cd07987 (Lysophospholipid Acyltransferases (LPLATs) of Glycerophospholipid Biosynthesis: MGAT-like), COG0204: P1sC (1-acyl-sn-glycerol-3-phosphate acyltransferase), TIGR00530: AGP acyltrn (1-acyl-sn-glycerol-3-phosphate acyltransferases), cd07991: LPLAT LPCAT1-like (Lysophospholipid Acyltransferases (LPLATs) of Glycerophospholipid Biosynthesis: LPCAT1-like), cd07990 (Lysophospholipid Acyltransferases (LPLATs) of Glycerophospholipid Biosynthesis: LCLAT1-like), and cd07986 (Lysophospholipid Acyltransferases (LPLATs) of Glycerophospholipid Biosynthesis: Unknown ACT14924).

Because LPAATs are essential to the production of phosphatidic acid in all cellular organisms except archea, LPAATs can be identified from a large variety of species, using, e.g., the canonical acyltransferase sequence signatures described above and/or by bioinformatics to identify conserved domains characteristic of LPAATs, such as, but not limited to, those provided above, as well as by inclusion in Pfam PF01553 ("Acyltransferase"), which has a gathering cut-off of 21.1. LPAAT activity and substrate specificity can be determined using, e.g., an acyltransferase assay as described in Okazaki, K. et al. (2006) *Plant Physiol.* 141:546-56, WO2007141257, or U.S. Pat. No. 5,563,058, each of which is incorporated by reference, in which any of the methods can be adapted to use either acyl-ACP or acyl-CoA as a substrate, or by using any of the methods disclosed herein.

A gene encoding an LPAAT with a particular acyl chain length substrate preference can be expressed in a recombinant microorganism that expresses a non-native thioesterase gene as provided herein to increase the levels of free fatty acids produced by the recombinant host cells or microorganisms. An LPAAT gene can be selected based on the substrate preference of the encoded enzyme in relation to the substrate preference of the thioesterase produced by the recombinant microorganism or host cell. In some aspects of the invention, an LPAAT can be selected that has a different acyl chain length substrate preference than the thioesterase produced by expression of a non-native gene, which can be for example, an acyl-ACP thioesterase, an acyl-CoA thioesterase, or a 4-hydroxybenzoyl thioesterase. In some aspects of the invention, an LPAAT is selected that has a complementary acyl substrate chain length preference with respect to the substrate preference of the thioesterase produced by the recombinant microorganism, where acyl substrates preferred by the LPAAT are not preferred substrates of the thioesterase, and acyl substrates preferred by the thioesterase are not preferred substrates of the LPAAT. For example, in certain aspects an LPAAT is selected that has a medium chain-length acyl substrate preference, e.g., a preference for using a C12 and/or a C14 acyl-ACP or acyl-CoA, and in other aspects, an LPAAT is selected that has a long chain-length acyl-ACP substrate preference, e.g., a preference for using a C16 and/or a C18 acyl-ACP substrate. In certain aspects, an LPAAT is selected that has a medium chain-length acyl-ACP substrate preference and an acyl-ACP thioesterase is selected that has a long chain-length acyl-ACP or acyl-CoA substrate preference. In certain aspects, an LPAAT is selected that has a long chain-length acyl substrate preference and an acyl-ACP thioesterase is selected that has a medium chain-length acyl-ACP substrate preference. The preferred acyl-ACP substrate can have a saturated acyl chain or can have an unsaturated acyl chain.

In some preferred embodiments of the foregoing, the LPAAT encoded by a non-native nucleic acid sequence in the recombinant microorganism has a substrate preference for acyl-ACP or acyl-CoA molecules having longer acyl chain lengths than the acyl substrates preferred by the thioesterase produced by expression of a non-native thioesterase gene in the recombinant microorganism. Without limiting the invention to any particular mechanism, the LPAAT can have a substrate preference for an acyl substrate that has a longer acyl chain than the acyl substrate preferred by the thioesterase produced by the recombinant microorganism, such that during fatty acid biosynthesis, acyl-ACP intermediates are either cleaved by the thioesterase or, if they escape cleavage at the preferred substrate chain length, their acyl chains become further elongated in the fatty acid biosynthesis cycle such that they attain a chain length preferred by the LPAAT. The LPAAT can then act on the acyl-ACP substrate, transferring the acyl chain to a glycerolipid and thereby removing acyl-ACP intermediates that have been elongated beyond the substrate preference of the thioesterase. Such intermediates could otherwise build up in the cell and thereby downregulate fatty acid synthesis. For example, the recombinant microorganism can express an acyl-ACP thioesterase, acyl-CoA thioesterase, or 4-hydroxybenzoyl thioesterase having a medium chain acyl substrate preference (for example, for C8, C10, C12, and/or C14 acyl substrates such as acyl-ACP and/or acyl-CoA) and an LPAAT having a long chain acyl substrate preference (for example, for C16, C18, C20, C22, or C24 acyl substrates such as acyl-ACP and/or acyl-CoA). In some examples, the recombinant microorganism expresses a non-native gene encoding a thioesterase that has a preference for a C12 and/or C14 acyl substrate and expresses a non-native gene encoding an LPAAT that has a preference for one or more C16 and/or C18 acyl substrates. In another example, both the thioesterase and the LPAAT encoded by non-native genes in the recombinant cell can have long chain acyl substrate preferences, where the LPAAT prefers one or more substrates having a longer acyl chain length than the acyl chain length of the substrate(s) preferred by the thioesterase. For example, a recombinant microorganism can express a non-native gene encoding a thioesterase having a C16 acyl substrate preference and a non-native gene encoding an LPAAT having a C18 acyl substrate preference. In further examples, the recombinant microorganism expresses a non-native gene encoding a thioesterase that has a preference for a C12, C14, and/or C16 acyl substrate and expresses a non-native gene encoding an LPAAT that has a preference for a C18 acyl substrate. For example, the recombinant microorganism can express a non-native gene encoding a thioesterase that has a C12 acyl substrate preference or a C14 acyl substrate preference. For example, the recombinant microorganism can express an LPAAT having a C18 acyl substrate preference and can express a non-native gene encoding a thioesterase that has a C16 acyl substrate preference, or the recombinant microorganism can express a non-native gene encoding a thioesterase that has a C14 and C16 acyl substrate preference or a preference for a C12, C14, and C16 acyl substrates.

An LPAAT gene that can be useful in the host cells and methods provided herein can be a prokaryotic or eukaryotic LPAAT gene. A prokaryotic LPAAT gene can be derived from any prokaryotic microorganism, for example, a bacterium or *cyanobacterium*. Prokaryotic LPAATs commonly have a C16 acyl substrate preference, although the invention considers prokaryotic LPAATs having substrate preferences for any acyl chain length, particularly but not exclusively C16 and C18 chain lengths. For example, an LPAAT encoded by a non-native nucleic acid molecule can from a bacterial species such as, for example, *E. coli*, e.g., plsC (SEQ ID NO:16) or the LPAAT of *Marinobacter adhaerens* HP15 (Genbank accession ADP99136, gene identifier 311696263; SEQ ID NO:17) and orthologs in other bacterial species having at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identity to SEQ ID NO:16 or SEQ ID NO:17, or the LPAAT can be derived from a cyanobacterial species, such as the sll1752 LPAAT of *Synechocystis* sp. PCC 6803 and orthologs in other species.

The LPAAT encoded by the sll1752 gene from *Synechocystis* sp. PCC 6803 (GenBank/EMBL accession number NP 440396 or BAA17076; SEQ ID NO:2), orthologs of which are widely conserved in published genomes of cyanobacteria, has been shown to have a preference for C18:0 and C18:1 acyl substrates (Okazaki, K., et al. (2006) *Plant Physiol.* 141:546-56). The LPAAT encoded by the sll1752 gene from *Synechocystis* sp. PCC 6803 has a distance of 64 amino acid residues between the canonical acyltransferase signatures, which is similar to seed-specific LPAATs of higher plants.

Cyanobacterial LPAATs considered to be orthologs of the polypeptide encoded by sll1752 (Genbank Accession NP_440396; gene identifier 16329668; SEQ ID NO:2) of *Synechocystis* include, but are not limited to, the phospholipid/glycerol acyltransferase of *Cyanothece* sp. PCC 8801 (Genbank Accession YP_002372580; gene identifier 218247209; SEQ ID NO:3), the phospholipid/glycerol acyltransferase of *Crocosphaera watsonii* WH 8501 (Genbank Accession ZP_00513647; gene identifier 67920127; SEQ ID NO:4), hypothetical protein CY0110_27159 of *Cyanothece* sp. CCY0110 (Genbank Accession ZP_01731155; gene identifier 126660033; SEQ ID NO:5), the unnamed protein product of *Microcystis aeruginosa* PCC 7806 (Genbank Accession CAO89042; gene identifier 159026728; SEQ ID NO:6), the hypothetical protein a114871 of *Nostoc* sp. PCC 7120 (Genbank Accession NP_488911; gene identifier 17232363; SEQ ID NO:7), the unnamed protein product of *Anabaena variabilis* ATCC 29413 (Genbank Accession YP_322656; gene identifier 75908360; SEQ ID NO:8), the phospholipid/glycerol acyltransferase of '*Nostoc azollae*' 0708 (Genbank Accession YP_003721758; gene identifier 298491581; SEQ ID NO:9), the phospholipid/glycerol acyltransferase of Raphidiopsis brookii D9 (Genbank Accession ZP_06305519; gene identifier 282897518; SEQ ID NO:10), the acyltransferase domain protein of *Microcoleus chthonoplastes* PCC 7420 (Genbank Accession ZP_05026385; gene identifier 254412612; SEQ ID NO:11), the phospholipid/glycerol acyltransferase of *Cylindrospermopsis raciborskii* CS-505 (Genbank Accession ZP_06306989; gene identifier 282899007; SEQ ID NO:12), the conserved hypothetical protein of *Oscillatoria* sp. PCC 6506 (Genbank Accession ZP_07110610; gene identifier 300865867; SEQ ID NO:13), the phospholipid/glycerol acyltransferase of *Nodularia spumigena* CCY9414 (Genbank Accession ZP_01628592; gene identifier 119509444; SEQ ID NO:14), and the phospholipid/glycerol acyltransferase of *Microcoleus vaginatus* FGP-2 (Genbank Accession ZP_08495621; gene identifier 334121556; SEQ ID NO:15). These and other orthologs of sll1752 (SEQ ID NO:2) of *Synechocystis* are considered for use in the microorganisms and methods provided herein. Recombinant microorganisms that include a non-native nucleic acid sequence that encodes an LPAAT and produce at least one free fatty acid or at least one fatty acid derivative can include non-native sequences encoding LPAATs having at least 40%, at least 45%, at least 50%, at least 55%, at least 60%, at least 65%, at least 70%, at least 75%, at least 80%, at least 85%, at least 90%, at least 95%, at least 96%, at least a 97%, at least 98%, at least 99%, or 100% identity to any of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:15, or to LPAATs encoded by other cyanobacterial orthologs of the *Synechocystis* sll1752 gene.

Alternatively or in addition, a recombinant microorganism can include a non-native nucleic acid molecule encoding a eukaryotic LPAAT. A eukaryotic LPAAT can be derived from an animal, fungal, bacterial, plant or algal species. For example, a recombinant microorganism can include a non-native nucleic acid molecule encoding a plant or eukaryotic algal LPAAT and can be, in some examples, an LPAAT that is naturally either associated with a plastid or hypothesized to be associated with a plastid (for example, based on sequence similarities to other plastidal LPAATs). Plastidal LPAATs typically have a C16 acyl substrate preference. Nonlimiting examples of plastidal LPAATs include the polypeptides having GenBank accession numbers ABB47826 (gene identifier 78708851) from *Oryza sativa* (SEQ ID NO:18), XP 003525921; XP_003525921 (gene identifier 356514455) of *Glycine max* (SEQ ID NO:19); AAF73736 (gene identifier 8163563) of *Brassica napus* (SEQ ID NO:20), and NP_194787 (gene identifier 8163563) of *Arabidopsis thaliana* (SEQ ID NO:21). As nonlimiting examples, a non-native gene that can be present in a recombinant microorganism as disclosed herein can encode an LPAAT having at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to any of for example, SEQ ID NO:18, SEQ ID NO:19, SEQ ID NO:20, or SEQ ID NO:21.

A nucleic acid sequence can also encode an LPAAT derived from a eukaryotic species that is either associated with the endoplasmic reticulum (ER) or cytosol or hypothesized to be associated with the ER or cytosol, which may be referred to as a cytoplasmic, cytosolic, or microsomal LPAAT. Many microsomal LPAATs have a C18 acyl substrate preference. For example, a non-native nucleic acid sequence can encode a microsomal LPAAT from a fungus, heterokont, mammal, insect, bryophyte, or higher plant. Illustrative examples of microsomal LPAATs include, without limitation, LPATs having the following GenBank accession numbers: CAA82638 (gene identifier 575960; SEQ ID NO:22) of *Zea mays*, AEE79683 (gene identifier 332646162; SEQ ID NO:23) of *Arabidopsis thaliana*, AEE32642 (gene identifier 332194521; SEQ ID NO:24) of *Arabidopsis thaliana*, CAB09138 (gene identifier 4583544; SEQ ID NO:25) of *Brassica napus*, and AAF20003 (gene identifier 6635840; SEQ ID NO:26) of *Prunus dulcis*. For example, a microorganism as provided herein can include a non-native gene encoding an LPAAT having at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to any of SEQ ID NO:22, SEQ ID NO:23, SEQ ID NO:24, SEQ ID NO:25, or SEQ ID NO:26.

Additional microsomal LPAATs considered for use in the methods and microorganisms include LPAATs with medium chain length preference (e.g., U29657; GI:1098604), or acyl chain length preference of greater than C18 (e.g., AAC49185.1; GI:1209507).

Thioesterases

As used herein, the term "thioesterase" is intended to include hydrolases capable of acting on a thioester bond. Such enzymes can correspond to, e.g., Enzyme Commission Number 3.1.2.2, 3.1.2.14, 3.1.2.18, 3.1.2.19, 3.2.1.20, 3.1.2.22, 3.1.2.23, or 3.1.2.27. A thioesterase expressed in a recombinant microorganism or host cell of the invention can be, for example, an acyl-ACP thioesterase, an acyl-CoA thioesterase, or a hydroxylbenzoyl thioesterase. For example, a recombinant microorganism or host cell can be transformed with a gene encoding an exogenous acyl-ACP thioesterase, such as a gene encoding a polypeptide that when queried against the Pfam database, provides a match with Pfam PF01643 having a bit score of less than or equal to 20.3 (the gathering cut-off for PF01643). The acyl-ACP thioesterase gene can encode an acyl-ACP thioesterase from a higher plant species. Genes encoding acyl-ACP thioesterases derived from higher plants can include, without limitation, genes encoding acyl-ACP thioesterases from *Cuphea* species (e.g. *Cuphea carthagenensis*, *Cuphea wrightii* (e.g., AAC49784.1 GI:1336008), *Cuphea lanceolata* (e.g., CAA54060, GI495227), *Cuphea palustris*, (e.g., AAC49783.1 GI:1336006; AAC49179.1 GI:1215718); *Cuphea hookeriana* (e.g., AAC72882.1 GI:3859830; AAC49269.1 GI:1292906; AAC72881.1 GI:3859828; AAC72883.1 GI:3859832), *Cuphea calophylla* (e.g., ABB71580.1 GI:81361963) or genes of various *Cuphea* species disclosed in United States patent application publication US 2011/0020883, incorporated by reference herein) or genes from other higher plant species. For example, a microorganism used in the methods and cultures disclosed herein can include a gene encoding an acyl-ACP thioesterase from species such as but not limited to, *Arabidopsis* (XP_002885681.1 GI:297835598; NP_172327.1 GI:15223236); *Arachis hypogaea* (e.g., AB038556.1 GI:133754634); *Brassica* species (e.g., CAA52069.1 GI:435011), *Camellia oleifera* (e.g., ACQ57189.1 GI:229358082); *Cinnamonum camphorum* (e.g., AAC49151.1 GI:1143156); *Cocos nucifera*; *Glycine max* (e.g., ABD91726.1 GI:90192131); *Garcinia mangostana* (e.g., AAB51525.1 GI:1930081); *Gossypium hirsutum* (e.g., AAD01982.1 GI:4104242); *Helianthus annuus* (e.g., AAQ08226 GI:33325244); *Jatropha curcas* (e.g., ABU96744.1 GI:156900676); *Macadamia tetraphylla* (e.g., ADA79524.1 GI:282160399); *Elaeis oleifera* (e.g., AAM09524.1 GI:20067070); *Elaeis guineensis* (e.g., AAD42220 GI:30962820); *Oryza sativa* (e.g., BAA83582.1 GI:5803272); *Populus tomentosa* (e.g., ABC47311 GI:83778888); *Umbellularia californica* (e.g., AAC49001.1 GI:595955); *Ulmus Americana* (e.g., AAB71731.1 GI:2459533); and *Zea mays* (ACG41291.1 GI:195643646), or any of those disclosed in U.S. Pat. No. 5,455,167; U.S. Pat. No. 5,654,495; and U.S. Pat. No. 5,455,167; and in U.S. Patent Appl. Pub. Nos. 2009/0298143 and 2011/0020883; all incorporated by reference herein in their entireties. Further included are acyl-ACP thioesterases from mosses (Bryophyta), such as, for example, *Physcomitrella patens*, (e.g., XP 001770108 GI:168035219). These examples are not limiting with regard to the types or specific examples of acyl-ACP thioesterase genes that can be used.

Genes encoding acyl-ACP thioesterases of plants and bryophytes may include sequences encoding transit peptides for transport into plastids that can optionally be deleted for expression of N-terminally truncated thioesterases in host microorganisms including but not limited to prokaryotic host microorganisms, such as bacteria and cyanobacteria. Genes encoding thioesterases may further optionally include additional truncations, such as but not limited to N-terminal truncations that include a portion, such as up to ten, up to twenty, or up to thirty amino acids of a mature acyl-ACP thioesterase sequence.

Further included are acyl-ACP thioesterase genes from prokaryotic organisms. Illustrative examples of prokaryotic acyl-ACP thioesterases that may be expressed by a microorganism useful in the methods and cultures provided herein include, but are not limited to acyl-ACP thioesterases from *Desulfovibrio desulfuricans* (e.g., Q312L1 GI:123552742); *Elusimicrobium minutum* (e.g., ACC98705 GI:186971720); *Carboxydothermus hydrogenoformans* (e.g., YP_359670 GI:78042959); *Clostridium thermocellum* (e.g., YP_001039461 GI:125975551); *Moorella thermoacetica* (e.g., YP_431036 GI:83591027); *Geobacter metallireducens* (e.g., YP_384688 GI:78222941); *Salinibacter ruber* (e.g., YP_444210 GI:83814393); *Microscilla marina* (e.g., EAY28464 123988858); *Parabacteroides distasonis* (e.g., YP_001303423 GI:150008680); *Enterococcus faecalis* (e.g., ZP_03949391 GI:227519342); *Lactobacillus plantarum* (e.g., YP_003062170 GI:254555753); *Leuconostoc mesenteroides* (e.g., YP_817783 GI:116617412); *Oenococcus oeni* (e.g., ZP_01544069 GI:118586629); *Mycobacterium smegmatis* (e.g., ABK74560 GI:118173664); *Mycobacterium vanbaalenii* (e.g., ABM11638 GI:119954633); *Rhodococcus erythropolis* (e.g., ZP_04385507 GI:229491686; *Rhodococcus opacus* (e.g., YP_002778825 GI:226361047), or any of those disclosed in the co-pending, commonly-assigned U.S. patent application Ser. No. 13/324,623 entitled "Prokaryotic Acyl-ACP Thioesterases for Producing Fatty Acids in Genetically Engineered Microorganisms", filed on Dec. 13, 2011, and which is incorporated herein by reference in its entirety.

In additional embodiments, a gene encoding an acyl-CoA thioesterase can be introduced into a microorganism or host cell and can be from a plant, animal, or microbial source. For example, a gene encoding the TesA or TesB thioesterase of *E. coli*, or a variant thereof, for example, an acyl-CoA thioesterase such as, but not limited to, a variant as disclosed in WO 2010/075483, incorporated by reference herein in its entirety, can be introduced into a microorganism or host cell. Also included are genes encoding proteins that when queried against the Pfam database of protein families are identified as members of Pfam PF02551 (acyl-CoA thioesterase), where the bit score is equal to or greater than the gathering cut off (20.7).

Alternately or in addition, the microorganism or host cell of the invention can include one or more genes encoding a hydroxybenzoyl thioesterase, for example an exogenous 4-hydroxybenzoate thioesterase or 4-chlorobenzoate thioesterase. Genes encoding hydroxybenzoyl thioesterases that may be useful in a recombinant microorganism for producing free fatty acids can include, for example, those disclosed in the commonly-assigned U.S. patent application Ser. No. 13/324,607 entitled "Genetically Engineered Microorganisms Comprising 4-Hydroxybenzoyl-CoA Thioesterases and Methods of Using Same for Producing Free Fatty Acids and Fatty Acid Derivatives", filed on Dec. 13, 2011, and which is incorporated herein by reference in its entirety; 4-hydroxybenzoyl thioesterases from *Bacillus* species and

*Geobacillus* species; as well as 4-hydroxybenzoyl thioesterases of *Acidiphilium, Bartonella, Rhodopseudomonas, Magnetospirillum, Burkholderia, Granulibacter, Rhizobium,* and *Labrenzia* species, or the like, or combinations thereof.

Acyl-ACP thioesterases typically can be active to some degree on acyl-ACP substrates having a plurality of different acyl chain lengths, but can have higher activity on (e.g., have a substrate preference for) one or more acyl-ACP substrates having particular acyl chain lengths than on other chain length substrates. In some examples, an enzyme referred to as having a substrate preference for particular acyl chain length substrates produces at least twice as much product of the preferred substrate or substrates as it does from a non-preferred substrate, and for example can produce at least three times, at least four times, or at least five times as much product from a preferred substrate as from a non-preferred substrate. For example, an acyl-ACP thioesterase may have a substrate preference for one or more of acyl-ACP substrates having acyl chain lengths of 8, 10, 12, 14, 16, 18, 20, 22, and/or 24 carbons. Additionally or alternately, the acyl-ACP thioesterase can hydrolyze one or more acyl-ACP substrates having an acyl chain length from 8 to 18 carbons, for example from 12 to 18 carbons. For example, the acyl-ACP thioesterase can hydrolyze one or more acyl-ACP substrates having an acyl chain length from 12 to 16 carbons. Further additionally or alternately, an acyl-ACP thioesterases of the present invention can, in some embodiments, have its highest level of activity on an acyl-ACP substrate having an acyl chain length of 12, 14, and/or 16 carbons.

Microorganisms and Host Cells

A recombinant microorganism or host cell as provided herein comprises a non-native nucleic acid molecule encoding an LPAAT. The microorganism or host cell may be of prokaryotic or eukaryotic origin, and include, but are not limited to, photosynthetic organisms. "Photosynthetic organisms" are any prokaryotic or eukaryotic organisms that can perform photosynthesis. Photosynthetic organisms include higher plants (i.e., vascular plants), bryophytes, algae, and photosynthetic bacteria. The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "picoplankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria).

Algae for use in the invention, include without limitation, microalgae, such as but not limited to, an *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochytrium, Skeletonema, Spyrogyra, Stichococcus, Tetraselmis, Viridiella,* or *Volvox* species.

In some embodiments, photosynthetic bacteria, including for example, green sulfur bacteria, purple sulfur bacteria, green nonsulfur bacteria, purple nonsulfur bacteria, or cyanobacteria are used. Cyanobacterial species that can be used for production of fatty acid products include, without limitation, *Agmenellum, Anabaena, Anabaenopsis, Anacystis, Aphanizomenon, Arthrospira, Asterocapsa, Borzia, Calothrix, Chamaesiphon, Chroococcus, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* and *Xenococcus*. For example, the recombinant photosynthetic microorganism can be a *Cyanobium, Cyanothece,* or *Cyanobacterium* species, or further alternatively, the recombinant photosynthetic microorganism can be a *Gloeobacter, Lyngbya* or *Leptolyngba* species. Alternatively, the recombinant photosynthetic microorganism can be a *Synechococcus, Synechocystis,* or *Thermosynechococcus* species. A number of cyanobacterial species are known and have been manipulated using molecular biological techniques, including the unicellular cyanobacteria *Synechocystis* sp. PCC6803 and *Synechococcus* elongates PCC7942, whose genomes have been completely sequenced.

In addition to photosynthetic microorganisms and host cells, non-photosynthetic microorganisms and host cells such as fungi and non-algal stamenophiles can be used. Oleaginous yeasts, including but not limited to *Aspergillus niger, Yarrowia lypolytica, Cryptococcus curvatus, Cryptococcus terricolus, Candida species, Lipomyces starkeyi, Lipomyces lipofer, Endomycopsis vernalis, Rhodotorula glutinis,* and *Rhodotorula gracilis* can also be microorganisms and host cells for use in the invention. Other fungi, including but not limited to species of *Aspergillus, Trichoderma, Neurospora, Fusarium, Humicola, Rhizomucor, Kluyveromyces, Pichia, Mucor, Myceliophtora, Penicillium, Phanerochaete, Chrysosporium, Saccharomyces,* and *Schizosaccharomyces,* are also encompassed as microorganisms and host cells for use with the invention. *Labyrinthulomycete* species (e.g., *Thraustichytrium, Ulkenia,* and *Schizochytrium* species) can also be microorganisms and host cells for use in the invention.

In some embodiments, the microorganism or host cell is a bacterium, such as, but not limited to, an *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio,* or *Zymomonas* species.

The invention provides a recombinant microorganism comprising a non-native nucleic acid molecule that includes a nucleic acid sequence encoding an LPAAT and a non-native nucleic acid sequence that encodes a thioesterase. The nucleic acid sequence encoding the LPAAT and the nucleic acid sequence encoding the thioesterase can be present on the same or different nucleic acid molecules. The recombinant microorganism can produce a fatty acid product, such as a fatty acid, fatty alcohol, fatty aldehyde, fatty acid ester, wax ester, or hydrocarbon (such as an alkane or alkene). The recombinant host cell may comprise, e.g., any of the nucleic acid sequences encoding an LPAAT described herein and may comprise any of the nucleic acid sequences encoding a thioesterase described herein (e.g., an acyl-ACP thioesterase, an acyl-CoA thioesterase, or a 4-hydroxybenzoyl thioesterase). The recombinant host cell may comprise, e.g., any of the vectors described herein. In some embodiments, the nucleic acid sequence encoding the LPAAT gene is heterologous with respect to the recombinant host cell, and can be an LPAAT gene derived from any species, including plant, animal, or microbial species. Alternatively, the LPAAT gene may be homologous with respect to the host organism. For example, the non-native LPAAT gene may be an LPAAT gene that is native to the host microorganism and is introduced into the recombinant microorganism in an expression cassette that allows regulated expression or overexpression of the endogenous LPAAT gene. Alternatively, the LPAAT gene may be endogenous to the microorganism and a heterologous promoter may be introduced into the host microorganism such that it becomes juxtaposed with and operably linked to the endogenous LPAAT gene. The nucleic acid sequence encoding the thioesterase is can be derived from a gene that is homologous or heterologous with respect to the recombinant host cell. A thioesterase gene can be derived from an animal, plant, or microbial species.

The recombinant host cell can comprise a non-native gene encoding an LPAAT with at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to SEQ ID NO: 2, 3, 4, 5, 6, 7, 8, 9, 10, 11, 12, 13, 14, 15, 16, or 17, or a functional fragment of the LPAAT of the listed sequences. For example, the nucleic acid sequence can encodes the LPAAT of SEQ ID NO: 2, 3, 4, 5, 6, 7, 8, 9, 10, 11, 12, 13, 14, 15, 16, or 17. For example, the recombinant host cell can comprise a non-native gene encoding an LPAAT with at least 85%, 86%, 87%, 88%, 89%, 90%, 91%, 92%, 93%, 94%, 95%, 96%, 97%, 98%, or 99% sequence identity to SEQ ID NO: 2, and can encode an LPAAT with at least 90%, 95%, 96%, 97%, 98%, or 99% sequence identity to SEQ ID NO: 2. In further examples, the recombinant host cell can comprise a non-native gene encoding an LPAAT with at least 85%, 86%, 87%, 88%, 89%, 90%, 91%, 92%, 93%, 94%, 95%, 96%, 97%, 98%, or 99% sequence identity to SEQ ID NO: 3, 4, 5, 6, 7, 8, 9, 10, 11, 12, 13, 14, or 15. In yet other examples, the recombinant host cell can comprise a non-native gene encoding an LPAAT with at least 85%, 86%, 87%, 88%, 89%, 90%, 91%, 92%, 93%, 94%, 95%, 96%, 97%, 98%, or 99% sequence identity to SEQ ID NO: 16 or 17. In certain embodiments, the LPAAT encoded by the non-native nucleic acid molecule is derived from, e.g., a plant, fungal, or algal species, and may be derived from an LPAAT that is native to the host microorganism. In some embodiments, the recombinant host cell expresses an LPAAT with at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to a polypeptide comprising the amino acid sequence of SEQ ID NO: 18, 19, 20, or 21, or a functional fragment of the polypeptide. For example, the recombinant host cell can express an LPAAT with at least 85%, 86%, 87%, 88%, 89%, 90%, 91%, 92%, 93%, 94%, 95%, 96%, 97%, 98%, or 99% sequence identity to a polypeptide comprising the amino acid sequence of SEQ ID NO: 18, 19, 20, or 21.

Illustrative examples of recombinant microorganisms that express a non-native LPAAT gene and a non-native thioesterase gene include recombinant microorganisms such as but not limited to cyanobacteria that express a non-native gene encoding an LPAAT having a C18 substrate preference, such as an LPAAT having at least 85% identity to SEQ ID NO:2 (for example, at least 90% or at least 95% identity to SEQ ID NO:2) and a higher plant acyl-ACP thioesterase having a substrate preference for one or more of a C12, C14, or C16 acyl substrate, for example, the C12-preferring FatB1 thioesterase of *Umbellularia californica* (AAC49001.1 GI:595955), the C14-preferring thioesterase of *Cinnamomum camphorum* (Q39473.1 GI:8469216), the N-terminally truncated C16-preferring acyl-ACP thioesterase of *Elaeis oleifera* (SEQ ID NO:56), the C16-preferring acyl-ACP thioesterase of *Elaeis guineensis* (SEQ ID NO:57) or a truncated version thereof, the C14 and C16-preferring FatB2 thioesterase of *Cuphea palustris* (AAC49180.1 GI:1215720), Cc1FatB1 thioesterase of *Cuphea carthagenensis*, or a variant thereof (e.g., the truncated polypeptide of SEQ ID NO:44), or acyl-ACP thioesterases of other *Cuphea* species (see, for example, United States patent application publication US 2011/0020883), including, for example, the N-terminally truncated C14, C16-preferring Cd1FatB1 acyl-ACP thioesterase of SEQ ID NO:54 or a variant thereof, the N-terminally truncated C16-preferring Cp1FatB1 thioesterase of SEQ ID NO:55 or a variant thereof, or the C14, the C16-preferring *C. hookeriana* FatB1 thioesterase (Q39513.1 GI:8469217). Also specifically considered are thioesterases having at least 85% identity, for example at least 90% or at least 95% identity to the aforementioned *Umbellularia, Cinnamomum, Cuphea* and *Elaeis* acyl-ACP thioesterases, in which the acyl-ACP thioesterases have C12, C14, and/or C16 substrate specificities.

Further illustrative and non-limiting examples include recombinant microorganisms that express a non-native LPAAT gene encoding an LPAAT having a C18 substrate preference in combination with any of the acyl-ACP thioesterase provided above (e.g., the *Umbellularia, Cinnamomum, Cuphea* and *Elaeis* acyl-ACP thioesterases, including acyl-ACP thioesterases of SEQ ID NO:54, 55, 56, and 57 and variants thereof). LPAATs having a C18 substrate preference include, for example, the LPAATs disclosed hereinabove having at least 85%, for example at least 90% or at least 95% to microsomal LPAATs such as SEQ ID NO 22, 23, 24, 25, and 26. Other LPAATs specifically considered for expression in a host microorganism in combination with C12, C14, and/or C16 preferring acyl-ACP thioesterases including those of SEQ ID NO:54, 55, 56, or 57 and thioesterases having at least 85%, 90%, or 95% identity to SEQ ID NO:54, 55, 56, or 57 or truncations thereof, include cyanobacterial orthologs of the *Synechocystis* C18-preferring LPAAT of SEQ ID NO:2, including but not limited to LPAATs of SEQ ID NOs: 3, 4, 5, 6, 7, 8, 9, 10, 11, 12, 13, 14, and 15, and LPAATs having at least 85%, at least 90%, or at least 95% to these or other cyanobacterial orthologs of the LPAAT encoded by the *Synechocystis* sll1752 gene (SEQ ID NO:1).

In some examples, the recombinant host cell can comprises a nucleic acid sequence encoding an LPAAT with at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO: 1, or to a fragment of the nucleotide sequence that encodes a functional fragment of the LPAAT. In certain embodiments, the nucleic acid sequence encoding the LPAAT comprises the nucleotide sequence of SEQ ID NO: 1. In some embodiments, the recombinant host cell is a photosynthetic host cell, and the non-native nucleic acid sequences encoding the LPAAT and/or the thioesterase are codon optimized for expression in the host cell.

The recombinant host cell expressing an LPAAT gene in combination with a thioesterase gene produces a greater amount of a fatty acid product than a control host cell that does not express the LPAAT gene. In some embodiments, the amount of fatty acid product produced by a culture of the recombinant host cell expressing a non-native gene encoding an LPAAT and a non-native gene encoding a thioesterase is at least 10%, 15%, 20%, 25%, 30%, 40%, 50%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, or 1000% greater than the amount of wax ester produced by a control host cell that does not express the non-native LPAAT gene.

In some embodiments, the recombinant host cell expressing an LPAAT and a thioesterase produces a greater amount of a fatty acid product than a control host cell that does not express the LPAAT and the thioesterase. In some embodiments, the amount of a fatty acid product produced by a culture of the recombinant host cell expressing an LPAAT and a thioesterase is at least 10%, 15%, 20%, 25%, 30%, 40%, 50%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, or 1000% greater than the amount of fatty acid product produced by a control host cell that does not express the LPAAT and the thioesterase.

Additional Host Cell Modifications for Free Fatty Acid (FFA) Production

Further modifications to the recombinant microorganisms or host cells of the invention can be made to affect free fatty acid production. For example, the recombinant microorganism can include one or more additional non-native genes whose expression increases the production of a fatty acid product. The additional gene may be encoded by a nucleic acid molecule that is the same as the nucleic acid molecule that encodes the LPAAT and/or the nucleic acid molecule that encodes the thioesterase, or the additional gene may be encoded by a separate nucleic acid molecule. Where two or more genes are encoded by the same nucleic acid molecule (e.g., on the same expression vector), the expression of each gene may optionally be independently regulated by a same or a different promoter and/or enhancer. In certain embodiments, the additional gene may increase the rate and/or level of free fatty acid or fatty acid derivative production.

For example, the recombinant host cell expressing an LPAAT, and, preferably, a thioesterase, can further express at least one additional recombinant or exogenous gene that encodes a polypeptide having lipolytic activity. For example, a recombinant microorganism or host cell of the invention can include one or more genes encoding one or more polypeptides having lipolytic activity, where the polypeptide(s) having lipolytic activity are capable of producing free fatty acids from membrane lipids or storage lipids, e.g., phospholipids, triacylglycerols, diacylglycerols, monoacylglycerols, or the like, or combinations thereof. The polypeptides having lipolytic activity can be, for example, lipases, esterases, cutinases, or amidases.

Without limiting the invention to any particular mechanisms, it is considered that overexpression of an LPAAT gene may result in significantly increased production of membrane or storage lipids. Excess membrane or storage lipids can be acted on by polypeptides having lipolytic activity (such as, e.g., one or more lipases or amidases) to release additional fatty acids (that can optionally be further converted to fatty acid derivatives), thereby further increasing the amount of fatty acid products made by the recombinant microorganism (see, for example, the model provided in FIG. 2).

The use of genes encoding polypeptides having lipolytic activity in microorganisms for the production of free fatty acids is disclosed in commonly-assigned U.S. patent application Ser. No. 13/324,653 entitled "Production of Free Fatty Acids and Fatty Acid Derivatives by Recombinant Microorganisms Expressing Polypeptides Having Lipolytic Activity," filed on Dec. 13, 2011, and which is incorporated herein by reference in its entirety. The polypeptide having lipolytic activity can be for example a lipase, e.g., that liberates a fatty acid from a glycerolipid (including a monoglyceride, a diglyceride, a triglyceride, a phospholipid, a galactolipid, etc.) or can be an amidase. For example, the recombinant microorganism can include a non-native gene encoding a lipase, such as but not limited to a lipase that is a member of a Pfam belonging to the AB Hydrolase Pfam clan (CL0028). For example, a non-native gene encoding a polypeptide having lipolytic activity can encode a lipase that includes a LipA domain identified as conserved protein domain COG1075, or is included in the protein family Pfam PF01674 (Lipase 2); a non-native nucleic acid molecule that encodes a lipase that includes a Lipase 3 domain identified as conserved protein domain COG3675, or is included in the protein family Pfam PF01764 (Lipase 3); a non-native nucleic acid molecule that encodes a lipase that is included in the protein family Pfam PF07819 (PGAP1); or a non-native nucleic acid molecule that encodes a polypeptide that is included in any of the protein families Pfam PF03583, Pfam PF00151 (Lipase), Pfam PF00561 (Ab hydrolase 1), Pfam PF02230 (Ab hydrolase 2), Pfam PF07859 (Ab hydrolase 3), Pfam PF08386 (Ab hydrolase 4), Pfam PF12695 (Ab hydrolase 5), Pfam PF12697 (Ab hydrolase 6), Pfam PF12715 (Ab hydrolase 7), Pfam PF04083 (Ab hydro lipase). In some embodiments, an exogenous lipase gene introduced into a microorganism can encode a protein with an amino acid sequence having an E-value parameter of 0.01 or less when queried using the Pfam Profile HMM for any of Pfam PF01674, Pfam PF01764, Pfam PF07819, Pfam PF03583, and/or Pfam PF00151. Further, the recombinant microorganism can include a non-native gene encoding an amidase having lipolytic activity, such as but not limited to an amidase that recruits to Pfam PF01425 (Amidase) with a bit score greater than the gathering cutoff of 20.1 and can catalyze the release of fatty acids from lipids.

Additionally or alternately contemplated are recombinant microorganisms that are engineered to include gene regulatory sequences that induce or increase expression of an endogenous lipase gene. For example, a microorganism can be engineered such that a heterologous promoter is inserted upstream of a coding region of an endogenous lipase gene. The heterologous promoter can replace an endogenous promoter and/or can be inserted upstream or downstream of the endogenous promoter that regulates expression of the endogenous lipase gene, for example using homologous recombination or site-specific recombination. The heterologous promoter can be a constitutive promoter or an inducible promoter that increases expression of the endogenous lipase gene.

Further modifications to the recombinant microorganisms or host cells of the invention can be made to affect free fatty acid production. For example, a recombinant microorganism or host cell of the invention can include one or more exogenous nucleic acid molecules that encode a polypeptide that participates in the synthesis of a fatty acid, including, but not limited to, an acetyl-CoA carboxylase, a malonyl CoA: ACP transacylase, or a beta-ketoacyl-ACP synthase.

Additionally or alternatively, the recombinant microorganism or host cell can comprise a modification of an endogenous nucleic acid molecule that encodes, e.g., an acyl-CoA synthetase, acyl-ACP synthetase, acyl CoA dehydrogenase, glycerol-3-phosphate dehydrogenase, acetaldehyde CoA dehydrogenase, pyruvate dehydrogenase, acetate kinase, and the like, and combinations thereof. In certain embodiments, the modification down-regulates the endogenous nucleic acid and includes partial, substantial, or complete deletion, silencing, or inactivation of the nucleic acid or its regulatory elements.

In some examples, the host cell can have attenuated expression of an endogenous gene encoding an acyl-ACP synthetase which participates in the recycling of fatty acids into lipids. The endogenous acyl-ACP synthetase gene can be, for example, downregulated by deletion or mutation of the promoter, or the protein-encoding of the gene can be internally deleted or disrupted, for example, by insertional mutagenesis. Alternatively, the entire acyl-CoA synthetase gene can be deleted, for example, by homologous recombination or other genome modification techniques. In yet further alternatives, gene knockdown constructs such as but not limited to ribozyme, antisense, or RNAi constructs can be introduced into the host cell to attenuate expression of the endogenous acyl-ACP synthetase gene.

Additionally or alternatively, the recombinant microorganism or host cell can be modified such that one or more genes that encode beta-oxidation pathway enzymes have been inactivated and/or down-regulated, and/or such that the enzymes themselves that are operative on such beta-oxidation pathways may be inhibited. This could prevent the degradation of fatty acids released from acyl-ACPs, thus enhancing the yield of fatty acid products. In cases where the desired products are medium-chain fatty acids, the inactivation and/or down-regulation of genes that encode acyl-CoA synthetase and/or acyl-CoA oxidase enzymes that preferentially use these chain lengths as substrates can be made. Mutations in the genes encoding medium-chain-specific acyl-CoA synthetase and/or medium-chain-specific acyl-CoA oxidase enzymes, such that the activity of the enzymes are diminished, may additionally or alternately be effective in increasing the yield of produced and/or released fatty acid products. Mutations in the genes can be introduced either by recombinant or non-recombinant methods.

Genes may be targeted specifically by disruption, deletion, generation of antisense sequences, generation of ribozymes, RNAi, meganuclease genome modification, and/or other recombinant approaches. Inactivation of the genes can additionally or alternatively be accomplished by random mutation techniques such as exposure to UV and/or chemical mutagens, and the resulting genes and/or enzymes can be screened for mutants with the desired activity. The proteins themselves can be inhibited by intracellular generation of appropriate antibodies, intracellular generation of peptide inhibitors, or the like, or some combination thereof.

In additional embodiments, a recombinant microorganism or host cell of the invention comprises can be modified such that one or more genes that encode storage carbohydrate and/or polyhydroxyalkanoate (PHA) biosynthesis pathway enzymes are inactivated or down-regulated, and/or such that the enzymes themselves that are operative on such pathways are inhibited. Examples include, but are not limited to, enzymes involved in glycogen, starch, or chrysolaminarin synthesis, including glucan synthases and/or branching enzymes. Other examples include enzymes involved in PHA biosynthesis such as acetoacetyl-CoA synthase and PHA synthase.

Modifications for Fatty Acid Derivative Production

The recombinant microorganisms or host cells of the invention can include additional modifications for the production of fatty acid derivatives such as, e.g., fatty aldehydes, fatty alcohols, fatty acid esters, wax esters, and hydrocarbons, including alkanes and alkenes. In some embodiments, the recombinant microorganism or host cell comprises one or more nucleic acid molecules encoding an exogenous acyl-CoA reductase, carboxylic acid reductase, and/or acyl-ACP reductase and can produce a fatty alcohol.

For example, for the production of fatty aldehydes, which can optionally be further converted to products such as fatty alcohols, wax esters, or alkanes, a transgenic microorganism as provided herein can include an exogenous gene(s) that encodes an aldehyde-forming reductase, such as, for example, an aldehyde-forming acyl-CoA reductase, an aldehyde-forming acyl-ACP reductase, or a carboxylic acid reductase. Genes or portions of genes that are listed in GenBank and other genetic databases and that are predicted to encode proteins that are homologous to known acyl-CoA reductases that produce fatty aldehydes, referred to herein as "aldehyde-generating fatty acyl-CoA reductases", can be introduced into various microorganisms in order to test for the production of specific fatty aldehydes or fatty alcohols produced therefrom. Nonlimiting examples of fatty aldehyde-generating acyl-CoA reductases include the Acr1 gene of *Acinetobacter baylyi* (Accession U77680, GI:1684885), the AcrM-1 gene of *Acinetobacter* sp. M-1 (Accession YP 001086217, GI:18857900), and the luxC and luxE genes of various photoluminescent bacteria, e.g, an *Altermonas, Photobacterium, Shewanella, Vibrio,* or *Xenorhabdus* species. The enzymes encoded by these and other genes identified, for example, by sequence homology or protein domain can be tested to determine their substrates and products using assays know in the art.

Nonlimiting examples of carboxylic acid reductases that can be used in the invention include the *Nocardia* CAR gene (Accession AY495697; GI:40796034) and homologs thereof, some of which are disclosed in US2010/0105963, incorporated by reference herein.

In some examples, the host cell can include a non-native gene encoding an aldehyde-forming acyl-ACP reductase such as but not limited to any of those disclosed in WO 2009/140696 and WO 2011/066137. For example, the recombinant host cell may comprise an aldehyde-forming acyl-ACP reductase that has at least 50%, 60%, 70%, 80%, 90% or 95% sequence identity to an aldehyde-forming reductase, e.g., as disclosed in WO 2009/140696 or WO 2011/066137, such as, for example, any of the reductases having the accession numbers AAM82647; AAM82647; BAD78241; ABA22149; BAB76983; ZP_03763674; ACL42791; ZP_01628095; ZP_01619574; YP_001865324; YP_721978; NP_682102; YP_001518341; YP_002371106; ZP_05027136; ZP_03273554; NP_442146; ZP_01728620; ZP_05039135; YP_001802846; NP_926091; YP_001660322; ZP_00516920; CAO90781; ZP_01085337; YP_001227841; ABD96327; NP_897828; YP_001224378; ABD96480; ZP_01123215; ABB92249;

ZP_01079773; YP_377636; NP_874926; NP_895058; ABD96274; ABD96442; ZP_01469469; ZP_05045052; YP_001014416; YP_001010913; YP_381056; YP_001550421; NP_892651; YP_001090783; ZP_01472595; YP_293055; ZP_05138243; YP_731192; YP_001483815; YP_001008982; YP_473896; YP_478638; or YP_397030. In some embodiments the recombinant host cell includes an exogenous gene encoding an aldehyde-forming acyl-ACP reductase, where the aldehyde-forming acyl-ACP reductase can be from a cyanobacterial species, and may be from the same species as the host microorganism, or may be from a different species. Alternatively, a cyanobacterial host can be engineered to overexpress an endogenous acyl-ACP reductase gene.

For the production of fatty alcohols, a recombinant microorganism as provided herein can include an exogenous gene encoding an alcohol-forming acyl reductase such as bfar from *Bombyx mmori*; jjfar from *Simmondsia chinensis*, an acyl-CoA reductase from *Titicum aestivum*, mfar1 of *Mus musculus*, mfar2 from *Mus musculus*, hfar from *H. sapiens*, FARXIII of *Ostrinia scapulalis*, MS2 of *Z. mays*, the putative fatty acyl-coA reductase of *Oryza sativa* (GenBank accession BAC84377) or MS2, FAR4, FARE, or CER4 of *Arabidopsis thaliana*. An alcohol-forming fatty acyl-CoA reductase can also be a prokaryotic enzyme, such as for example, those having Genbank accession numbers AAC45217 (*Acinetobacter baylyi* fatty acyl-CoA reductase), YP_047869 (*Acinetobacter* sp. ADP1 fatty acyl-CoA reductase), BAB85476 (*Acinetobacter* sp. M-1 acyl coenzyme A reductase), YP_001086217 (*Acinetobacter baumannii* ATCC 17978 acyl coenzyme A reductase), YP_580344 short-chain dehydrogenase/reductase SDR [*Psychrobacter cryohalolentis* K5], YP_001280274 (*Psychrobacter* sp. PRwf-1 short-chain dehydrogenase/reductase SDR), the acyl reductase of *Marinobacter algicola* DG893 (Accession ZP_01892457), the short chain acyl dehydrogenase of *Marinobacter aquaeolei* Maqu_2507 (YP_959769) *Marinobacter aquaeolei* VT8 Maqu_2220 (YP_959486), *Hahella chejuensis* Hch_05075 (YP_436183), *Marinobacter adhaerens* HP15_810 (ADP96574), or an acyl reductase of an *Oceanobacter* species (e.g., RED65_09894, Accession EAT13695). Alcohol-forming reductases may include those that are able to use acyl-ACP as a substrate, as disclosed in the co-pending, commonly-assigned U.S. patent application No. 61/539,640 entitled "Fatty Alcohol-Forming Acyl-ACP Reductases", filed on Sep. 27, 2011, and which is incorporated herein by reference in its entirety.

Alternatively or in addition, the recombinant microorganism or host cell comprises one or more nucleic acid molecules encoding an exogenous acyl-CoA reductase, carboxylic acid reductase, and/or acyl-ACP reductase, and an exogenous wax synthase and can produce a wax ester. Wax esters include an A chain and a B chain linked through an ester bond, one or both of which can be derived from a fatty acid generated by the recombinant microorganisms or host cells of the invention. Wax esters produced by the recombinant microorganisms or host cells of the invention include, e.g., A chain lengths of from 8 to 24 carbons, for example, 12 to 18 carbons, or 12 to 16 carbons, and/or B chain lengths of from 8 to 24 carbons, for example, 12 to 18 carbons, or 12 to 16 carbons. For example, the wax esters can have A+B chain lengths including, but not limited to, of 16 to 48 carbons, 24 to 36 carbons, or 24 to 32 carbons.

Wax synthases include polypeptides having enzyme classification number EC 2.3.1.75, as well as any other peptide capable of catalyzing the conversion of an acyl-thioester to fatty esters, e.g., some acyltransferases, including some DGATs. Some wax synthase peptides can catalyze other reactions as well, for example some wax synthase peptides will accept short chain acyl-CoAs and short chain alcohols to produce fatty esters. Methods to identify wax synthase activity are provided in U.S. Pat. No. 7,118,896, which is herein incorporated by reference. Nonlimiting examples of wax synthases that can be encoded by an exogenous nucleic acid molecule introduced into a recombinant microorganism as disclosed herein include the bifunctional wax ester synthase/acyl-CoA:diacylglycerol acyltransferase of *Simmondsia chinensis* (AAD38041), the wax synthase of *Acinetobacter* sp. strain ADP 1 (CAG67733), *Pseudomonas aeruginosa* (AAG06717), *Arabidopsis thaliana* (Q93ZR6), *Alcanivorax* (EDX90960), *Rhodococcus opacus* (YP_002782647), *Homo sapiens* (Q6E213), *Mus musculus* (Q6E1M8), or *Petunia×hybrida* (AAZ08051).

In some embodiments, the recombinant microorganisms or host cells of the invention comprise at least one nucleic acid molecule encoding an exogenous fatty acid decarboxylase or an exogenous fatty aldehyde decarbonylase, or additionally at least one exogenous nucleic acid molecule encoding an exogenous acyl-CoA reductase, carboxylic acid reductase, or acyl-ACP reductase, and can produce an alkane and/or alkene. Alkanes and alkenes produced by the recombinant microorganisms or host cells of the invention can, for example, have chain lengths of 7, 9, 11, 13, 15, 17, 19, 21, and/or 23 carbons, including, for example, chain lengths of 7, 9, 11, 13, 15, and/or 17 carbons, or chain lengths of 7, 9, 11, 13, and/or 15 carbons, or chain lengths of 11, 13, and/or 15 carbons.

Additionally, the recombinant microorganisms or host cells of the invention that produce a fatty alcohol, fatty aldehyde, fatty acid ester, wax ester, or hydrocarbons, including an alkane or an alkene, may optionally include a nucleic acid molecule encoding an exogenous acyl-CoA synthetase, or may be engineered to have upregulated expression of an endogenous acyl-CoA synthetase gene.

Additionally, the recombinant host cell may optionally be engineered to express an exogenous transmembrane transporter to facilitate secretion of one or more fatty acid products. For example, the recombinant host cell can include a non-native gene encoding an ATP-binding cassette (ABC) transporter or an RND pump. In some embodiments, the transporter is at least 80% identical in sequence to a transporter protein encoded by an *Arabidopsis* genes CER5, WBC11, AtMRPS, AmiS2 and AtPGP1, or fatty acid transporter (FATP) genes from *Saccharomyces, Drosophila*, mycobacterial species, or mammalian species.

Also included are genes encoding variants of these and other naturally-occurring enzymes that participate in the synthesis of fatty acid products having at least 65% identity to the referenced or naturally-occurring proteins, in which the activity of the enzyme is not substantially reduced with respect to the wild-type or above-referenced enzyme.

The above-described recombinant host cells may be used in any of the methods of producing a fatty acid product as described herein.

Nucleic Acid Molecules

The nucleic acid molecules and polypeptides described herein can be used in any of the methods of the invention, and may be included in any of the vectors or recombinant microorganisms of the invention. Nucleic acid molecules comprising sequences that encode LPAATs are provided for use in host microorganisms and methods for producing fatty acid products, including free fatty acids, fatty aldehydes, fatty alcohols, fatty acid esters, wax esters, alkanes, and/or alkenes. A nucleic acid molecule as disclosed herein can be isolated and/or purified.

In some embodiments, expression in a host microorganism (such as a recombinant microorganism that expresses a non-native gene encoding a thioesterase) of a recombinant nucleic acid molecule or sequence encoding an LPAAT as described herein results in a higher production level of a fatty acid or a fatty acid derivative by the host microorganism than the production level in a control microorganism, where the control microorganism is cultured under the same conditions and is substantially identical to the microorganism expressing the non-native nucleic acid molecule or sequence encoding the LPAAT in all respects, with the exception that the control microorganism does not express a non-native nucleic acid molecule that encodes an LPAAT. In particular embodiments the recombinant microorganism can be a photosynthetic microorganism.

In further embodiments, expression in a host microorganism of a non-native nucleic acid sequence encoding an LPAAT and a non-native nucleic acid sequence encoding a thioesterase as described herein results in a higher production level of a fatty acid product by the host microorganism than the production level in a control microorganism, where the control microorganism is cultured under the same conditions and is substantially identical to the microorganism expressing the recombinant nucleic acid molecule(s) or sequences in all respects, with the exception that the control microorganism does not express a thioesterase and does not express a non-native nucleic acid sequences encoding an LPAAT. In particular embodiments, the recombinant microorganism can be a photosynthetic microorganism.

The recombinant host cells or microorganisms can include, for example, an isolated nucleic acid molecule encoding a polypeptide having LPAAT activity, in which the polypeptide comprises an amino acid sequence having at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, 3, 4, 5, 6, 7, 8, 9, 10, 11, 12, 13, 14, 15, 16, 17, 18, 19, 20, 21, 22, 23, 24, 25, or 26, or to a functional fragment of any of the provided amino acid sequences.

An isolated or recombinant nucleic acid molecule encoding an LPAAT can comprise a nucleic acid sequence that encodes a polypeptide having LPAAT activity that has at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of SEQ ID NO: 2, 3, 4, 5, 6, 7, 8, 9, 10, 11, 12, 13, 14, 15, 16, or 17, or to a portion thereof, for example, to a functional fragment of the polypeptide. For example, a nucleic acid sequence can encode a polypeptide having LPAAT activity that can include an amino acid sequence having at least 85% sequence identity to the amino acid sequence of SEQ ID NO:2, 3, 4, 5, 6, 7, 8, 9, 10, 11, 12, 13, 14, 15, 16, or 17 or a functional fragment thereof, or having at least 90% sequence identity to the amino acid sequence of SEQ ID NO: 2, 3, 4, 5, 6, 7, 8, 9, 10, 11, 12, 13, 14, 15, 16, or 17, or a functional fragment thereof, or, for example, having at least 95% sequence identity to the amino acid sequence of SEQ ID NO:2, 3, 4, 5, 6, 7, 8, 9, 10, 11, 12, 13, 14, 15, 16, or 17, or a functional fragment thereof, and can comprise a nucleotide sequence that encodes a polypeptide comprising all or an active fragment of the amino acid sequence of SEQ ID NO: 2, 3, 4, 5, 6, 7, 8, 9, 10, 11, 12, 13, 14, 15, 16, or 17. In some examples, a nucleic acid sequence that encodes a polypeptide having LPAAT activity can have at least 85% sequence identity to the amino acid sequence of SEQ ID NO:2, can have at least 90% sequence identity to the amino acid sequence of SEQ ID NO:2, or can have at least 95% sequence identity to the amino acid sequence of SEQ ID NO:2.

Additionally or alternately, an isolated nucleic acid molecule useful in the methods and microorganisms of the invention can comprise a nucleic acid sequence that encodes an LPAAT, where the nucleic acid sequence has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the nucleotide sequence of SEQ ID NO:1, or to a fragment of the nucleotide sequence of SEQ ID NO:1 that encodes a functional fragment of the LPAAT of SEQ ID NO:2. In some embodiments, the invention provides an isolated or recombinant nucleic acid molecule that encodes an LPAAT, where the nucleic acid sequence has at least 85%, at least 90%, or at least 95% sequence identity to the nucleotide sequence of SEQ ID NO:1, or to a fragment of the nucleotide sequence of SEQ ID NO:1 that encodes a functional fragment of the acyl-ACP wax ester synthase of SEQ ID NO:2. In some embodiments, the invention provides an isolated nucleic acid molecule that comprises the nucleic acid sequence of SEQ ID NO:1

An isolated or recombinant nucleic acid molecule encoding an LPAAT can comprise a nucleic acid sequence that encodes a polypeptide having LPAAT activity that has at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of a prokaryotic LPAAT, such as but not limited to plsC of *E. coli* (SEQ ID NO:16) and orthologs thereof in other bacterial species, or the LPAAT of *Marinobacter adhaerens* HP15 (Genbank accession ADP99136, gene identifier 311696263; SEQ ID NO:17) and orthologs in other bacterial species. For example, in some instances an isolated or recombinant nucleic acid molecule encoding an LPAAT can comprise a nucleic acid sequence that encodes a polypeptide having LPAAT activity that has at least 85%, 90%, 95%, or 99% sequence identity to the amino acid sequence of a prokaryotic LPAAT, such as but not limited to plsC of *E. coli* (SEQ ID NO:16) and orthologs thereof in other bacterial species, or the LPAAT of *Marinobacter adhaerens* HP15 (Genbank accession ADP99136, gene identifier 311696263; SEQ ID NO:17) and orthologs in other bacterial species.

Further, isolated or recombinant nucleic acid molecule encoding an LPAAT can comprise a nucleic acid sequence that encodes a polypeptide having LPAAT activity that has at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of a eukaryotic LPAAT, such as a plastidal LPAAT that can be derived from a plant or algal species, such as, for example the LPAAT of *Oryza sativa* (SEQ ID NO:18), the LPAAT of *Glycine max* (SEQ ID NO:19); the LPAAT of *Brassica napus* (SEQ ID NO:20), and the LPAAT of *Arabidopsis thaliana* (SEQ ID NO:21), or to a functional fragment thereof, or to other plastidal LPAATs, including functional fragments thereof.

Additionally, an isolated or recombinant nucleic acid molecule encoding an LPAAT can comprise a nucleic acid sequence that encodes a polypeptide having LPAAT activity that has at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of a eukaryotic microsomal LPAAT, including but not limited to SEQ ID NO:22 of *Zea mays*, SEQ ID NO:23 of *Arabidopsis thaliana*, SEQ ID NO:24 of *Arabidopsis thaliana*, SEQ ID NO:25 of *Brassica napus*, and SEQ ID NO:26 of *Prunus dulcis*, or to a fragment thereof demonstrating LPAAT activity. For example, a microorganism as provided herein can include a non-native gene encoding an LPAAT having at least 85%, at least 90%, at least 95%, at least 96%, at least 97%, at least 98%, at least 99%, or 100% identity to any of SEQ ID NO:22, SEQ ID NO:23, SEQ ID NO:24, SEQ ID NO:25, or SEQ ID NO:26.

In some embodiments, the invention encompasses nucleic acid molecules encoding deletion mutants of an LPAAT where one or more amino acids have been deleted from the protein. For example, the encoded polypeptide can lack at least 1, 2, 3, 4, 5, 6, 7, 8, 9, 10, 20, 30, 40, 50, 60, 70, or 80 amino acids from the N- and/or C-terminus and can have an amino acid sequence at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of SEQ ID NO: 2, 3, 4, 5, 6, 7, 8, 9, 10, 11, 12, 13, 14, 15, 16, 17, 18, 19, 20, 21, 22, 23, 24, 25, or 26. In some examples, the deleted sequences may include targeting sequences, for example, at least a portion of a chloroplast transit peptide, at least a portion of a mitochondrial targeting sequence, at least a portion of an endoplasmic reticulum targeting sequence, etc.

Further, the invention provides nucleic acid molecules encoding variants of naturally-occurring LPAAT amino acid sequences, such as but not limited to variants of LPAAT sequences of SEQ ID NO: 2, 3, 4, 5, 6, 7, 8, 9, 10, 11, 12, 13, 14, 15, 16, 17, 18, 19, 20, 21, 22, 23, 24, 25, or 26 or fragments thereof. Variants may be naturally occurring, or non-naturally-occurring, such as those induced by various mutagens and mutagenic processes. In some embodiments, a nucleic acid molecule encodes a variant of an LPAAT in which at least one amino acid residue has been inserted N- and/or C-terminal to, and/or within, the reference sequence. In some embodiments, at least one amino acid residue has been deleted N- and/or C-terminal to, and/or within, the reference sequence. In some embodiments, the nucleic acid molecules may encode variants that may be sequences containing predetermined mutations by, e.g., homologous recombination or site-directed or PCR mutagenesis; corresponding proteins of other species; alleles or other naturally occurring variants; and/or derivatives wherein the protein has been covalently modified by chemical, enzymatic or other appropriate means with a moiety other than a naturally occurring amino acid.

A substitution, insertion or deletion can adversely affect the protein when the altered sequence substantially inhibits a biological function associated with the protein. In certain embodiments, a variant of an LPAAT may have activity that is reduced by not more than about 1%, 2%, 3%, 4%, 5%, 6%, 7%, 8%, 9%, 10%, 15%, 20%, 30%, 40%, or 50%, in comparison to the activity of the LPAAT from which the variant is derived (e.g., any of SEQ ID NO: 2, 3, 4, 5, 6, 7, 8, 9, 10, 11, 12, 13, 14, 15, 16, 17, 18, 19, 20, 21, 22, 23, 24, 25, or 26, or other LPAATs). In some embodiments, the amount of a fatty acid product produced by a host cell expressing the LPAAT variant is not less than about 99%, 98%, 97%, 96%, 95%, 94%, 93%, 92%, 91%, 90%, 85%, 80% or 75% of the amount or the fatty acid product produced by a host cell expressing the LPAAT from which the variant is derived (e.g., e.g., any of SEQ ID NO: 2, 3, 4, 5, 6, 7, 8, 9, 10, 11, 12, 13, 14, 15, 16, 17, 18, 19, 20, 21, 22, 23, 24, 25, or 26, or other LPAATs).

The invention also provides fragments and variants of an LPAAT that have increased activity in comparison to the reference polypeptides. In certain embodiments, the LPAAT fragment or variant may have activity that is increased by at least 5%, 10%, 20%, 30%, 40%, 50%, 60%, 70%, 80%, 90%, 100%, 200%, 300%, 400%, 500%, 600%, 700%, 800%, 900%, or 1000% in comparison to the activity of the LPAAT from which the variant is derived. In certain embodiments, the amount of fatty acid or fatty acid derivative produced by a host cell expressing the fragment or variant is at least 5%, 10%, 20%, 30%, 40%, 50%, 60%, 70%, 80%, 90%, 100%, 200%, 300%, 400%, 500%, 600%, 700%, 800%, 900% or 1000% of the amount of fatty acid product made by a host cell expressing the LPAAT from which the fragment or variant is derived.

Any of the provided nucleic acid molecules can optionally further comprise an additional nucleic acid sequence of at least 50, 60, 70, 80, 90, 100, 150, 200, 250, 300, 350, 400, 450, 500, 550, 600, 700, 800, 900, 1000, or 1500 nucleotides from a photosynthetic organism.

Other Modifications

The invention also provides further variants of the nucleotide sequences of the invention. In some embodiments, the nucleotide sequence variants encode fragments or variants of the polypeptides as described herein. In some embodiments, the nucleotide sequence variants are naturally-occurring. In other embodiments, the nucleotide sequence variants are non-naturally-occurring, such as those induced by various mutagens and mutagenic processes. In certain embodiments, the nucleotide sequence variants are a combination of naturally- and non-naturally-occurring. A given nucleic acid sequence may be modified, for example, according to standard mutagenesis or artificial evolution or domain swapping methods to produce modified sequences. Accelerated evolution methods are described, e.g. by Stemmer (1994) *Nature* 370, 389-391, and Stemmer (1994) *Proc. Natl. Acad. Sci. USA* 91, 10747-10751. Chemical or enzymatic alteration of expressed nucleic acids and polypeptides can be performed by standard methods. For example, a sequence can be modified by addition of phosphate groups, methyl groups, lipids, sugars, peptides or organic or inorganic compounds, by the inclusion of modified nucleotides or amino acids, or the like.

For optimal expression of a recombinant protein, in certain instances it may be beneficial to employ coding sequences that produce mRNA with codons preferentially used by the host cell to be transformed ("codon optimization"). Thus, for enhanced expression of transgenes, the codon usage of the transgene can be matched with the specific codon bias of the organism in which the transgene is desired to be expressed. Methods of recoding genes for expression in microalgae are described in, e.g., U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. In some embodiments, only a portion of the codons is changed to reflect a preferred codon usage of a host microorganism. In certain embodiments, one or more codons are changed to codons that are not necessarily the most preferred codon of the host microorganism encoding a particular amino acid. Additional information for codon optimization is available, e.g. at the codon usage database of GenBank. The coding sequences may be codon optimized for optimal production of a desired product in the host organism selected for expression. In certain embodiments, the non-native nucleic acid sequence encoding an LPAAT and/or the non-native nucleic acid sequence encoding a thioesterase is codon optimized for expression in a photosynthetic microorganism, e.g., a *cyanobacterium* or a eukaryotic microalga.

In some embodiments, the nucleic acid molecules of the invention encode fusion proteins that comprise an LPAAT. For example, the nucleic acids of the invention may comprise polynucleotide sequences that encode glutathione-S-transferase (GST) or a portion thereof, thioredoxin or a portion thereof, maltose binding protein or a portion thereof, polyhistidine (e.g. $His_6$), poly-HN, poly-lysine, a hemagglutinin tag sequence, HSV-Tag and/or at least a portion of HIV-Tat fused to the LPAAT-encoding sequence.

In some embodiments, the nucleic acid molecules of the invention comprise additional non-coding sequences such as non-coding 3' and 5' sequences (including, e.g., regulatory sequences) that may be homologous or heterologous to the LPAAT gene.

Nucleic Acid Constructs

The invention also provides constructs comprising a nucleic acid sequence encoding an LPAAT and/or a thioesterase that can further include one or more sequences that regulate or mediate transcription, translation, or integration of nucleotide sequences into a host genome. For example, the invention provides expression constructs that comprise one or more "expression control elements" or sequences that regulate expression transcription of an operably linked gene, or translation of the transcribed RNA. For example, an expression control element can be a promoter that may be operably linked to the gene of interest (e.g., an LPAAT gene) in an expression construct or "expression cassette." In some embodiments of the foregoing, the promoter is regulatable, e.g., inducible.

In embodiments where the nucleic acid construct does not contain a promoter in operable linkage with the nucleic acid sequence encoding the gene of interest (e.g., an LPAAT gene) the nucleic acid sequence can be transformed into the cells such that it becomes operably linked to an endogenous promoter by, e.g., homologous recombination, site specific integration, and/or vector integration. In some embodiments, genomic host sequences included in a nucleic acid construct for mediating homologous recombination into the host genome can include gene regulatory sequences, for example, a promoter sequence, that can regulate expression of an LPAAT gene of the nucleic acid construct. In such embodiments, the transgene(s) of the construct can become operably linked to a promoter that is endogenous to the host microorganism. In some embodiments, the endogenous promoter(s) are regulatable, e.g., inducible.

A promoter operably linked to a nucleic acid sequence encoding an LPAAT may be a promoter that is heterologous with respect to the LPAAT gene. In some embodiments of the foregoing invention, the promoter may be an inducible promoter, i.e., a promoter that mediates transcription of an operably linked gene in response to a particular stimulus. Such promoters may be advantageous, e.g., to minimize any deleterious effects on the growth of the host cell and/or to maximize production of the fatty acid product. An inducible promoter can be responsive to, e.g., light or dark or high or low temperature, and/or can be responsive to specific compounds. The inducible promoter may be, an ara promoter, a lac promoter, a trp promoter, a tet promoter (e.g., U.S. Pat. No. 5,851,796), a hybrid promoter that includes a portion of a trp, lac, or tet promoter, a hormone-responsive promoter (e.g., an ecdysone-responsive promoter, such as described in U.S. Pat. No. 6,379,945), a metallothionien promoter (e.g., U.S. Pat. No. 6,410,828), a pathogenesis-related (PR) promoter that can be responsive to a chemical such as, for example, salicylic acid, ethylene, thiamine, and/or BTH (U.S. Pat. No. 5,689, 044), or the like, or some combination thereof. An inducible promoter can also be responsive to light or dark (U.S. Pat. No. 5,750,385, U.S. Pat. No. 5,639,952), metals (Eukaryotic Cell 2:995-1002 (2003)) or temperature (U.S. Pat. No. 5,447,858; Abe et al. Plant Cell Physiol. 49: 625-632 (2008); Shroda et al. *Plant J.* 21: 121-131 (2000)). The foregoing list is exemplary and not limiting. The promoter sequence can be from any organism, provided that it is functional in the host organism. In certain embodiments, inducible promoters are formed by fusing one or more portions or domains from a known inducible promoter to at least a portion of a different promoter that can operate in the host cell, e.g. to confer inducibility on a promoter that operates in the host species.

For transformation of cyanobacteria, a variety of promoters that function in cyanobacteria can be utilized, including, but not limited to, the ara, lac, tac, and trc promoters, as well as derivatives that are also inducible by the addition of isopropyl β-D-1-thiogalactopyranoside (IPTG) such as the trcY or trcE promoter. Other promoters that may find use in the invention include promoters that are naturally associated with transposon- or bacterial chromosome-borne antibiotic resistance genes (e.g., neomycin phosphotransferase, chloramphenicol acetyltransferase, spectinomycin adenyltransferase, or the like, or combinations thereof), promoters associated with various heterologous bacterial and native cyanobacterial genes, promoters from viruses and phages, synthetic promoters, or the like, or combinations thereof. For example, the promoter(s) can be selected from prokaryotic promoters from a range of species, including eubacterial and cyanobacterial species, such as, for example, an araC or pBAD promoter, a rha promoter, a Pm promoter, a xylS promoter, a nir promoter, a nar promoter, a pho promoter, a tet promoter, a cys promoter, a metallothionien promoter, an ftf promoter, a gln promoter, a heat shock promoter, a cold-inducible promoter or a viral promoter. The foregoing promoters are exemplary and are not limiting. Promoters isolated from cyanobacteria that can be used can include but are not limited to the following: nrs (nickel-inducible), secA (secretion; controlled by the redox state of the cell), rbc (*Rubisco operon*), psaAB (PS I reaction center proteins; light regulated), psbA (Dl protein of PSII; light-inducible), and the like, and combinations thereof. In some embodiments, the promoters are regulated by nitrogen compounds, such as, for example, nar, ntc, nir or nrt promoters. In some embodiments, the promoters are regulated by phosphate (e.g., pho or pst promoters) or metals, e.g., the nrs promoter (Liu and Curtis (2009) *Proc Natl Acad Sciences USA* 106: 21550-21554), or the petE promoter (Buikema and Haselkorn (2001) *Proc Natl Acad Sciences USA* 98: 2729-2734)). Inducible promoters, as used in the constructs of the present invention, can use one or more portions or domains of the aforementioned promoters and/or other inducible promoters fused to at least a portion of a different promoter that can operate in the host organism, e.g., to confer inducibility on a promoter that operates in the host species.

Likewise, a wide variety of transcriptional terminators can be used for expression vector construction. Examples of possible terminators can include, but are not limited to, psbA, psaAB, rbc, secA, T7 coat protein, and the like, and combinations thereof.

In some embodiments, an isolated or recombinant nucleic acid molecule of the invention can comprise both a nucleic acid sequence that encodes an LPAAT and a nucleic acid sequence that encodes a thioesterase. The nucleic acid sequences encoding the LPAAT and the thioesterase may be, for example, any of the nucleic acid sequences described herein.

In certain embodiments, the nucleic acid sequence that encodes an LPAAT and the nucleic acid sequence that encodes a thioesterase can be operably linked to the same promoter and/or enhancer. For example, in particular embodiments the two genes (encoding an LPAAT and a thioesterase) may be organized as an operon, in which, for example, a promoter sequence is followed, in the 5' to 3' direction, by a thioesterase-encoding sequence and then an LPAAT-encoding sequence. In an alternative configuration of the operon, a promoter sequence is followed, in the 5' to 3' direction, by an LPAAT-encoding sequence and then a thioesterase-encoding sequence. In some embodiments, an isolated nucleic acid molecule can include two or more genes arranged in tandem, where the isolated nucleic acid molecule does not include a promoter sequence that operates in the intended host microorganism upstream of the two or more genes. In these embodiments, the promoterless operon can be designed for integration (e.g., homologous recombination) into a site of the host genome that may include a promoter sequence, such that the synthetic operon can be transcriptionally regulated by a promoter in the genome of the host microorganism. Further, the operon may be designed for integration (e.g., homologous recombination) into a site of the host genome that may include an enhancer sequence, such that the introduced operon can be transcriptionally regulated by an enhancer in the genome of the host microorganism. In any of the above embodiments of operons that include LPAAT and thioesterase genes, one or more additional regulatory sequences can be included in the isolated nucleic acid molecule, for example, a sequence for enhancing translation can be included upstream of any of the gene-encoding sequences, and/or a transcriptional terminator can optionally be included at or near the 3' end of the synthetic operon.

In addition to an LPAAT gene and a thioesterase gene, one or more additional genes can optionally be included in a synthetic operon as provided herein, where the one or more additional genes may include, for example, one or more genes encoding enzymes or proteins of the fatty acid synthesis pathway and/or one or more genes encoding enzymes or proteins that may enhance fatty acid product synthesis, one or more genes that may enhance photosynthesis or carbon-fixation, and/or one or more reporter genes or selectable markers.

In some embodiments, the nucleic acid sequence that encodes an LPAAT and the nucleic acid sequence that encodes a thioesterase can be provided on the same nucleic acid construct where they are operably linked to different promoters and/or transcriptional enhancers. The promoters and enhancers may be, e.g., any of the promoters and transcriptional enhancers described herein.

In certain embodiments, the vector comprising a nucleic acid sequence encoding an LPAAT is designed for transformation into cyanobacteria. In a particular embodiment, the vector permits homologous recombination of the LPAAT-encoding sequence with the cyanobacterial genome.

An isolated nucleic acid molecule of the present invention can include the sequences disclosed herein that encode an LPAAT or other polypeptide in a vector, such as, but not limited to, an expression vector. A vector can be a nucleic acid that has been generated via human intervention, including by recombinant means and/or direct chemical synthesis, and can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism. A vector can be an expression vector that includes one or more specified nucleic acid "expression control elements" that permit transcription and/or translation of a particular nucleic acid in a host cell. The vector can be a plasmid, a part of a plasmid, a viral construct, a nucleic acid fragment, or the like, or a combination thereof.

The vector can be a high copy number vector, a shuttle vector that can replicate in more than one species of cell, an expression vector, an integration vector, or a combination thereof. Typically, the expression vector can include a nucleic acid comprising a gene of interest operably linked to a promoter in an "expression cassette," which can also include, but is not limited to, a transcriptional terminator, a ribosome binding site, a splice site or splicing recognition sequence, an intron, an enhancer, a polyadenylation signal, an internal ribosome entry site, and similar elements. According to some embodiments, the present invention can involve recombinant microorganisms transformed with an isolated nucleic acid comprising a gene of interest under control of a heterologous promoter. Alternatively, if the vector does not contain a promoter operably linked with an isolated nucleic acid comprising a gene of interest, the isolated nucleic acid can be transformed into the microorganisms or host cells such that it becomes operably linked to an endogenous promoter by homologous recombination, site specific integration, and/or vector integration.

In some embodiments, the present invention additionally provides recombinant microorganisms or host cells transformed with an isolated nucleic acid comprising a gene of interest that is operably linked to one or more expression control elements. In some instances, it can be advantageous to express the protein at a certain point during the growth of the recombinant microorganism, e.g., to minimize any deleterious effects on the growth of the recombinant microorganism and/or to maximize production of the fatty acid product of interest. In such instances, one or more exogenous genes introduced into the recombinant microorganism or host cell can be operably linked to an inducible promoter, which mediates transcription of an operably linked gene in response to a particular stimulus.

Transformation vectors can additionally or alternately include a selectable marker, such as, but not limited to, a drug resistance gene, an herbicide resistance gene, a metabolic enzyme and/or factor required for survival of the host (for example, an auxotrophic marker), or the like, or a combination thereof. Transformed cells can be selected based upon the ability to grow in the presence of the antibiotic and/or other selectable marker under conditions in which cells lacking the resistance cassette or auxotrophic marker could not grow. Further, a non-selectable marker may be present on a vector, such as a gene encoding a fluorescent protein or enzyme that generates a detectable reaction product.

A vector comprising an isolated nucleic acid comprising a gene of interest can also be an integration vector that includes one or more sequences that promote integration of the gene of interest or a gene expression cassette into the genome of the host microorganism or host cell. For example, an integration vector used to transform cyanobacteria can include at least one sequence of at least 50, at least 100, at least 200, at least 300, at least 400, at least 500, or at least 600 nucleotides with homology to a sequence in the genome of the host organism to allow integration of the gene of interest or gene expression cassette into the genome of the host microorganism or host cell to occur via homologous recombination. In some examples, the gene or gene expression cassette is flanked by sequences homologous to a region of the host chromosome to promote integration of the gene of interest or gene expression cassette into the host chromosome. Alternatively or in addition, an integration vector can include one or more sequences that promote site-specific recombination or random integration such as, but not limited to, sequences recognized by recombinases, integrases, or transposases. In some embodiments, the integration vector can further include a gene encoding a recombinase, integrase, or transposase.

Transformation of Microorganisms and Host Cells

A vector comprising an isolated nucleic acid comprising a gene of interest can be introduced into cyanobacteria via conventional transformation and/or transfection techniques. The terms "transformation," "transfection," "conjugation," and "transduction," as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2010), Cold Spring Harbor Laboratory Press.

Host cells such as plants for use in the invention can be transformed by any feasible means, including, without limitation, the use of *Agrobacterium*, particle gun-mediated transformation, laser-mediated transformation, or electroporation. Algae and photosynthetic bacteria can be transformed by any suitable methods, including, as nonlimiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) *Proc. Natl. Acad. USA* 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017) electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly (amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation can also be performed on algal cells, for example after removing or wounding the algal cell wall (e.g., WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 355-307; Doestch et al. (2001) *Curr. Genet.* 39: 49-60; U.S. Pat. No. 7,294,506; WO 2003/091413; WO 2005/005643; and WO 2007/133558, all incorporated herein by reference in their entireties).

Methods of Producing Fatty Acid Products

The invention encompasses methods of producing a fatty acid product by culturing the recombinant microorganisms and host cells described herein, under conditions in which at least one fatty acid product is produced. The methods can further comprise isolating at least one fatty acid product. In some embodiments, at least a portion of the fatty acid and/or fatty acid derivative produced by the recombinant microorganisms is released or secreted into the growth media by the microorganism. In some embodiments, the expression of a polypeptide encoded by the nucleic acid molecules described herein can be induced in the recombinant microorganism to produce the fatty acid product.

Releasing and secreting, as used herein in the context of products of the invention, are used interchangeably to refer to a process by which active and/or passive transport mechanisms allow products of the invention to cross the cell membrane to exit the cell. Examples of such transport mechanisms can include, but are not limited to, gradient diffusion, facilitated diffusion, active transport, and combinations thereof.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. Non-limiting examples of selected and/or controlled conditions can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown heterotrophically, using a reduced carbon source, or mixotrophically, using both light and a reduced carbon source. Additionally or alternately, the microorganism or host cell can be cultured phototrophically. When growing phototrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. If an organic carbon molecule or compound is provided in the culture medium of a microorganism grown phototrophically, it generally cannot be taken up and/or metabolized by the cell for energy and/or typically is not present in an amount sufficient to provide sustainable energy for the growth of the cell culture. However, organic carbon molecules can be used by microorganisms growing heterotrophically. Thus, the present invention includes a process for converting a carbon source to a fatty acid product comprising contacting the carbon source with a recombinant microorganism or host cell of the invention. In some aspects the carbon source is an inorganic carbon source and in other aspects the carbon source is an organic carbon source.

Microorganisms and host cells that can be useful in accordance with the methods of the present invention can be found in various locations and environments throughout the world. Without wishing to be bound by theory, it is observed that, perhaps as a consequence of their isolation from other species and their evolutionary divergence, the particular growth medium for optimal growth and generation of lipid and/or other hydrocarbon constituents can vary. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (available on the world wide web at www.sbs.utexas.edu/utex/media.aspx) (visited Sep. 20, 2011); Culture Collection of Algae and Protozoa (available on the world wide web at www.ccap.ac.uk) (visited Sep. 20, 2011); and Katedra Botaniky (available on the world wide web at botany.natur.cuni.cz/algo/caup-media.html) (visited Sep. 20, 2011).

In some embodiments, media used for culturing an organism that produces fatty acids can include an increased concentration of a metal (typically provided as a salt and/or in an ionic form) such as, for example, sodium, potassium, magnesium, calcium, strontium, barium, beryllium, lead, iron, nickel, cobalt, tin, chromium, aluminum, zinc, copper, or the like, or combinations thereof (particularly multivalent metals, such as magnesium, calcium, and/or iron), with respect to a standard medium formulation, such as, for example, standard BG-11 medium (ATCC Medium 616, Table 5), or a modified medium such as ATCC Medium 854 (BG-11 modified to contain vitamin B12) or ATCC Medium 617 (BG-11 modified for marine cyanobacteria, containing additional NaCl and vitamin B12).

For example, a medium used for growing microorganisms that produce free fatty acids can include at least 2-fold, for example at least 3-fold, at least 4-fold, at least 5-fold, at least 6-fold, at least 7-fold, at least 8-fold, at least 9-fold, at least 10-fold, between 2-fold and 10-fold, and/or between 10-fold and 100-fold the amount of metal (e.g., calcium) as compared to a standard medium. The medium used for growing microorganisms that can produce free fatty acids can include, for example, at least 0.5 mM, between about 0.5 mM and about 1 mM, between about 1 mM and about 2 mM, between about 2 mM and about 5 mM, between about 5 mM and about 10 mM, between about 10 mM and about 25 mM, and greater than 25 mM metal (e.g., calcium) in the formulation.

In further embodiments, by using the excess amount of metal (e.g., calcium) in the medium, at least a portion of the fatty acid(s) can be sequestered as soap precipitates, which may result in decreasing the toxic effects of free fatty acid(s). Addition of metal (e.g., calcium) in the medium can additionally or alternately increase the tolerance of microorganism in media with a relatively high concentration of free fatty acids. Additionally or alternately, fatty acid-producing strains can advantageously be more robust with excess metal (e.g., calcium) content. Although the excess component is described herein as a metal, it is contemplated that the component can more generally be described as a carboxylate counterion source, for example a soap-forming counterion source, a metal ion source (noted as "metal" herein), a multivalent (i.e., having a valence of +2 or higher) counterion source, a divalent counterion source, or some combination thereof. Other details regarding this metal/carboxylate counterion source are described in the co-pending, commonly-assigned U.S. patent application Ser. No. 13/324,636, entitled "Culturing a Microorganism in a Medium with an Elevated Level of a Carboxylate Counterion Source", filed on Dec. 13, 2011.

The culture methods can include inducing expression of a particular gene described herein for the production of fatty acid products, and/or regulating metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the recombinant microorganisms or host cells can be cultured in a bioreactor. "Bioreactor" refers to an enclosure or partial enclosure in which cells are cultured, optionally in suspension and, when suspended, preferably in an aqueous liquid. The bioreactor can be used to culture microalgal cells through the various phases of their physiological cycle. Bioreactors can offer many advantages for use in heterotrophic growth and propagation methods. To produce biomass for use as food, microorganisms or host cells are preferably fermented in large quantities in liquid, such as in suspension cultures as an example. Bioreactors such as steel fermentors can accommodate very large culture volumes (40,000 liter and greater capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Microorganisms and host cells can additionally or alternately be cultured in a bioreactor equipped with an artificial light source, a "photobioreactor", and/or can have one or more walls that is transparent enough to light, including sunlight, to enable, facilitate, and/or maintain acceptable microorganism growth. For production of fatty acid products, photosynthetic microorganisms or host cells can additionally or alternately be cultured in shake flasks, test tubes, vials, microtiter dishes, petri dishes, or the like, or combinations thereof.

Additionally or alternately, recombinant photosynthetic microorganisms or host cells may be grown in ponds, canals, sea-based growth containers, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pretreat such sources such that the CO level introduced into the (photo)bioreactor do not constitute a dangerous and/or lethal dose with respect to the growth and/or survival of the microorganisms.

The methods include culturing a recombinant microorganism, such as a photosynthetic microorganism, such as, for example, a *cyanobacterium*, that includes a protein(s) as described herein to produce at least one fatty acid product, in which the method results in production of at least 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%, 300%, 400%, 500%, 600%, 700%, 800%, 900%, or 1000% more than the amount of the fatty acid product produced by an otherwise identical microorganism not including the protein(s), cultured under identical conditions. Additionally or alternatively, the methods include producing at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, at least 260 mg, at least 270 mg, at least 280 mg, at least 290 mg, at least 300 mg, at least 310 mg, at least 320 mg, at least 330 mg, at least 340 mg, at least 350 mg, at least 360 mg, at least 370 mg, at least 380 mg, at least 390 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, per liter of culture of a fatty acid product by culturing the recombinant microorganisms described herein. Although many times the goal can be to produce and/or recover as much fatty acid product as possible, in some instances the amount of the fatty acid product produced and/or recovered by the method described herein can be limited to 600 mg or less per liter of culture, for example to 550 mg or less per liter of culture, or to 500 mg or less per liter of culture.

Fatty acid products can be recovered from culture by recovery means known to those of ordinary skill in the art, such as by whole culture extraction, for example, using organic solvents. In some cases, recovery of fatty acid products can be enhanced by homogenization of the cells. When fatty acid products are sufficiently released or secreted from the microorganisms into the culture medium, the recovery method can be adapted to efficiently recover only the released fatty acid products, only the fatty acid products produced and stored within the microorganisms, or both the produced and released fatty acid products.

Fatty acid products secreted/released into the culture medium by the recombinant microorganisms described above can be recovered in a variety of ways. A straightforward isolation method, e.g., by partition using immiscible solvents, may be employed. Additionally or alternately, particulate adsorbents can be employed. These can include lipophilic particulates and/or ion exchange resins, depending on the design of the recovery method. They may be circulating in the separated medium and then collected, and/or the medium may be passed over a fixed bed column, for example a chromatographic column, containing these particulates. The fatty acid products can then be eluted from the particulate adsorbents, e.g., by the use of an appropriate solvent. In such circumstances, one isolation method can include carrying out evaporation of the solvent, followed by further processing of the isolated fatty acid products, to yield chemicals and/or fuels that can be used for a variety of commercial purposes.

In some embodiments of the methods described herein, the level of a fatty acid product, for example a C8-C24 fatty acid, a C12-C24 fatty acid, or a C12-C18 fatty acid, such as, for example, at least one of a C12, C14, C16, and/or a C18 fatty acid, can be increased in the culture with respect to a culture of an otherwise identical microorganism or host cell, but lacking the genetic modifications of the invention.

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

Additionally or alternatively, the present invention can include one or more of the following embodiments.

Embodiment 1

A recombinant microorganism comprising a non-native nucleic acid sequence encoding a thioesterase and a non-native nucleic acid sequence encoding a lysophosphatidic acid acyltransferase (LPAAT), wherein the recombinant microorganism produces at least one free fatty acid or at least one fatty acid derivative, wherein the LPAAT and the thioesterase have different acyl substrate preferences.

Embodiment 2

The recombinant microorganism of embodiment 1, wherein the thioesterase and the LPAAT have complementary acyl-ACP substrate preferences, preferably wherein the LPAAT has a substrate preference for an acyl-ACP substrate having a longer acyl chain length than an acyl chain length of a preferred substrate of the thioesterase.

Embodiment 3

The recombinant microorganism of embodiment 1, wherein any of the following are satisfied: the thioesterase has a substrate preference for one or more acyl substrates having acyl chain lengths of C12, C14, and/or C16, and the LPAAT has a substrate preference for substrates having a C18 acyl chain length; the thioesterase has a substrate preference for one or more acyl substrates having acyl chain lengths of C12 and C14 and the LPAAT has a substrate preference for substrates having a C16 or C18 acyl chain length; the thioesterase has a substrate preference for one or more acyl substrates having acyl chain lengths of C12 and the LPAAT has a substrate preference for one or more substrates having a C14, C16, and/or C18 acyl chain length; and the thioesterase has a substrate preference for one or more acyl substrates having acyl chain lengths of C12, C14, C16, and/or C18, and the LPAAT has a substrate preference for substrates having a C20, C22, or C24 acyl chain length.

Embodiment 4

The recombinant microorganism of embodiment 1, wherein the thioesterase and the LPAAT have different acyl-ACP substrate preferences, wherein one or more of the following are satisfied: the LPAAT has a C16 acyl substrate preference, the LPAAT has a C18 substrate preference, the LPAAT is a prokaryotic LPAAT, the LPAAT is a eukaryotic LPAAT, the LPAAT is a microsomal LPAAT, the LPAAT is a plastidal LPAAT, the LPAAT is a cyanobacterial LPAAT.

Embodiment 5

The recombinant microorganism of any of embodiments 1-4, wherein the LPAAT has at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to SEQ ID NO:2, 3, 4, 5, 6, 7, 8, 9, 10, 11, 12, 13, 14, or 15; or the LPAAT has at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to SEQ ID NO:16 or 17; or the LPAAT has at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to SEQ ID NO:18, 19, 20, or 21; or the LPAAT has at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or about 100% identity to SEQ ID NO:22, 23, 24, 25, or 26.

Embodiment 6

The recombinant microorganism of any previous embodiment, wherein the thioesterase is an acyl-CoA thioesterase, a 4-hydroxybenzoyl thioesterase, or an acyl-ACP thioesterase, optionally a plant acyl-ACP thioesterase or a prokaryotic acyl-ACP thioesterase.

Embodiment 7

The recombinant microorganism of any previous embodiment, wherein any of the following are satisfied: the non-native nucleic acid sequence encodes an LPAAT that is homologous with respect to the recombinant microorganism, the non-native nucleic acid sequence encodes an LPAAT that is heterologous with respect to the recombinant microorganism, the non-native nucleic acid sequence encoding the LPAAT is operably linked to a heterologous promoter, the non-native nucleic acid sequence encoding the acyl-ACP thioesterase is operably linked to a heterologous promoter, one or both of the non-native nucleic acid sequence encoding the acyl-ACP thioesterase and the non-native nucleic acid sequence encoding the LPAAT are operably linked to an inducible promoter, the non-native nucleic acid sequence encoding the acyl-ACP thioesterase and the non-native nucleic acid sequence encoding the LPAAT are operably linked to the same promoter or to copies of the same promoter.

Embodiment 8

A recombinant microorganism, according to any of the following: the microorganism comprises a non-native gene encoding an LPAAT having at least 85% identity to SEQ ID NO:2, or to a cyanobacterial ortholog thereof and a non-native gene encoding an acyl-ACP thioesterase having at least 85% identity to SEQ ID NO:44, SEQ ID NO:54, SEQ ID NO:55, SEQ ID NO:56, or SEQ ID NO:57; or the microorganism comprises a non-native gene encoding an LPAAT having at least 85% identity to SEQ ID NO:22, 23, 24, 24, or 26, and a non-native gene encoding an acyl-ACP thioesterase having at least 85% identity to SEQ ID NO:26, SEQ ID NO:54, SEQ ID NO:55, SEQ ID NO:56, or SEQ ID NO:57;

wherein the microorganism produces at least one free fatty acid or at least one fatty acid derivative;

preferably wherein the microorganism is a *cyanobacterium*.

Embodiment 9

The recombinant microorganism of any one of embodiments 1-8, wherein the recombinant microorganism further comprises a construct for downregulating the expression of an endogenous acyl-ACP synthetase gene or an acyl-CoA synthetase gene, wherein the construct is an antisense construct, a micro RNA construct, a ribozyme construct, or a gene disruption construct.

Embodiment 10

The recombinant microorganism of any one of embodiments 1-9, wherein the recombinant microorganism further comprises a construct for downregulating the expression of an endogenous acyl-ACP synthetase gene or an acyl-CoA synthetase gene, wherein the construct is an antisense RNA construct, a microRNA construct, or a ribozyme construct.

Embodiment 11

A recombinant microorganism according to any of the previous embodiments, wherein the recombinant microorganism further includes one or more additional exogenous or non-native genes encoding one or more of an acyl-CoA synthetase, an acyl-CoA reductase, an acyl-ACP reductase, a carboxylic acid reductase, a fatty aldehyde reductase, a fatty aldehyde decarbonylase, a fatty acid decarboxylase, a wax synthase, and an acyltransferase, wherein the microorganism produces at least one fatty acid derivative, preferably wherein the fatty acid derivative is a fatty alcohol, a wax ester, an alkane, or an alkene.

Embodiment 12

A recombinant microorganism according to any of the previous embodiments, wherein the recombinant microorganism further includes one or more additional exogenous or non-native genes encoding one or more of an a beta-ketoacyl synthetase, an acetyl-CoA carboxylase, a malonyl CoA:ACP transacylase, or an acyl carrier protein.

Embodiment 13

The recombinant microorganism of any one of embodiments 1-12, wherein the recombinant microorganism is a photosynthetic microorganism, optionally wherein the photosynthetic microorganism is a *cyanobacterium* or a microalga.

Embodiment 14

The recombinant microorganism of embodiment 13, wherein the cyanobacterium is *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema* or *Xenococcus*.

Embodiment 15

The recombinant microorganism of embodiment 13, wherein the microalga is an *Achnanthes, Amphiprora,*

*Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thraustochytrium, Viridiella*, or *Volvox* species.

Embodiment 16

The recombinant microorganism of any one of embodiments 1-12, wherein the recombinant microorganism is a bacterium, fungus, or heterokont, optionally wherein the recombinant microorganism is a species of *Acetobacter, Acinetobacter, Arthrobacter, Bacillus, Brevibacterium, Chromatium, Chlorobium, Clostridium, Corynebacterium, Deinococcus, Delftia, Desulfovibrio, Enterococcus, Escherichia, Kineococcus, Klebsiella, Lactobacillus, Lactococcus, Micrococcus, Mycobacterium, Jeotgalicoccus, Paenibacillus, Propionibacter, Pseudomonas, Rhodopseudomonas, Rhodobacter, Rhodococcus, Rhodospirillium, Rhodomicrobium, Salmonella, Serratia, Shewanella, Stenotrophomonas, Streptomyces, Streptococcus, Vibrio, Zymomonas, Aspergillus, Candida, Cryptococcus, Trichoderma, Neurospora, Endomycopsis, Fusarium, Humicola, Rhizomucor, Rhodotorula, Kluyveromyces, Pichia, Lipomyces, Mucor, Myceliophtora, Penicillium, Phanerochaete, Chrysosporium, Saccharomyces, Schizosaccharomyces, Yarrowia, Schizochytrium*, or *Thraustochytriales*.

Embodiment 17

The recombinant microorganism of any one of embodiments 1-16, wherein the recombinant microorganism produces: at least 10%, at least 20%, at least 25%, at least 30%, at least 40%, at least 50%, or at least 60% more fatty acid product compared to an otherwise identical microorganism lacking the second nucleic acid.

Embodiment 18

The recombinant microorganism of embodiment 16, wherein the fatty acid product is one or more of a fatty acid, a fatty aldehyde, a fatty alcohol, a fatty acid ester, a wax ester, or a hydrocarbon.

Embodiment 19

The recombinant microorganism of embodiment 18, wherein the fatty acid product is a C8-C24 fatty acid product, preferably a C12-C18 fatty acid product or a C12-C16 fatty acid product, optionally wherein the fatty acid product is saturated.

Embodiment 20

A method of producing a fatty acid product comprising culturing the recombinant microorganism of any one of embodiments 1-19 under conditions in which at least one fatty acid product is produced, wherein the fatty acid product is one or more of a fatty acid, a fatty aldehyde, a fatty alcohol, a fatty acid ester, a wax ester, or a hydrocarbon, wherein the fatty acid product is preferably a C12-C24 fatty acid product, more preferably a C12-C18 fatty acid product, or more preferably a C12-C18 fatty acid product, wherein the fatty acid product is saturated or unsaturated.

Embodiment 21

The method of embodiments 20, further wherein at least a portion of the fatty acid product is secreted into the medium, preferably wherein the fatty acid product is isolated from the culture medium.

Embodiment 22

The method of claim 20 or 21, wherein the recombinant microorganism is a photosynthetic microorganism, wherein the photosynthetic microorganism is cultured photoautotrophically, preferably wherein the culture medium does not include a substantial amount of reduced carbon, optionally wherein the culture medium includes inorganic carbon, optionally wherein the inorganic carbon is $CO_2$ or carbonate.

Embodiment 23

The method of any of embodiments 20-22, wherein expression of one or both of the non-native nucleic acid sequence that encodes an LPAAT and the non-native nucleic acid sequence encodes a thioesterase is induced.

Embodiment 24

The method of any one of embodiments 20-23, wherein at least one fatty acid product produced by the recombinant microorganism is a C8-C24 fatty acid, fatty alcohol, or fatty aldehyde, preferably a C12-C18 fatty acid, fatty alcohol, or fatty aldehyde, or more preferably a C12-C16 fatty acid, fatty alcohol, or fatty aldehyde; or wherein at least one fatty acid product produced by the recombinant microorganism is a C16-C48 wax ester, preferably a C24-C36 wax ester, or more preferably a C24-C32 wax ester; or wherein the fatty acid product is a C11-C23 alkane or alkene, preferably a C11-C19 alkane or alkene, and more preferably a C11-C17 alkane or alkene.

Embodiment 25

A fatty acid product produced by the recombinant microorganism of any one of embodiments 1-19 or any of the methods of embodiments 20-24, wherein the fatty acid product is one or more of a fatty acid, a fatty aldehyde, a fatty alcohol, a fatty acid ester, a wax ester, or a hydrocarbon.

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

EXAMPLES

The invention as described above can be readily understood by reference to the following examples, which are included for purposes of illustration of certain aspects and embodiments of the present invention, and are not intended to limit the invention.

Example 1

Production of Free Fatty Acids in Reduced Feedback Inhibition Synechocystis sp. PCC6803 Strains While the invention is not bound by any one theory, the inventors hypothesized that C18:0 acyl-ACP, which is not a preferred substrate of the non-native Cc1FatB1 acyl-ACP thioesterase expressed in the cell, might accumulate in fatty acid-producing cells that express the C12-C16-preferring Cc1FatB1 acyl-ACP thioesterase, possibly limiting fatty acid production by feedback inhibition, and that overexpressing a C18-preferring LPAAT gene might limit any inhibitory effects by reducing the C18:0 acyl-ACP pool through LPAAT-catalyzed condensation of C18:0 acyl-ACP with lysophosphatidic acid to generate phosphatidic acid. See, e.g., FIG. 1. In addition to limiting feedback inhibition of fatty acid synthesis, the inventors considered the modification might help to stabilize the cell membrane by promoting membrane lipid biosynthesis.

1.1. LPAAT Vector Construction

Figure 2:
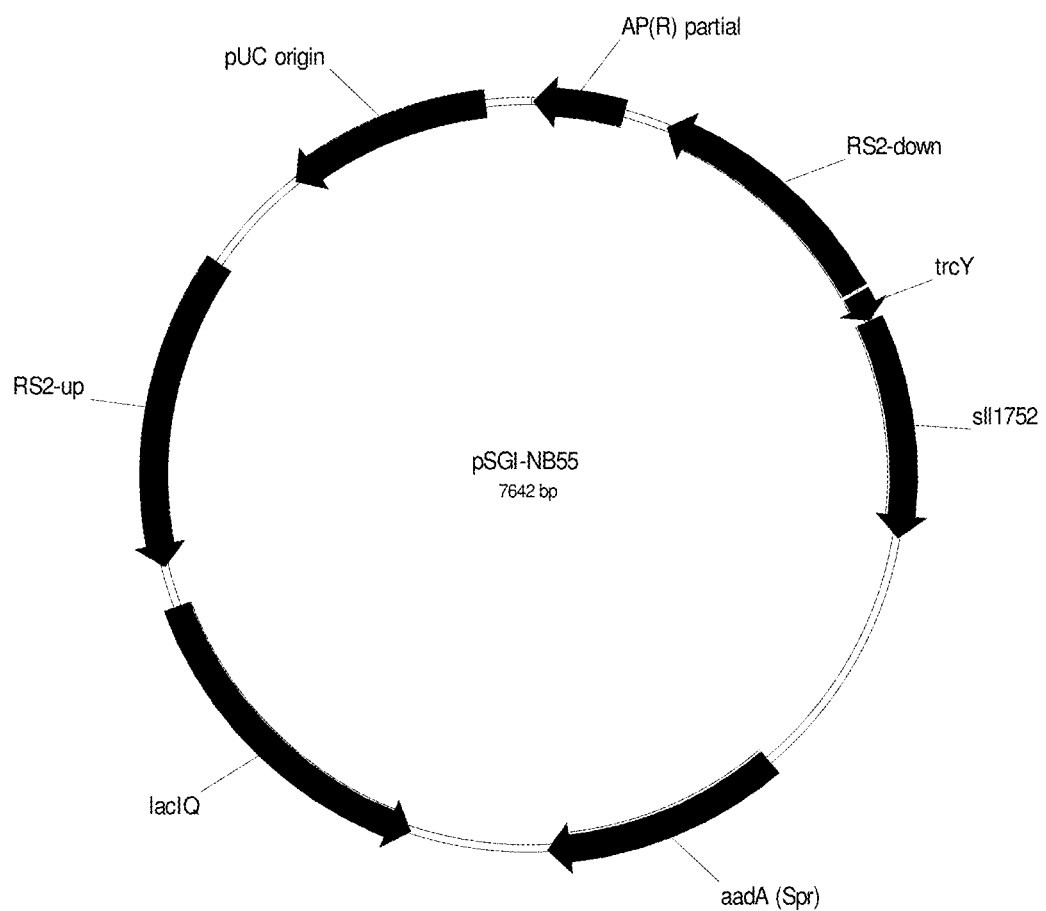
FIG. 2 is a schematic representation of an example of an integration vector that includes a nucleic acid sequence encoding an LPAAT (sll1752).

An expression construct was designed that included a gene encoding an LPAAT with a preference for C18:0 acyl-ACPs. The pSGI-NB55 vector (SEQ ID NO:27; FIG. 2) was constructed to overexpress the Lysophophatidic Acid Acyl Transferase (LPAAT) gene sll1752 (Genbank Accession Number, Gene ID; SEQ ID NO:1) from Synechocystis sp. PCC 6803 using a trcY promoter (SEQ ID NO:28). The sll1752 gene was amplified from genomic Synechocystis DNA using primers NB395 (SEQ ID NO:29) and NB396 (SEQ ID NO:30) which contained approximately 15 bp sequence overlap with cyanobacterial integration vector pSGI-YC63 (SEQ ID NO:31). pSGI-YC63 contained a spectinomycin marker for selection, homologous "RS2 up" (SEQ ID NO:32) and "RS2 down" (SEQ ID NO:33) arms for integration in the RS2 site of the Synechocystis sp. PCC 6803 genome, the lacIQ repressor for the trcY promoter (SEQ ID NO:28) to drive sll1752 expression, and a pUC origin of replication for propagation of the vector in E. Coli. The pSGI-YC63 vector (SEQ ID NO:31) was PCR amplified to produce a linearized nucleic acid molecule using primers NB393 (SEQ ID NO:34) and NB394 (SEQ ID NO:35). Purified PCR product for the vector backbone and the sll1752 gene was combined in E. coli using the Quick PCR Cloning Kit and propagated in Alpha-Select Gold E. Coli cells.

1.2. Thioesterase Cc1FatB1 Vector Construction

Figure 3:
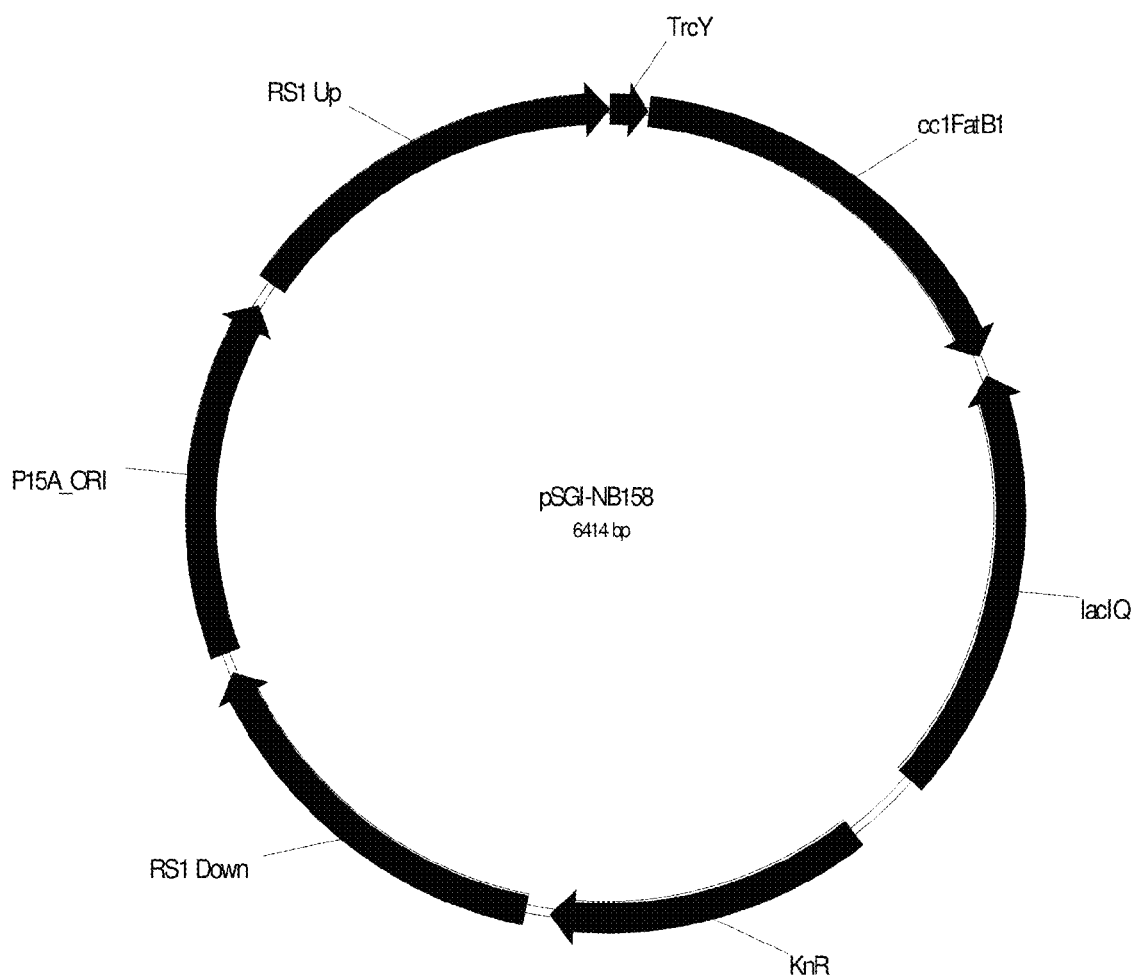
FIG. 3 is a schematic representation of an example of an integration vector that includes a nucleic acid sequence encoding an acyl-ACP thioesterase (Cc1FatB1).

A thioesterase gene from the higher plant Cuphea carthagenensis, Cc1FatB1 (US 2009/0298143; WO 2009/076559), was cloned into a vector designed for promoting gene integration into the RS1 site of the Synechocystis sp. PCC 6803 genome. The pSGI-NB158 acyl-ACP thioesterase construct (SEQ ID NO: 36; FIG. 3) contained a P15A origin of replication for propagation in E. coli, amplified from vector pACYC184 using primers NB470 (SEQ ID NO:37) and NB471 (SEQ ID NO:38); a kanamycin resistance marker for selection, amplified from cyanobacterial integration vector SGI-YC28 using primers NB466 (SEQ ID NO:39) and NB467 (SEQ ID NO:40), "RS1 up" (SEQ ID NO:41) and "RS1 down" (SEQ ID NO:42) fragments for homologous recombination in Synechocystis 6803, amplified using primers NB466 and NB467, respectively; the trcY promoter (SEQ ID NO:28), and a lacIQ repressor for the trcY promoter-driven Cuphea Cc1FatB1 thioesterase gene (SEQ ID NO:43) encoding an N-terminally truncated acyl-ACP thioesterase (SEQ ID NO:44) having a substrate preference for C12-C16 acyl-ACPs. Primers NB 462 (SEQ ID NO:45) and NB 463 (SEQ ID NO:46) were used to amplify the trcY-Cc1FatB1 thioesterase cassette from a prior expression vector. The lac IQ fragment was amplified using primers NB464 (SEQ ID NO:47) and NB 465 (SEQ ID NO:48) from another vector, and the kanamycin resistance gene was amplified using primers NB466 (SEQ ID NO:49) and NB467 (SEQ ID NO:50) from vector pSGI-YC28 (see Table 1). Primers were designed to include sequences that would be incorporated into the termini of the final PCR products such that the amplified fragments would have 10-20 bps terminal homology to nucleic acid fragments to be cloned adjacent to the fragments. Cloning was performed using the Quick PCR Cloning Kit (BPS Biosciences, San Diego). The clones were transformed and propagated in Alpha-Select Gold competent E. coli cells (Bioline, Tauton).

TABLE 1

Primers Used in Vector Construction

| PRIMER | SEQUENCE | SEQ ID NO: |
|---|---|---|
| NB460 | GTTTATCACAGTTAAATTATTGCTGAAGCGGAATCCCTGG | 58 |
| NB461 | CAGCCTCAGGCCATATAACCATCAAAGCCATAGTTGGC | 59 |
| NB462 | CTTTGATGGTTATATGGCCTGAGGCTGAAATGAGCTGTTGAC | 45 |
| NB463 | GATCTGAAGCTTGAAAGGTTATTAACTGGCGGGATTACCATTACTGG | 46 |
| NB464 | GTAATCCCGCCAGTTAATAACCTTTCAAGCTTCAGATCAATTCGCGC | 47 |
| NB465 | ATATTTTTATCTTGTGGTCCGGAATTCGCCCTTCTAAGC | 48 |
| NB466 | GGGCGAATTCCGGACCACAA-GATAAAAATATATCATCATGAACAATAAAACTGTCTG | 49 |
| NB467 | GGTGCCATCCATACCGGGCCGCCGTCCCGTCAAG | 50 |
| NB468 | GGGACGGCGGCCCGGTATGGATGGCACCGATG | 60 |
| NB469 | CCGTCAGTAGCTGAACATGGGGGACCATTCTCTGGATCATTG | 67 |
| NB470 | AGAGAATGGTCCCCCATGTTCAGCTACTGACGGGGTG | 37 |
| NB471 | GGATTCCGCTTCAGCAATAATTTAACTGTGATAAACTACCGCATTAAAGCTTATCG | 38 |
| NB1 | CTCGAGCCCCGTGCTATGACTAGC | 52 |
| NB9 | CTCGAGCCCGGAACGTTTTTTGTACCCC | 53 |
| NB87 | CAATTGGCATGCACCCCTATTTGTTTATTTTTCTAAATAC | 61 |
| NB88 | CAATTGGTTTAAACGGCCTAAGCTTTATGCTTGTAAACCGTTTTGTG | 62 |
| NB5 | GATCGACGTATAAACTGTCAACATATTTCTGCAAG | 63 |
| NB6 | CTCGAGTGTGGTGCCGGAGGTGTAG | 75 |
| NB393 | TTCTAGATATCTGCAGGCCTAAGCTTTATGC | 34 |
| NB394 | TTTTTTTCCTCCTTAGTGTGAAATTGTTATCCGC | 35 |
| NB395 | CACTAAGGAGGAAAAAAAATGACCAATTCTCCCCTGGCG | 29 |
| NB396 | CCTGCAGATATCTAGAATCACGAAGCGGCGATCG | 30 |

1.3. Acyl-ACP Synthetase Knockout Vector Construction

The pSGI-NB19 vector (SEQ ID NO:51) was used to knock out the slr1609 Acyl-ACP synthetase gene of *Synechocystis* sp. PCC 6803. Primers NB1 (SEQ ID NO:52) and NB9 (SEQ ID NO:53) were used to amplify the slr1609 gene fragment from *Synechocystis* sp. PCC 6803. This fragment was ligated into the TOPO vector PCR2.1 (Life Technologies, Carlsbad, Calif.) via the manufacturer's protocol, and the plasmid construct was propagated in TOP10 *E. Coli* cells (Life Technologies, Carlsbad, Calif.). This plasmid was cut with and MfeI restriction Enzyme (New England Biolabs, Ipswich, Mass.). The GmR fragment was PCR amplified from a pAW4 plasmid with primers NB87 and NB88 containing MfeI restrictions sites used to cut the ends of the PCR fragment. This was then ligated into the TOPO vector containing the slr1609 fragment from the previous step to create plasmid pSGI-NB19 (SEQ ID NO:51).

1.4. Production of Free Fatty Acids

Figure 4:
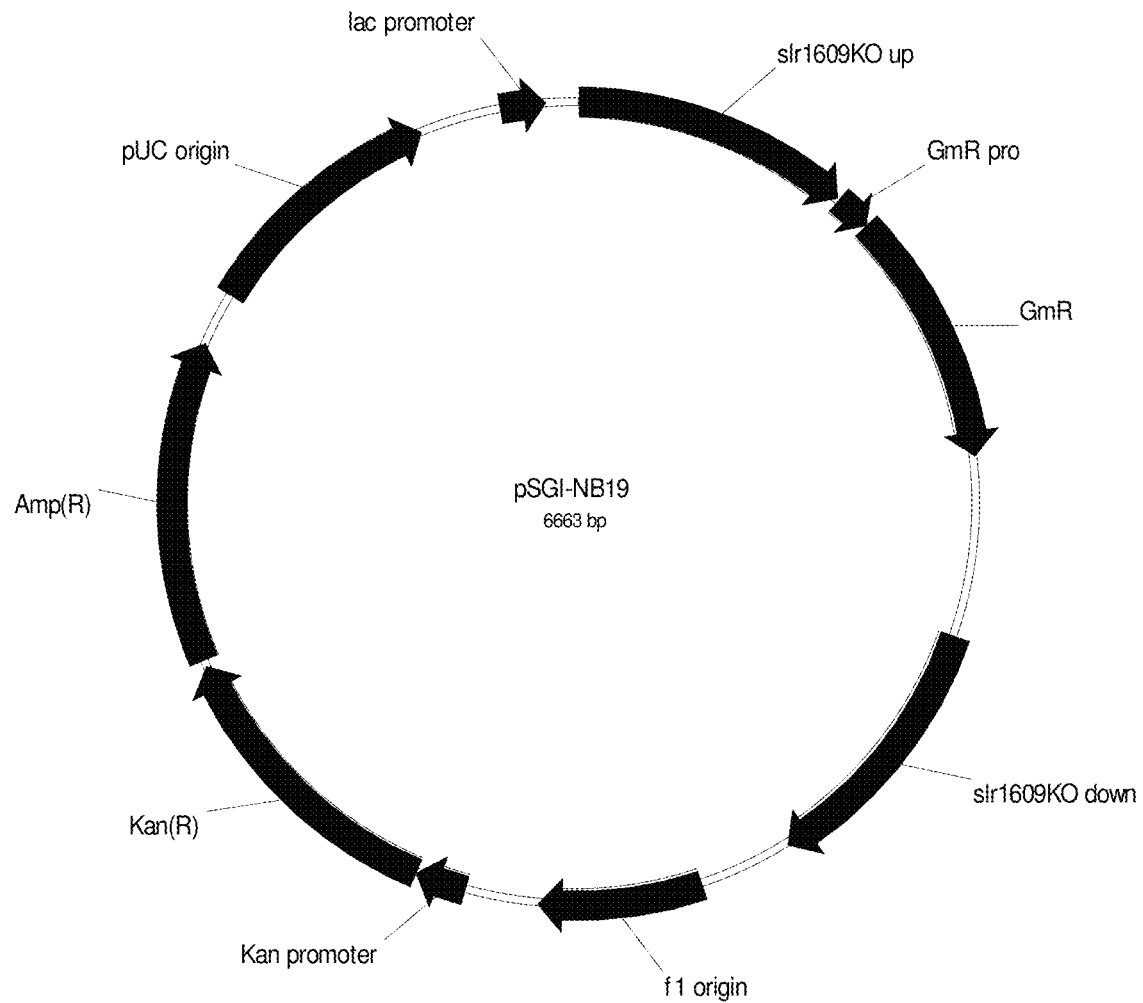
FIG. 4 is a schematic representation of an example of a vector for disrupting a gene encoding an acyl-ACP synthetase (slr1609).

*Synechocystis* sp. PCC 6803 was transformed with the pSGI-NB55 LPAAT gene expression construct (SEQ ID NO:27; FIG. 2), the pSGI-NB158 acyl-ACP thioesterase expression construct (SEQ ID NO: 36; FIG. 3), or the pSGI-NB19 acyl-ACP synthetase gene knock out (AAS KO) construct (SEQ ID NO:51; FIG. 4) or the combinations of pSGI-NB55 and pSGI-NB158 or pSGI-NB55 and pSGI-NB19 essentially according to Zang et al. (2007) *J. Microbiology* 45:241-245, the content of which is incorporated herein by reference in its entirety. Briefly, cells were grown under constant light to an optical density 730 (O.D.$_{730}$) of approximately 0.7 to 0.9 (an OD$_{730}$ of ~0.25 corresponds to ~1×10$^8$ cells/ml) and harvested by centrifugation at ~2,000 g for ~15 mins at room temperature (~20-25° C.). The cell pellet was resuspended in approximately 0.3 times the growth volume of fresh BG-11 medium and used immediately for transformation. About 1 microgram of plasmid DNA (containing pSGI-NB55 construct (SEQ ID NO:27) that included an LPAAT gene, or the pSGI-NB158 acyl-ACP thioesterase construct (SEQ ID NO:36), or the AAS knock out construct pSGI-NB19 (SEQ ID NO:51)) was added to ~0.3 ml of cells, gently mixed, and incubated approximately 5 hours with illumination at ~30° C. without agitation. Cells were spread on a filter (Whatmann Nuclepore Polycarbonate Track-Etched membrane, PC ~47 mm, ~0.2 micron) positioned on a ~50 ml BG-11 agar plates and allowed to recover for about 16 to 24 hours under light, after which the filter was lifted and placed on a fresh BG-11 plate containing spectinomycin (10 μg/ml) for selection of the LPAAT expression construct pSGI-NB55 (SEQ ID NO:27), kanamycin (10 μg/ml) for selection of the acyl-ACP thioesterase expression construct pSGI-NB158 (SEQ ID NO: 36), or gentamycin (5 μg/ml) for selection of the acyl-ACP synthetase knock out construct pSGI-NB 19 (SEQ ID NO:51) to select for transformants. Resulting colonies were screened further for the presence of the thioesterase genes by PCR using the primers used to generate the gene fragments.

TABLE 2

| BG-11 Medium | |
| --- | --- |
| NaNO$_3$ | 1.5 g |
| K$_2$HPO$_4$ | 0.04 g |
| MgSO$_4$ * 7H$_2$O | 0.075 g |
| CaCl$_2$ * 2H$_2$O | 0.036 g |
| Citric acid | 6.0 mg |
| Ferric ammonium citrate | 6.0 mg |
| EDTA | 1.0 mg |
| Na$_2$CO$_3$ | 0.02 g |
| Trace Metal Mix A5[#] | 1.0 ml |
| Agar (if needed) | (up to) 10.0 g |
| Distilled water | 1.0 L |

[#]Trace Metal Mix A5
H$_3$BO$_3$ 2.86 g
MnCl$_2$ * 4H$_2$O 1.81 g
ZnSO$_4$ * 7H$_2$O 0.22 g
Na$_2$MoO$_4$ * 2H$_2$O 0.39 g
CuSO$_4$ * 5H$_2$O 0.080 g
Co(NO$_3$)$_2$ * 6H$_2$O 49.4 mg
Distilled water to 1.0 L For production of fatty acids, patches of *Synechocystis* cells transformed with desired constructs (based on size selection using specific primers for PCR screening) were scraped and grown in 25 mL of BG-11 medium (ATCC 616, as shown in Table 2; component weights are approximate; final pH 7.1; autoclaved at about 121° C. for about 15 mins.) with appropriate antibiotics. Liquid cultures were grown in shake flasks at 30° C., ~65 μmol/m$^2$/s light, about 215 rpm with the supply of ~5% CO$_2$ until turbid (approximately 3 days). The O.D. (730 nm) of each culture was measured in order to determine the volume of BG-11 medium for resuspending the cells for production cultures. Resuspensions were performed to provide all cultures at or above O.D. 1.1 (730 nm). To ensure that the desired starting O.D. 1.1 (730 nm) for induction was achieved, cultures were spun down at 2,000 g for 10 minutes (20-25° C.) and resuspended in 9-10 mL BG-11 medium supplemented with 10 mg/mL BSA. O.D. readings were measured again after resuspension and diluted to O.D 1.1 (730 nm), again in BG-11 medium supplemented with 10 mg/mL BSA. BSA supplementation reduced fatty acid toxicity that could cause bleaching of the production cultures. Appropriate antibiotics were added to the cultures and the cells were induced with IPTG on day 1 in ~4 ml screw thread glass vials with gas permeable tape for sealing, growing at about 30° C., ~65 μmol/m$^2$/s light, shaking at about 215 rpm with a supply of ~5% CO$_2$. The BG-11 medium does not provide a reduced carbon source that can be used as an energy source for the growth of the cells. Rather, the cells were grown phototrophically using CO$_2$ as substantially the sole carbon source, using light as the energy sources, and incorporating carbon from CO$_2$ into biomolecules, including fatty acids. The final concentration of ~1 mM IPTG was added to all samples to induce the free fatty acid production. The whole vials were submitted for GC-free fatty acid analysis.

1.5. Analysis of free fatty acids

Free fatty acids were analyzed by gas chromatography with flame ion detection (GC-FID). About 1.0 mL of the *Synechocystis* cultures were added to ~4 mL glass GC vials with PTFE-lined caps (National Scientific). About eighty-four microliters of an internal standard (I.S.) set that included the free fatty acids C9:0, C13:0, and C17:0, each at about 600 μg/ml in hexane, were added to the culture sample followed by about 83 microliters of ~50% H$_2$SO$_4$, about 167 microliters of ~5M NaCl, and about 1.4 milliliters of hexane. The final concentration of each I.S. was about 50 μg/mL. The fatty acids for making the internal standard set were purchased either from Fluka or Nu Chek Prep. The cultures were then vortexed on a Multi-tube vortexer at about 2,500 rpm for about 30 minutes. The vials were finally centrifuged for about 3 minutes at about 2,000 rpm, in order to provide good separation between organic and aqueous phases. The hexane layer was analyzed by gas chromatography (GC).

*Synechocystis* fatty acid samples were analyzed on an Agilent model 7890A GC/FID that included a J&W Scientific DB-FFAP capillary column (~10 m length, ~0.10 mm internal diameter, ~0.10 μm film thickness). For analysis of cyanobacterial samples, the GC oven was programmed as follows: about 120° C. for about 0.1 minute, then heated at about 40° C./minute to about 240° C. (hold ~3.5 minutes). The injector temperature was kept at about 260° C., and a ~30:1 split ~0.9 μl injection was used. Helium was used as a carrier gas at a flow rate of about 0.599 mL/minute. The analytes were identified by comparison of retention times to individually injected standards. The calibration range for the analytes was about 2 μg/ml to about 200 μg/ml for C8:0-C16:1 fatty acids and about 0.625 μg/ml to about 50 μg/ml for C18:0-C18:3 fatty acids.

Figure 5:
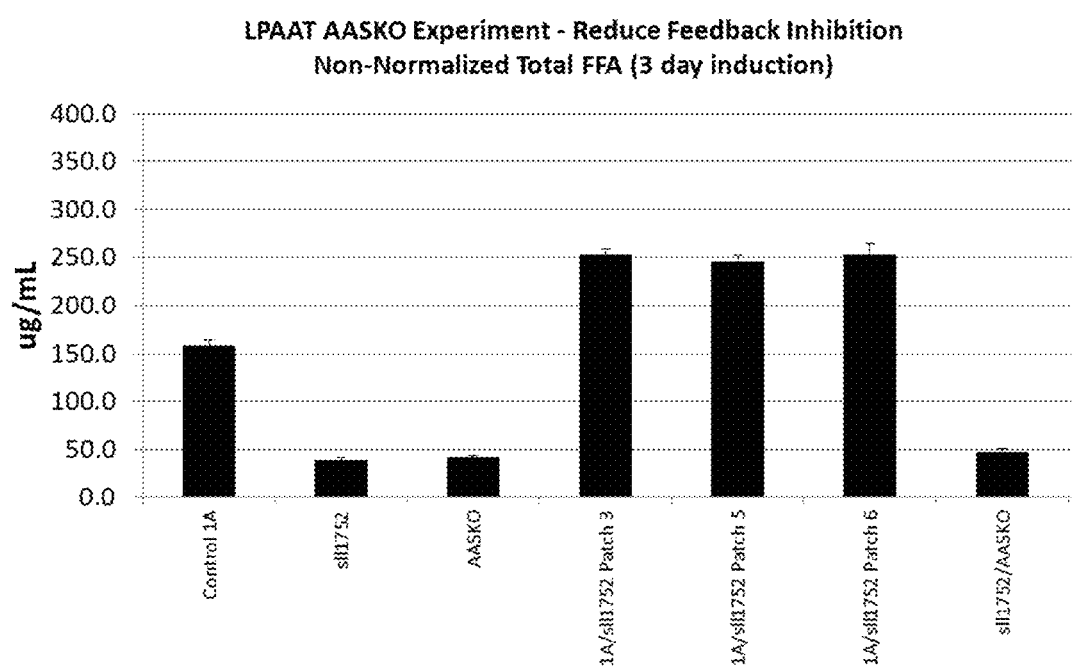
FIG. 5 is a graph depicting non-normalized total free fatty acid production (μg/mL) of *Synechocystis* sp. 6803 strains comprising (left to right) the Cc1FatB1 acyl-ACP thioesterase gene (Control 1A), the recombinant sll1752 gene encoding a C18:0 LPAAT (sll1752), an attenuated acyl-ACP synthetase gene (AASKO), followed by three separate clones (Patch 3, Patch 5, Patch 6) containing the Cc1FatB1 acyl-ACP thioesterase gene in combination with the inducible sll1752 gene (1A/sll1752), and finally the sll1752 LPAAT gene in combination with the attenuated acyl-ACP synthetase gene (AASKO).

As shown in FIG. 5, a 60% increase in total FFA production over the Cc1FatB1 thioesterase-containing strain (Control 1A) was detected for the combination Cc1FatB1 thioesterase and LPAAT-containing strain (sll1752). Over-expression of sll1752 alone, however, resulted in a greater than 3-fold drop in total FFA as compared to Control 1A. A similar drop in total FFA as compared to Control 1A was observed in strains with an attenuated acyl-ACP synthetase gene (AASKO) or a combination of sll1752 and AASKO.

FIG. 6 shows the chain lengths of the fatty acids produced by the strains expressing the acyl-ACP thioesterase Cc1FatB1 with and without expression of the sll1752 LPAAT. The substrate preference for C14 and C16, as well as C12 acyl substrates is clearly seen in the 1A control and is maintained in the strain that co-expressed the C18-preferring LPAAT gene; however the yield of free fatty acids is significantly increased.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant microorganism comprising a first non-native nucleic acid encoding an acyl-ACP thioesterase from a higher plant species or from a prokaryotic organism and a second non-native nucleic acid encoding a lysophosphatidic acid acyltransferase (LPAAT) from a prokaryotic organism, wherein the microorganism produces a fatty acid product, wherein the thioesterase and the LPAAT have complementary acyl-ACP substrate preferences, and wherein the complementary acyl-ACP substrate preferences are selected from the group consisting of: (1) the thioesterase has a substrate preference for one or more acyl substrates having an acyl chain length selected from the group consisting of C12, C14, and C16, and the LPAAT has a substrate preference for substrates having a C18 acyl chain length; (2) the thioesterase has a substrate preference for one or more acyl substrates having an acyl chain length of C12 and C14 and the LPAAT has a substrate preference for substrates having a C16 or C18 acyl chain length; (3) the thioesterase has a substrate preference for one or more acyl substrates having an acyl chain length of C12 and the LPAAT has a substrate preference for one or more substrates having an acyl chain length selected from the group consisting of C14, C16, and C18 acyl chain length; and (4) the thioesterase has a substrate preference for one or more acyl substrates having an acyl chain length selected from the group consisting of C12, C14, C16, and C18, and the LPAAT has a substrate preference for substrates having a C20, C22, or C24 acyl chain length.

2. The recombinant microorganism of claim 1, wherein the LPAAT has a substrate preference for C16 acyl substrates.

3. The recombinant microorganism of claim 2, wherein the thioesterase has a substrate preference for one or more of a C12 and C14 acyl substrate.

4. The recombinant microorganism of claim 1, wherein the LPAAT has a substrate preference for C18 acyl substrates.

5. The recombinant microorganism of claim 4, wherein the thioesterase has a substrate preference for one or more of a C12, C14, and C16 acyl substrate.

6. The recombinant microorganism of claim 1, wherein the LPAAT is a cyanobacterial LPAAT.

7. The recombinant microorganism of claim 1, wherein the LPAAT is endogenous to the host microorganism.

8. The recombinant microorganism of claim 7, wherein the nucleic acid encoding the LPAAT is operably linked to a heterologous promoter.

9. The recombinant microorganism of claim 8, wherein the heterologous promoter is regulatable.

10. The recombinant microorganism of claim 1, wherein the thioesterase has a substrate preference for one or more of a C12, C14, and C16 acyl substrate.

11. The recombinant microorganism of claim 1, wherein the recombinant microorganism further comprises a disrupted acyl-ACP synthetase gene.

12. The recombinant microorganism of claim 1, wherein the recombinant microorganism produces at least 10% more fatty acid product than a microorganism substantially identical in all respects except that it lacks a non-native nucleic acid sequence encoding an LPAAT.

13. The recombinant microorganism of claim 1, wherein the recombinant microorganism is a photosynthetic microorganism.

14. The recombinant microorganism of claim 13, wherein the recombinant microorganism is a microalga.

15. The recombinant microorganism of claim 14, wherein the microalga is a species of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Skeletonema, Spyrogyra, Stichococcus, Tetraselmis, Thalassiosira, Viridiella,* or *Volvox.*

16. The recombinant microorganism of claim 13, wherein the photosynthetic microorganism is a *cyanobacterium*.

17. The recombinant microorganism of claim 16, wherein the *cyanobacterium* is a species of *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus.*

18. A method of producing a fatty acid product comprising culturing the recombinant microorganism of claim 1 under conditions in which at least one fatty acid product is produced.

19. The method of claim 18, wherein the fatty acid product is one or more of a free fatty acid, a fatty aldehyde, a fatty alcohol, a fatty acid ester, a wax ester, or a hydrocarbon.

20. The method of claim 19, wherein the fatty acid product comprises at least one $C_{12}$ to $C_{16}$ free fatty acid.

21. The method of claim 18, wherein the fatty acid product includes at least one $C_{12}$ to $C_{16}$ fatty alcohol or fatty aldehyde, at least one wax ester having an A chain of $C_{12}$ to $C_{16}$ and a B chain of $C_{12}$ to $C_{16}$, or at least one $C_{11}$ to $C_{15}$ alkane or alkene.

22. The method of claim 18, further comprising isolating the fatty acid product from the microorganism, the culture medium, or a combination thereof.

23. The method of claim 18, wherein at least a portion of the fatty acid product is secreted from the recombinant microorganism.

24. The method of claim 18, wherein the amount of fatty acid product produced by the recombinant microorganism is at least 10% greater than the amount produced by an otherwise identical microorganism lacking the non-native nucleic acid sequence encoding a thioesterase that is cultured under the same conditions.

25. A recombinant microorganism comprising a first non-native nucleic acid encoding a thioesterase having a substrate preference for one or more acyl substrates having an acyl chain length selected from the group consisting of C12, C14, and C16 and a second non-native nucleic acid encoding a LPAAT, having a substrate preference for substrates having a C18 acyl chain length wherein the microorganism produces a fatty acid product, and wherein the LPAAT has at least 85% identity to a LPAAT comprising an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15.

26. The recombinant microorganism of claim 25, wherein the thioesterase is an acyl-ACP thioesterase, an acyl-CoA thioesterase, or a 4-hydroxybenzoyl-CoA thioesterase.

27. The recombinant microorganism of claim 26, wherein the thioesterase is an acyl-ACP thioesterase.

28. The recombinant microorganism of claim 27, wherein the acyl-ACP thioesterase is a higher plant acyl-ACP thioesterase or a prokaryotic acyl-ACP thioesterase.

29. The recombinant microorganism of claim 25, wherein the recombinant microorganism further comprises a disrupted acyl-ACP synthetase gene.

30. The recombinant microorganism of claim 25, wherein the LPAAT has at least 90% identity to a LPAAT comprising an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15.

31. The recombinant microorganism of claim 30, wherein the LPAAT has at least 95% identity to a LPAAT comprising an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and SEQ ID NO:15.

32. A recombinant microorganism comprising a first non-native nucleic acid encoding an acyl-ACP thioesterase from a higher plant species or from a prokaryotic organism and a second non-native nucleic acid encoding an LPAAT from a prokaryotic organism, wherein the microorganism produces a fatty acid product, wherein the thioesterase and the LPAAT have complementary acyl-ACP substrate preferences, and wherein the complementary acyl-ACP substrate preferences are selected from the group consisting of: (1) the thioesterase has a substrate preference for one or more acyl substrates having an acyl chain length of C12 and C14 and the LPAAT has a substrate preference for substrates having a C16 or C18 acyl chain length; (2) the thioesterase has a substrate preference for one or more acyl substrates having an acyl chain length of C12 and the LPAAT has a substrate preference for one or more substrates having an acyl chain length selected from the group consisting of C14, C16, and C18 acyl chain length; and (3) the thioesterase has a substrate preference for one or more acyl substrates having an acyl chain length selected from the group consisting of C12, C14, and C18, and the LPAAT has a substrate preference for substrates having a C20, C22, or C24 acyl chain length.

* * * * *

SEQUENCE LISTING

<160> NUMBER OF SEQ ID NOS: 63

<210> SEQ ID NO 1
<211> LENGTH: 723
<212> TYPE: DNA
<213> ORGANISM: Synechocystis PCC6803

<400> SEQUENCE: 1

```
atgaccaatt ctcccctggc gatcgaccct gctgtcattg gcccttccag ggtttccccc      60
tggctaatca aattaattta tcccctaggc accaggtttt tacattggta ttttggcccg     120
atcgccatcc atggtcagga gcatttaccc cgcagtggcc cgattattct ggcccctacc     180
caccgttccc gttgggatgc aatttttgctt tctttggccg ccggtcgggg ggtaactggt     240
cgagacctcc gttttatggt ggcggtgacg gaagtgcagg gtttacaggg ttggtttatt     300
cgccatttgg ggggatttcc cgttgacgtg aaaaggccgg aaatcagtag tgtgagttat     360
agtgtgcagt tactccaagc aggggaaatg ttggtcattt ttcctgaggg gggcattttt     420
cgggatcaac acactgtcca tcccctcaaa cggggtattg ggcgcattgc catggaagtt     480
tgtaagcaaa accccaacac tgacattaaa gtgatcccag tgacgatcgc ctacagtgac     540
ccctacccag gcaaaggcac ttcagtggaa attaattttg gccagggcat cgccgctagg     600
gactacgacc ccagcaccat caaggctagc tcccaaaaac tgacccgttg tttggcccat     660
agaatgcaga acctttacag ttccgagaat gtctctctgt gcgaggcgat cgccgcttcg     720
tga                                                                    723
```

<210> SEQ ID NO 2
<211> LENGTH: 240
<212> TYPE: PRT
<213> ORGANISM: Synechocystis PCC6803

<400> SEQUENCE: 2

```
Met Thr Asn Ser Pro Leu Ala Ile Asp Pro Ala Val Ile Gly Pro Ser
1               5                   10                  15

Arg Val Ser Pro Trp Leu Ile Lys Leu Ile Tyr Pro Leu Gly Thr Arg
            20                  25                  30

Phe Leu His Trp Tyr Phe Gly Pro Ile Ala Ile His Gly Gln Glu His
        35                  40                  45

Leu Pro Arg Ser Gly Pro Ile Ile Leu Ala Pro Thr His Arg Ser Arg
    50                  55                  60

Trp Asp Ala Ile Leu Leu Ser Leu Ala Ala Gly Arg Gly Val Thr Gly
65                  70                  75                  80
```

```
Arg Asp Leu Arg Phe Met Val Ala Val Thr Glu Val Gln Gly Leu Gln
                85                  90                  95

Gly Trp Phe Ile Arg His Leu Gly Gly Phe Pro Val Asp Val Lys Arg
            100                 105                 110

Pro Glu Ile Ser Ser Val Ser Tyr Ser Val Gln Leu Leu Gln Ala Gly
        115                 120                 125

Glu Met Leu Val Ile Phe Pro Glu Gly Gly Ile Phe Arg Asp Gln His
130                 135                 140

Thr Val His Pro Leu Lys Arg Gly Ile Gly Arg Ile Ala Met Glu Val
145                 150                 155                 160

Cys Lys Gln Asn Pro Asn Thr Asp Ile Lys Val Ile Pro Val Thr Ile
                165                 170                 175

Ala Tyr Ser Asp Pro Tyr Pro Gly Lys Gly Thr Ser Val Glu Ile Asn
            180                 185                 190

Phe Gly Gln Gly Ile Ala Ala Arg Asp Tyr Asp Pro Ser Thr Ile Lys
        195                 200                 205

Ala Ser Ser Gln Lys Leu Thr Arg Cys Leu Ala His Arg Met Gln Asn
210                 215                 220

Leu Tyr Ser Ser Glu Asn Val Ser Leu Cys Glu Ala Ile Ala Ala Ser
225                 230                 235                 240

<210> SEQ ID NO 3
<211> LENGTH: 236
<212> TYPE: PRT
<213> ORGANISM: Cyanothece PCC 8801

<400> SEQUENCE: 3

Met Asn Gln Ser Thr Thr Ser Asn Ser Ile Glu Ser Ser Ile Asn Pro
1               5                   10                  15

Trp Leu Ile Arg Leu Val Tyr Pro Leu Gly Cys Ser Leu Ile Met Pro
            20                  25                  30

Leu Phe Phe Gly Arg Ile Thr Ile Ser Gly Gln Glu Asn Ile Pro Thr
        35                  40                  45

Thr Gly Pro Val Ile Val Ala Pro Thr His Arg Ser Arg Trp Asp Ala
50                  55                  60

Leu Ile Val Pro Gln Ala Val Gly Arg Leu Val Ser Gly Arg Asp Leu
65                  70                  75                  80

Arg Phe Met Val Met Ser Thr Glu Met Thr Gly Leu Gln Gly Trp Leu
                85                  90                  95

Ile Arg Arg Leu Gly Gly Phe Pro Ile Asp Val Lys Arg Pro Gly Leu
            100                 105                 110

Asp Ser Leu Glu His Ser Val Ser Ile Leu Lys Gln Gly Glu Met Leu
        115                 120                 125

Val Ile Phe Pro Glu Gly Gly Ile Phe Arg Asp Asn His Val His Pro
130                 135                 140

Leu Lys Arg Gly Val Ala Arg Ile Ala Leu Glu Val Val Ser Gln Gln
145                 150                 155                 160

Pro Asn Ser Gly Ile Lys Ile Leu Pro Val Ser Val Gln Tyr Thr Gln
                165                 170                 175

Pro Tyr Pro Ala Trp Gly Thr Asp Val Ile Val Asn Ile Gly Gln Pro
            180                 185                 190

Ile Asp Val Ala Lys Tyr Asn Pro Gln Arg Met Lys Ser Ser Ser Glu
        195                 200                 205
```

```
Ala Leu Thr Asn Asp Leu Glu Ala Lys Leu Lys Asp Leu Tyr Gln Gly
        210                 215                 220

Gln Lys Ala Leu Asn Leu Ala Glu Phe Val Gly Ser
225                 230                 235

<210> SEQ ID NO 4
<211> LENGTH: 251
<212> TYPE: PRT
<213> ORGANISM: Crocosphaera watsonii WH 8501

<400> SEQUENCE: 4

Met Cys Asn Leu His Arg Glu Ile Val Phe Val Ala Phe Cys Leu Lys
1               5                   10                  15

Lys Met Asn Ile His Lys Asn Lys Ser Asp Arg Val Lys Ser Gln Ile
            20                  25                  30

Ser Pro Trp Leu Ile Asn Ile Ala Tyr Pro Leu Gly Ser Lys Ile Val
        35                  40                  45

Leu Pro Leu Tyr Phe Gly Ser Ile Thr Ile Asn Gly Gln Glu Asn Ile
    50                  55                  60

Pro Thr Ser Gly Pro Ile Leu Ile Ala Pro Thr His Arg Ser Arg Trp
65                  70                  75                  80

Asp Ala Leu Ile Ile Pro Tyr Ala Val Gly Arg Ile Val Ser Gly Arg
                85                  90                  95

Asp Val Arg Phe Met Val Thr Ser Ser Glu Ile Thr Gly Ile Gln Gly
            100                 105                 110

Trp Phe Ile Arg Arg Met Gly Gly Phe Pro Val Asp Leu Lys Arg Pro
        115                 120                 125

Gly Ala Ser Ser Leu Glu His Ser Val Glu Ile Leu Lys Gln Gly Glu
    130                 135                 140

Met Leu Val Ile Phe Pro Glu Gly Gly Ile Phe Arg Asp Lys Glu Val
145                 150                 155                 160

His Pro Leu Lys Arg Gly Val Ala Arg Ile Ala Leu Glu Val Glu Ser
                165                 170                 175

Gln Gln Pro Gly Cys Gly Met Lys Ile Leu Pro Val Ser Ile Glu Tyr
            180                 185                 190

Thr Lys Pro Phe Pro Ser Trp Gly Thr His Ile Thr Val Asn Ile Gly
        195                 200                 205

Cys Ser Leu Asp Val Ala Ser Tyr Asp Thr Thr Leu Lys Arg Ser
    210                 215                 220

Ser Gln Lys Leu Thr Gln Asp Leu Glu Ser His Leu Lys Trp Ile Phe
225                 230                 235                 240

Gln Gly Lys Leu Glu Gln Ile Val Ile Gln Lys
                245                 250

<210> SEQ ID NO 5
<211> LENGTH: 234
<212> TYPE: PRT
<213> ORGANISM: Cyanothece CCY0110

<400> SEQUENCE: 5

Met Asn Ile Ser Thr Ile Lys Ser Asp Gln Val Lys Ser Arg Ile Ser
1               5                   10                  15

Pro Trp Leu Ile Arg Ile Thr Tyr Pro Leu Gly Ser Trp Leu Val Leu
            20                  25                  30

Pro Leu Tyr Phe Gly Arg Ile Lys Ile Thr Gly Gln Glu Asn Ile Pro
        35                  40                  45
```

-continued

```
Asp Thr Gly Pro Val Ile Ile Ala Pro Thr His Arg Ser Arg Trp Asp
 50                  55                  60

Ala Leu Ile Ile Pro Tyr Ala Val Gly Arg Met Val Ser Gly Arg Asp
 65                  70                  75                  80

Val Arg Phe Met Val Thr Ser Ser Glu Met Glu Gly Ile Gln Gly Trp
                 85                  90                  95

Phe Ile Arg Arg Leu Gly Gly Phe Pro Val Asp Val Lys Arg Pro Gly
            100                 105                 110

Pro Ser Ser Leu Glu His Ser Ile Glu Val Leu Lys Gln Gly Glu Met
        115                 120                 125

Leu Val Ile Phe Pro Glu Gly Gly Ile Phe Arg Asp Thr Glu Val His
130                 135                 140

Pro Leu Lys Arg Gly Val Ala Arg Ile Ala Leu Asp Val Glu Ser Gln
145                 150                 155                 160

Gln Pro Gly Cys Gly Met Lys Ile Leu Pro Ile Gly Ile Glu Tyr Ser
                165                 170                 175

Gln Pro Phe Pro Ser Trp Gly Thr Asp Val Thr Val Asn Ile Gly Ser
            180                 185                 190

Pro Leu Asp Val Ala Thr Tyr Asp Thr Thr Lys Met Lys Arg Ser Ser
        195                 200                 205

Glu Lys Leu Thr Ile Asp Leu Glu Ser Asp Leu Lys Gln Val Phe His
210                 215                 220

His Gln Ser Glu Ala Ile Val Phe Gln Ser
225                 230

<210> SEQ ID NO 6
<211> LENGTH: 236
<212> TYPE: PRT
<213> ORGANISM: Microcystis aeruginosa

<400> SEQUENCE: 6

Met Ser Gln Ser Thr Ile Val Asp Glu Ser Leu Thr Ile Arg Lys Ser
 1               5                  10                  15

Pro Ala Val Asn Ser Arg Ile Asn Pro Cys Leu Ile Arg Phe Cys Tyr
             20                  25                  30

Phe Leu Gly Asn Tyr Leu Val Leu Pro Ala Phe Phe Ser Lys Ile Thr
         35                  40                  45

Val Thr Gly Gln Glu Asn Ile Pro Leu Thr Gly Gly Val Ile Leu Ala
 50                  55                  60

Pro Thr His Arg Ser Arg Trp Asp Ala Leu Ile Leu Pro Tyr Ala Val
 65                  70                  75                  80

Gly Arg Leu Val Ser Gly Arg Asp Leu Arg Phe Met Val Ser Ala Asn
                 85                  90                  95

Glu Ile Lys Gly Val Gln Gly Trp Phe Ile Arg Arg Leu Gly Gly Phe
            100                 105                 110

Pro Val Asn Thr Asp His Pro Gly Met Gly Ser Leu Val His Ser Val
        115                 120                 125

Glu Leu Leu Ala Ala Gly Glu Met Val Ala Ile Phe Pro Glu Gly Gly
130                 135                 140

Ile Cys Arg Asp Arg Val Val His Pro Leu Lys Pro Gly Val Ala Arg
145                 150                 155                 160

Ile Ala Leu Glu Val Lys Thr Met Lys Pro Asp Ala Asp Ile Lys Ile
                165                 170                 175

Leu Pro Val Ser Ile Ser Tyr Asn Gln Pro Tyr Pro Gly Trp Gly Ser
            180                 185                 190
```

Glu Ala Thr Val Asn Ile Gly Gln Gly Ile Asn Val Leu Asp Tyr Gln
        195                 200                 205

Gln Asn Ser Leu Lys Arg Glu Thr Val Arg Leu Thr Lys Thr Leu Ser
        210                 215                 220

Asp Arg Leu Lys Leu Leu His Glu Asp Gln Ser Pro
225                 230                 235

<210> SEQ ID NO 7
<211> LENGTH: 287
<212> TYPE: PRT
<213> ORGANISM: Nostoc PCC 7120

<400> SEQUENCE: 7

Met Ile Glu Phe Phe Ser Val Ser Asp Thr His Gln Thr Gln Pro Thr
1               5                   10                  15

Asn Arg Leu Val His Pro Gln Val Ala Val Thr Thr Ser Arg Val Ser
            20                  25                  30

Pro Trp Leu Ser Pro Val Leu Tyr Phe Val Gly Asn Tyr Phe Leu Leu
        35                  40                  45

Pro Ser Phe Phe Gly Arg Ile Ser Ile Thr Gly Gln Glu Asn Ile Pro
    50                  55                  60

Lys Thr Gly Pro Val Ile Leu Ala Pro Thr His Arg Ala Arg Trp Asp
65                  70                  75                  80

Ser Leu Leu Leu Pro Tyr Ala Thr Gly Arg Tyr Val Thr Gly Arg Asp
                85                  90                  95

Leu Lys Phe Met Val Thr Lys Thr Glu Cys Arg Gly Leu Gln Gly Trp
            100                 105                 110

Phe Val Arg Arg Met Gly Gly Phe Pro Ile Asp Thr Gln His Pro Ala
        115                 120                 125

Val Ser Thr Leu Arg His Ala Val Glu Leu Leu Gln Gln Gly Gln Met
    130                 135                 140

Leu Val Ile Tyr Pro Glu Gly Asn Ile Phe Arg Asp Gly Lys Leu His
145                 150                 155                 160

Pro Leu Lys Ser Gly Ile Ser Arg Leu Ala Leu Ser Ala Glu Ser Ser
                165                 170                 175

His Pro Gly Leu Gly Val Lys Ile Leu Pro Ile Ser Ile Asn Tyr Ser
            180                 185                 190

Gln Pro Tyr Pro Cys Trp Gly Thr Asp Val Ser Ile His Ile Gly Ser
        195                 200                 205

Pro Ile Asn Val Gln Asp Tyr Thr Lys Gly Lys Val Lys Gln Asn Ala
    210                 215                 220

Lys Arg Leu Thr Glu Asp Leu Ala Arg Asp Leu Gln Ser Leu Ser Asn
225                 230                 235                 240

Pro Glu Leu Ala Phe Ser His His Asp Ala Ala Glu Val Ser Thr Ser
                245                 250                 255

Pro Ile Val Ser Val Ser Asp Ser Thr Glu Arg Ser Pro Asn Val Arg
            260                 265                 270

Gly Gly Ala Thr Ser Arg Lys Arg Glu Leu Leu Thr Ile Asp Tyr
        275                 280                 285

<210> SEQ ID NO 8
<211> LENGTH: 309
<212> TYPE: PRT
<213> ORGANISM: Anabaena variabilis

```
<400> SEQUENCE: 8

Met Ile Glu Phe Phe Ser Val Ser Asp Thr Arg Gln Thr Gln Pro Thr
1               5                   10                  15

Asn Thr Leu Phe Pro Pro Gln Val Ala Val Thr Thr Ser Lys Val Ser
            20                  25                  30

Pro Trp Leu Ser Pro Val Leu Tyr Phe Val Gly Asn Tyr Leu Leu Leu
        35                  40                  45

Pro Ser Phe Phe Gly Arg Ile Ser Ile Thr Gly Gln Glu Asn Ile Pro
    50                  55                  60

Asn Thr Gly Pro Val Ile Leu Ala Pro Thr His Arg Ala Arg Trp Asp
65                  70                  75                  80

Ser Leu Leu Leu Pro Tyr Ala Thr Gly Arg Tyr Val Thr Gly Arg Asp
                85                  90                  95

Leu Lys Phe Met Val Thr Lys Thr Glu Cys Arg Gly Leu Gln Gly Trp
            100                 105                 110

Phe Val Arg Arg Met Gly Gly Phe Pro Ile Asp Thr Gln His Pro Ala
        115                 120                 125

Ile Ser Thr Leu Arg His Ala Val Glu Leu Leu Gln Gln Gly Gln Met
    130                 135                 140

Leu Val Ile Tyr Pro Glu Gly Asn Ile Phe Arg Asp Gly Lys Leu His
145                 150                 155                 160

Pro Leu Lys Ser Gly Ile Ser Arg Leu Ala Leu Ser Ala Glu Ser Ser
                165                 170                 175

His Pro Gly Leu Gly Val Lys Ile Leu Pro Val Ser Ile Asn Tyr Ser
            180                 185                 190

Gln Pro Tyr Pro Cys Trp Gly Thr Asp Val Ser Ile His Ile Gly Thr
        195                 200                 205

Ala Ile Asn Val Gln Asp Tyr Thr Asn Gly Lys Val Lys Gln Asn Ala
    210                 215                 220

Lys Arg Leu Thr Glu Asp Leu Ala Arg Asp Leu Gln Ser Leu Ser Asn
225                 230                 235                 240

Pro Glu Leu Ala Phe Ser His His Asp Val Ala Glu Val Ser Asn Pro
                245                 250                 255

Pro Lys Gly Lys Gly Asp Glu Gly Ala Glu Ala Val Glu Glu Gln Cys
            260                 265                 270

Gly Leu Gly Leu Cys Pro Ser Gly Ala Ile Ala Glu Glu Gln Ala Ser
        275                 280                 285

Ile Val Ser Val Ser Arg Thr Gly Ala Thr Ser Arg Arg Arg Glu Leu
    290                 295                 300

Leu Thr Val Asp Tyr
305

<210> SEQ ID NO 9
<211> LENGTH: 256
<212> TYPE: PRT
<213> ORGANISM: Nostoc azollae

<400> SEQUENCE: 9

Met Met Glu Phe Tyr Ser Ala Ser Thr Lys Pro Gln Ser Gln Ile Thr
1               5                   10                  15

Asn Thr Leu Val Asn Pro Lys Val Ala Cys Ser Thr Ser Arg Val Ser
            20                  25                  30

Pro Trp Leu Thr Pro Leu Ala Tyr Leu Leu Gly Arg Asn Ile Val Leu
        35                  40                  45
```

Pro Leu Phe Phe Gly Asp Ile His Ile Thr Gly Gln Glu Asn Ile Pro
    50                  55                  60

Thr Ser Gly Pro Ile Ile Leu Ala Pro Thr His Arg Ser Arg Trp Asp
 65                  70                  75                  80

Ser Leu Leu Leu Pro Tyr Ala Thr Gly Arg Cys Val Thr Gly Arg Asp
                 85                  90                  95

Met Arg Phe Met Val Thr Ser Glu Cys Lys Gly Val Gln Gly Trp
                100                 105                 110

Phe Val Arg Arg Met Gly Gly Phe Pro Val Asp Thr Gln Arg Pro Ala
            115                 120                 125

Ile Ala Thr Leu Arg His Thr Val Glu Leu Met Val Glu Gly Glu Met
130                 135                 140

Leu Val Ile Tyr Pro Glu Gly Gly Ile Tyr Arg Asp Gly Lys Val His
145                 150                 155                 160

Ala Leu Lys Ser Gly Ile Ser Arg Leu Ala Leu Ser Ala Ala Ser Val
                165                 170                 175

His Pro Gly Leu Glu Ile Lys Ile Leu Thr Val Gly Ile Asn Tyr Ser
            180                 185                 190

Gln Pro Tyr Pro Asn Trp Gly Thr Asp Val Asn Ile His Ile Gly Lys
        195                 200                 205

Pro Ile Lys Val Thr Asp Tyr Ile Ser Gly Cys Leu Lys Lys Glu Ala
    210                 215                 220

Lys Arg Leu Thr Ala Asp Leu Thr Asn Gln Leu Gln Gln Leu Ser His
225                 230                 235                 240

Gln Gly Leu Glu Val Lys Ser His Ala Phe Ala Glu Ile Pro Asn Ser
                245                 250                 255

<210> SEQ ID NO 10
<211> LENGTH: 246
<212> TYPE: PRT
<213> ORGANISM: Raphidiopsis brookii

<400> SEQUENCE: 10

Met Lys Glu Pro His Ser Ala Ser Thr Ser Phe Ala Asp Gln Ser Pro
 1               5                  10                  15

Asn Ile Cys Leu Asp Pro Pro Phe Ser His Thr Arg Ser Trp Ile Ser
                 20                  25                  30

Pro Trp Leu Thr Pro Leu Ala Tyr Trp Leu Gly Tyr His Leu Val Ile
             35                  40                  45

Pro Leu Phe Phe Gly Ser Ile His Val Glu Gly Gln Glu His Ile Pro
    50                  55                  60

Ile Arg Gly Pro Val Ile Leu Ala Pro Thr His Arg Ser Arg Trp Asp
 65                  70                  75                  80

Pro Leu Leu Leu Ala Tyr Ala Ala Gly Arg Tyr Ile Thr Gly Arg Asp
                 85                  90                  95

Leu Arg Phe Met Val Met Ser Ser Glu Cys Arg Gly Ile Gln Gly Trp
                100                 105                 110

Phe Ile Leu Ser Met Gly Gly Phe Ala Val Asn Leu Gln Arg Pro Gly
            115                 120                 125

Ile Lys Ser Leu Arg His Val Ile Asp Leu Met Leu Gly Gly Glu Met
130                 135                 140

Leu Val Ile Tyr Pro Glu Gly Gly Ile Phe Arg Asp Gly Lys Ile His
145                 150                 155                 160

Pro Leu Lys Ser Gly Ile Ala Arg Leu Ser Ile Asn Ala Gln Ser Leu
                165                 170                 175

```
Asp Pro Asn Leu Asp Ile Lys Ile Ile Pro Val Ser Ile Asn Tyr Asp
            180                 185                 190

Arg Pro Tyr Pro Asn Trp Gly Thr Lys Val Lys Ile Cys Ile Gly Glu
        195                 200                 205

Pro Val Lys Val Ala Asp Tyr Met His Gly Cys Leu Lys Gln Asn Ser
    210                 215                 220

Gln Tyr Leu Thr Arg Asp Leu Arg Ser Lys Leu Gln Glu Val Ala Asp
225                 230                 235                 240

Ser Gln Pro Val Ser Leu
                245

<210> SEQ ID NO 11
<211> LENGTH: 253
<212> TYPE: PRT
<213> ORGANISM: Microcoleus chthonoplastes

<400> SEQUENCE: 11

Met Gln Leu Gln Ser Arg Glu Gln Asn Gln Thr Pro Ser Thr Leu Asp
1               5                   10                  15

Lys Pro Asp Ser Lys Thr Val Asn Ser Ala Lys Ile Val Pro Val Asn
            20                  25                  30

Ser Asn Val Ser Pro Trp Leu Thr Ser Ile Phe Tyr Pro Leu Gly Arg
        35                  40                  45

Arg Ile Leu Met Pro Leu Tyr Phe Gly Arg Leu Gln Val Thr Gly Gln
    50                  55                  60

Asp Asn Ile Pro Lys Thr Gly Pro Val Ile Leu Ala Pro Thr His Arg
65                  70                  75                  80

Ser Arg Trp Asp Gly Leu Thr Met Ala Tyr Ala Ala Gly Lys Pro Val
                85                  90                  95

Thr Gly Arg Asp Leu Arg Phe Met Val Ser Gln Asp Glu Met Lys Gly
            100                 105                 110

Leu Gln Gly Trp Phe Ile Arg Arg Leu Gly Gly Phe Pro Val Asn Thr
        115                 120                 125

Lys His Pro Gly Ile Ser Ser Ile Arg His Ser Val Glu Leu Leu Arg
    130                 135                 140

Arg Gly Glu Ala Leu Val Met Phe Pro Glu Gly Asn Ile Phe Arg His
145                 150                 155                 160

Gly Asp Val Asn Pro Leu Lys Pro Gly Met Ala Arg Ile Ala Leu Gln
                165                 170                 175

Ala Glu Ser Asn Gln Pro Gly Leu Gly Leu Lys Ile Val Pro Val Ser
            180                 185                 190

Ile Arg Tyr Ser Asp Pro Val Pro Gln Trp Gly Ser Asp Ile Asp Ile
        195                 200                 205

Gln Ile Gly Ser Ala Leu Asp Val Ala Lys Tyr Cys Asn Gln Ser Ala
    210                 215                 220

Lys Lys Gly Ala Gln Gln Leu Thr Thr Asp Leu Glu Ile Ala Leu Lys
225                 230                 235                 240

Gln Val Asp Gln Lys Leu Glu Val Ile Lys Glu Ala Val
                245                 250

<210> SEQ ID NO 12
<211> LENGTH: 255
<212> TYPE: PRT
<213> ORGANISM: Cylindrospermopsis raciborskii
```

<400> SEQUENCE: 12

```
Met Lys Glu Ser His Ser Ala Ser Thr Ser Phe Ala Gly Gln Ser Pro
1               5                   10                  15

Asn Ile Cys Leu Asp Pro Pro Phe Ser His Thr Arg Ser Trp Ile Ser
            20                  25                  30

Pro Trp Leu Thr Pro Leu Ala Tyr Trp Leu Gly Tyr Asn Leu Val Ile
        35                  40                  45

Pro Ser Phe Phe Gly Arg Ile Asp Val Ala Gly Gln Gln His Ile Pro
    50                  55                  60

Ile Lys Gly Pro Val Ile Leu Ala Pro Thr His Arg Ser Arg Trp Asp
65                  70                  75                  80

Pro Leu Leu Leu Ala Tyr Ala Ala Gly Arg Tyr Ile Thr Gly Arg Asp
                85                  90                  95

Leu Arg Phe Met Val Met Ser Ser Glu Cys Arg Gly Ile Gln Gly Trp
            100                 105                 110

Phe Ile Leu Ser Met Gly Gly Phe Ala Val Asn Leu Gln Arg Pro Gly
        115                 120                 125

Ile Arg Ser Leu Arg His Ala Val Asp Leu Met Leu Gly Gly Glu Met
    130                 135                 140

Leu Val Ile Tyr Pro Glu Gly Gly Ile Phe Arg Asp Gly Lys Ile His
145                 150                 155                 160

Pro Leu Lys Ser Gly Ile Ala Arg Leu Ser Ile Asn Ala Gln Ser Leu
                165                 170                 175

Asp Pro Asn Leu Asp Ile Lys Ile Ile Pro Val Ala Ile Asn Tyr Asp
            180                 185                 190

Arg Pro Tyr Pro Ser Trp Gly Thr Lys Val Lys Ile Arg Ile Gly Glu
        195                 200                 205

Pro Val Lys Val Thr Asp Tyr Ile His Gly Cys Leu Lys Gln Asn Ala
    210                 215                 220

Lys Tyr Leu Thr Arg Asp Leu Arg Ser Lys Leu Gln Glu Val Ala Asp
225                 230                 235                 240

Ser Gln Pro Asp Phe Ser Leu Arg Ala Asn Cys Leu Thr Asn Ser
                245                 250                 255
```

<210> SEQ ID NO 13
<211> LENGTH: 236
<212> TYPE: PRT
<213> ORGANISM: Oscillatoria PCC 6506

<400> SEQUENCE: 13

```
Met Ile Thr Phe Asp Ser Thr Asn Ser Ser Leu Glu Thr Gln Met Pro
1               5                   10                  15

Ala Lys Ala Thr Ser Ile Asn Ser His Val Ser Pro Trp Leu Ala Pro
            20                  25                  30

Leu Val Tyr Pro Leu Gly Arg Tyr Leu Ile Leu Pro Phe Tyr Phe Arg
        35                  40                  45

Ser Ile Glu Val Leu Gly Gln Glu His Ile Pro Arg Glu Gly Pro Val
    50                  55                  60

Ile Leu Ala Pro Thr His Arg Ser Arg Trp Asp Ser Gln Met Leu Pro
65                  70                  75                  80

Tyr Ser Thr Gly Arg Tyr Val Thr Gly Arg Asp Leu Arg Phe Met Val
                85                  90                  95

Ser Val Asn Glu Val Lys Gly Leu Gln Gly Trp Phe Ile Arg Arg Leu
            100                 105                 110
```

```
Gly Gly Phe Pro Val Asp Pro Lys His Pro Ala Ile Ala Thr Leu Arg
            115                 120                 125

His Gly Val Glu Leu Leu Asp Gly Gln Met Phe Val Ile Phe Pro
    130                 135                 140

Glu Gly Gly Ile Phe Gln Asp Asn Gln Val His Pro Leu Lys Pro Gly
145                 150                 155                 160

Leu Ala Arg Leu Ala Ile Gln Ala Glu Ser Ser His Pro Gly Leu Asp
                165                 170                 175

Val Lys Ile Val Pro Met Ser Ile Arg Tyr His Pro Cys Ile Pro Arg
            180                 185                 190

Trp Gly Ser Arg Val Lys Ile Thr Ile Gly Ser Pro Leu Ser Ala Ala
            195                 200                 205

Asp Tyr Cys Thr Gly Ala Gly Lys Lys Asp Ala Gln Leu Leu Thr Ala
    210                 215                 220

Asp Leu Glu Thr Ala Leu Lys Arg Ile Asp Arg Glu
225                 230                 235

<210> SEQ ID NO 14
<211> LENGTH: 250
<212> TYPE: PRT
<213> ORGANISM: Nodularia spumigena

<400> SEQUENCE: 14

Met Glu Ile Tyr Thr Ser His Gln Thr Ser Gln Glu Thr Pro Ala Ser
1               5                   10                  15

Asn Lys Ala Asn Thr Lys Val Ala His Thr Thr Ser Arg Val Ser Pro
            20                  25                  30

Trp Leu Ser Pro Leu Leu Tyr Leu Gly Gln His Leu Leu Leu Pro
        35                  40                  45

Phe Phe Phe Arg Gln Ile Glu Ile Thr Gly Gln Glu Asn Ile Pro Leu
    50                  55                  60

Thr Gly Pro Val Ile Leu Ala Pro Thr His Arg Ser Arg Trp Asp Ser
65                  70                  75                  80

Leu Leu Leu Pro Tyr Ala Thr Gly Arg Cys Val Thr Gly Arg Asp Leu
                85                  90                  95

Arg Phe Met Val Thr Ile Asn Glu Cys Gln Gly Leu Gln Gly Trp Leu
            100                 105                 110

Val Arg Ser Met Gly Gly Phe Pro Val Asn Pro Gln Arg Pro Ala Ile
            115                 120                 125

Thr Thr Leu Arg His Ala Val Glu Leu Leu Gln Gln Gly Glu Ile Leu
    130                 135                 140

Val Ile Tyr Pro Glu Gly Asn Ile Tyr Arg Asp Gly Lys Leu His Pro
145                 150                 155                 160

Leu Lys Pro Gly Ile Ala Arg Leu Ser Leu Thr Ala Glu Ser Ser His
                165                 170                 175

Pro Gly Leu Asp Val Lys Ile Leu Pro Val Ser Ile Asn Tyr Ser Gln
        180                 185                 190

Pro Tyr Pro Gln Trp Gly Thr Ser Val Lys Ile Ser Ile Gly Thr Thr
    195                 200                 205

Leu Asn Val Ala Asp Tyr Thr Gly Gly Lys Val Lys Gln Asn Ala Gln
    210                 215                 220

Asn Leu Thr Ser Asp Leu Ser Leu Val Leu Gln Leu Ser Pro Gln
225                 230                 235                 240

Glu Ser Val Ile Pro Glu Asn Val Asn Ser
            245                 250
```

<210> SEQ ID NO 15
<211> LENGTH: 242
<212> TYPE: PRT
<213> ORGANISM: Microcoleus vaginatus

<400> SEQUENCE: 15

Met Pro His Thr Ala Thr Ile Ala Val Glu Ser Ser Lys Ser Ser Leu
1               5                   10                  15

Val Lys Pro Met Pro Ala Lys Val Ala Ser Asn Thr Ser Arg Val Ser
            20                  25                  30

Pro Trp Leu Thr Ser Leu Leu Tyr Pro Leu Gly His Tyr Val Val Leu
        35                  40                  45

Pro Phe His Phe Gly Lys Ile Glu Ile Thr Gly Gln Glu His Leu Pro
    50                  55                  60

Lys Asp Gly Pro Val Ile Leu Ala Pro Thr His Arg Ser Arg Trp Asp
65                  70                  75                  80

Ala Leu Met Met Pro Tyr Ser Thr Gly Gln Lys Val Thr Gly Arg Asp
                85                  90                  95

Leu Arg Phe Met Val Thr Ala Asp Glu Val Lys Gly Leu Gln Gly Trp
            100                 105                 110

Phe Ile Arg Asn Leu Gly Gly Phe Pro Val Asp Leu Lys His Pro Ala
        115                 120                 125

Ile Gly Thr Leu Arg Tyr Gly Val Glu Leu Leu Leu Asp Arg Glu Met
    130                 135                 140

Leu Val Ile Phe Pro Glu Gly Gly Ile Phe Gln Asp Gly Glu Val His
145                 150                 155                 160

Pro Ile Lys Pro Gly Leu Ala Arg Leu Ala Met Gln Ala Glu Leu Ser
                165                 170                 175

Lys Pro Gly Leu Gly Val Lys Ile Val Pro Met Ser Ile Arg Tyr Arg
            180                 185                 190

Pro Arg Ile Pro Gln Trp Gly Cys Gln Val Lys Ile Ala Ile Gly Ser
        195                 200                 205

Pro Ile Ser Val Ala Asp Tyr Ala Asn Gly Gly Gly Lys Lys Glu
    210                 215                 220

Ala Arg Leu Leu Ser Ala Gln Leu Glu Met Asp Leu Lys Lys Leu Asp
225                 230                 235                 240

Glu Ser

<210> SEQ ID NO 16
<211> LENGTH: 245
<212> TYPE: PRT
<213> ORGANISM: Escherichia coli

<400> SEQUENCE: 16

Met Leu Tyr Ile Phe Arg Leu Ile Ile Thr Val Ile Tyr Ser Ile Leu
1               5                   10                  15

Val Cys Val Phe Gly Ser Ile Tyr Cys Leu Phe Ser Pro Arg Asn Pro
            20                  25                  30

Lys His Val Ala Thr Phe Gly His Met Phe Gly Arg Leu Ala Pro Leu
        35                  40                  45

Phe Gly Leu Lys Val Glu Cys Arg Lys Pro Thr Asp Ala Glu Ser Tyr
    50                  55                  60

Gly Asn Ala Ile Tyr Ile Ala Asn His Gln Asn Asn Tyr Asp Met Val
65                  70                  75                  80

-continued

Thr Ala Ser Asn Ile Val Gln Pro Pro Thr Val Thr Val Gly Lys Lys
            85                  90                  95

Ser Leu Leu Trp Ile Pro Phe Phe Gly Gln Leu Tyr Trp Leu Thr Gly
        100                 105                 110

Asn Leu Leu Ile Asp Arg Asn Arg Thr Lys Ala His Gly Thr Ile
    115                 120                 125

Ala Glu Val Val Asn His Phe Lys Lys Arg Ile Ser Ile Trp Met
130                 135                 140

Phe Pro Glu Gly Thr Arg Ser Arg Gly Arg Leu Leu Pro Phe Lys
145                 150                 155                 160

Thr Gly Ala Phe His Ala Ala Ile Ala Ala Gly Val Pro Ile Ile Pro
                165                 170                 175

Val Cys Val Ser Thr Thr Ser Asn Lys Ile Asn Leu Asn Arg Leu His
            180                 185                 190

Asn Gly Leu Val Ile Val Glu Met Leu Pro Pro Ile Asp Val Ser Gln
        195                 200                 205

Tyr Gly Lys Asp Gln Val Arg Glu Leu Ala Ala His Cys Arg Ser Ile
    210                 215                 220

Met Glu Gln Lys Ile Ala Glu Leu Asp Lys Glu Val Ala Glu Arg Glu
225                 230                 235                 240

Ala Ala Gly Lys Val
                245

<210> SEQ ID NO 17
<211> LENGTH: 231
<212> TYPE: PRT
<213> ORGANISM: Marinobacter adhaerens

<400> SEQUENCE: 17

Met Leu Arg Leu Leu Lys Ala Ala Trp Ile Leu Phe Trp Ala Ile Leu
1               5                   10                  15

Leu Thr Leu Ile Leu Phe Phe Pro Ile Val Ile Ala Ala Leu Leu Gly
            20                  25                  30

Lys Arg Gly Asp Ala Ala Phe His Gly Thr Gln Ile Tyr Ala Trp Ile
        35                  40                  45

Ile Leu Lys Val Cys Gly Ile Arg Leu Lys Val Arg Gly Arg Glu Asn
    50                  55                  60

Ile Glu Pro Gly Gln Arg Tyr Val Ile Leu Ser Asn His Ala Ser Tyr
65                  70                  75                  80

Leu Asp Pro Pro Ala Leu Val Leu Ala Leu Gly Leu Gln Tyr Arg Trp
                85                  90                  95

Val Ile Lys Lys Glu Leu Arg Lys Val Pro Leu Phe Gly Leu Ala Leu
            100                 105                 110

Glu Ala Ser Arg Asn Leu Phe Ile Asp Arg Ser Lys Gly Ser Asp Ala
        115                 120                 125

Leu Glu Ser Ile Lys Arg Gly Val Gly Gln Leu Pro Asp Gly Thr Gly
    130                 135                 140

Ile Leu Ile Phe Pro Glu Gly Thr Arg Ser Trp Asp Gly Lys Leu Leu
145                 150                 155                 160

Pro Phe Lys Lys Gly Gly Phe Val Ile Ala Gln Asp Gly Glu Leu Pro
                165                 170                 175

Ile Leu Pro Val Thr Ile Cys Gly Ser His Gln Arg Leu Pro Lys Gly
            180                 185                 190

Ser Ala Ala Phe Ser Arg Gly Asp Ile Glu Ile Val Ile His Pro Pro
        195                 200                 205

```
Met Ala Ser Gly Ala Leu Pro Leu Asp Asp Leu Met Thr Asp Val Arg
            210                 215                 220

Asn Ser Ile Ala Ser Ser Leu
225                 230

<210> SEQ ID NO 18
<211> LENGTH: 332
<212> TYPE: PRT
<213> ORGANISM: Oryza sativa

<400> SEQUENCE: 18

Met Gly Thr Leu Leu Arg Pro Arg Pro Leu Ala His Ala Ala Gly Ala
1               5                   10                  15

Gly Asp Ala Thr Pro Ser Thr Ala His Ala Val Val Ser Gly Gly
            20                  25                  30

Arg Gly Arg Gly Val Glu Cys Gln Pro His Arg Val Arg Arg Pro
        35                  40                  45

Gly Pro Gln Val Ala Val Ala Thr Ala Ser Trp Arg Arg Arg Glu
    50                  55                  60

Thr Val Val Arg Ser Asp Phe Ala Ala Gly Ala Ala Thr Met Gly
65                  70                  75                  80

Asp Ser Pro Gln Ala Leu Ser Asp Ile Asp Val Val Ser Arg Val Arg
                85                  90                  95

Gly Val Cys Phe Tyr Ala Val Thr Ala Val Ala Ala Ile Phe Leu Phe
            100                 105                 110

Val Ala Met Val Val Val His Pro Leu Val Leu Leu Phe Asp Arg Tyr
            115                 120                 125

Arg Arg Arg Ala Gln His Tyr Ile Ala Lys Ile Trp Ala Thr Leu Thr
130                 135                 140

Ile Ser Met Phe Tyr Lys Leu Asp Val Glu Gly Met Glu Asn Leu Pro
145                 150                 155                 160

Pro Asn Ser Ser Pro Ala Val Tyr Val Ala Asn His Gln Ser Phe Leu
                165                 170                 175

Asp Ile Tyr Thr Leu Leu Thr Leu Gly Arg Cys Phe Lys Phe Ile Ser
            180                 185                 190

Lys Thr Ser Ile Phe Met Phe Pro Ile Ile Gly Trp Ala Met Tyr Leu
        195                 200                 205

Leu Gly Val Ile Pro Leu Arg Arg Met Asp Ser Arg Ser Gln Leu Asp
    210                 215                 220

Cys Leu Lys Arg Cys Val Asp Leu Val Lys Lys Gly Ala Ser Val Phe
225                 230                 235                 240

Phe Phe Pro Glu Gly Thr Arg Ser Lys Asp Gly Lys Leu Gly Ala Phe
                245                 250                 255

Lys Arg Gly Ala Phe Ser Val Ala Thr Lys Thr Gly Ala Pro Val Ile
            260                 265                 270

Pro Ile Thr Leu Leu Gly Thr Gly Lys Leu Met Pro Ser Gly Met Glu
        275                 280                 285

Gly Ile Leu Asn Ser Gly Ser Val Lys Leu Ile Ile His His Pro Ile
    290                 295                 300

Glu Gly Asn Asp Ala Glu Lys Leu Cys Ser Glu Ala Arg Lys Val Ile
305                 310                 315                 320

Ala Asp Thr Leu Ile Leu Asn Gly Tyr Gly Val His
                325                 330
```

<210> SEQ ID NO 19
<211> LENGTH: 345
<212> TYPE: PRT
<213> ORGANISM: Glycine max

<400> SEQUENCE: 19

```
Met Glu Val Thr Pro Leu Ser Ser Pro Ser Pro Ile His Arg Leu His
1               5                   10                  15

Leu Arg His Lys Glu Ala Arg Phe Leu Ala Val Pro Ser Thr Leu Leu
            20                  25                  30

Cys Thr Arg Arg Gly Thr Thr Thr Tyr Val His Pro Ile Leu Arg Thr
        35                  40                  45

Ser His Asn Ser Pro Pro Cys Ser Leu Gln Ala Ile Ser Lys Lys His
    50                  55                  60

Glu Asn Val Ser Trp Leu Ser Val Ser Pro Lys Leu His Val Gln Asn
65                  70                  75                  80

Lys Phe Pro Arg Asp Val Val Arg Ser Glu Leu Thr Ala Ala Gly
                85                  90                  95

Ser Ala Gly Asp Gly Tyr Leu Leu Pro Glu Leu Lys Leu Glu Ser Lys
                100                 105                 110

Val Arg Gly Val Cys Phe Tyr Val Thr Ala Phe Ser Ala Ile Phe
            115                 120                 125

Leu Phe Met Leu Met Leu Val Gly His Pro Ser Val Leu Leu Phe Asp
130                 135                 140

Arg Tyr Arg Arg Met Phe His His Phe Val Ala Lys Val Trp Ala Ala
145                 150                 155                 160

Leu Thr Val Ala Pro Phe Tyr Lys Ile Glu Phe Glu Gly Leu Glu Asn
                165                 170                 175

Leu Pro Pro Pro Asp Thr Pro Ala Val Tyr Val Ser Asn His Gln Ser
            180                 185                 190

Phe Leu Asp Ile Tyr Thr Leu Leu Thr Leu Gly Arg Ser Phe Lys Phe
        195                 200                 205

Ile Ser Lys Thr Gly Ile Phe Leu Phe Pro Ile Ile Gly Trp Ala Met
    210                 215                 220

Phe Leu Leu Gly Val Ile Pro Leu Lys Arg Met Asp Ser Arg Ser Gln
225                 230                 235                 240

Leu Asp Cys Leu Lys Arg Cys Met Asp Leu Ile Lys Lys Gly Ala Ser
                245                 250                 255

Val Phe Phe Phe Pro Glu Gly Thr Arg Ser Lys Asp Gly Lys Leu Gly
            260                 265                 270

Thr Phe Lys Lys Gly Ala Phe Ser Val Ala Ala Lys Thr Asn Ala Pro
        275                 280                 285

Val Val Pro Ile Ser Leu Ile Gly Thr Gly Gln Ile Met Pro Ala Gly
    290                 295                 300

Lys Glu Gly Ile Val Asn Leu Gly Ser Val Lys Val Ile His Lys
305                 310                 315                 320

Pro Ile Val Gly Lys Asp Pro Asp Met Leu Cys Lys Glu Ala Arg Lys
                325                 330                 335

Thr Ile Ala Ser Val Leu Thr Gln Ser
            340                 345
```

<210> SEQ ID NO 20
<211> LENGTH: 344
<212> TYPE: PRT
<213> ORGANISM: Brassica napus

<400> SEQUENCE: 20

```
Met Asp Val Ala Ser Ala Arg Gly Val Ser Ser His Pro Tyr Tyr
1               5                   10                  15

Ser Lys Pro Ile Cys Ser Ser Gln Ser Ser Leu Ile Arg Ile Pro Ile
                20                  25                  30

Ser Lys Gly Cys Cys Phe Ala Arg Ser Ser Asn Leu Ile Thr Ser Leu
            35                  40                  45

His Ala Ala Ser Arg Gly Val Thr Arg Thr Ser Gly Val Gln Trp
    50                  55                  60

Cys Tyr Arg Ser Ile Arg Phe Asp Pro Phe Lys Val Asn Asp Lys Asn
65                  70                  75                  80

Ser Arg Thr Val Thr Val Arg Ser Asp Leu Ser Gly Ala Ala Thr Pro
                85                  90                  95

Glu Ser Thr Tyr Pro Glu Pro Glu Ile Lys Leu Ser Ser Arg Leu Arg
                100                 105                 110

Gly Ile Cys Phe Cys Leu Val Ala Gly Ile Ser Ala Ile Val Leu Ile
            115                 120                 125

Val Leu Met Ile Ile Gly His Pro Phe Val Leu Leu Phe Asp Arg Tyr
130                 135                 140

Arg Arg Lys Phe His His Phe Ile Ala Lys Leu Trp Ala Ser Ile Ser
145                 150                 155                 160

Ile Tyr Pro Phe Tyr Lys Thr Asp Ile Gln Gly Leu Glu Asn Leu Pro
                165                 170                 175

Ser Ser Asp Thr Pro Cys Val Tyr Val Ser Asn His Gln Ser Phe Leu
            180                 185                 190

Asp Ile Tyr Thr Leu Leu Ser Leu Gly Gln Ser Tyr Lys Phe Ile Ser
        195                 200                 205

Lys Thr Gly Ile Phe Val Ile Pro Val Ile Gly Trp Ala Met Ser Met
210                 215                 220

Met Gly Val Val Pro Leu Lys Arg Met Asp Pro Arg Ser Gln Val Asp
225                 230                 235                 240

Cys Leu Lys Arg Cys Met Glu Leu Val Lys Lys Gly Ala Ser Val Phe
                245                 250                 255

Phe Phe Pro Glu Gly Thr Arg Ser Lys Asp Gly Arg Leu Gly Pro Phe
            260                 265                 270

Lys Lys Gly Ala Phe Thr Ile Ala Ala Lys Thr Gly Val Pro Val Val
        275                 280                 285

Pro Ile Thr Leu Met Gly Thr Gly Lys Ile Met Pro Thr Gly Ser Glu
290                 295                 300

Gly Ile Leu Asn His Gly Asp Val Arg Val Ile Ile His Lys Pro Ile
305                 310                 315                 320

Tyr Gly Ser Lys Ala Asp Val Leu Cys Glu Glu Ala Arg Asn Lys Ile
                325                 330                 335

Ala Glu Ser Met Asn Leu Leu Ser
                340
```

<210> SEQ ID NO 21
<211> LENGTH: 356
<212> TYPE: PRT
<213> ORGANISM: Arabidopsis thaliana

<400> SEQUENCE: 21

```
Met Asp Val Ala Ser Ala Arg Ser Ile Ser Ser His Pro Ser Tyr Tyr
1               5                   10                  15
```

Gly Lys Pro Ile Cys Ser Ser Gln Ser Ser Leu Ile Arg Ile Ser Arg
            20                  25                  30

Asp Lys Val Cys Cys Phe Gly Arg Ile Ser Asn Gly Met Thr Ser Phe
        35                  40                  45

Thr Thr Ser Leu His Ala Val Pro Ser Glu Lys Phe Met Gly Glu Thr
    50                  55                  60

Arg Arg Thr Gly Ile Gln Trp Ser Asn Arg Ser Leu Arg His Asp Pro
65                  70                  75                  80

Tyr Arg Phe Leu Asp Lys Lys Ser Pro Arg Ser Ser Gln Leu Ala Arg
                85                  90                  95

Asp Ile Thr Val Arg Ala Asp Leu Ser Gly Ala Ala Thr Pro Asp Ser
            100                 105                 110

Ser Phe Pro Glu Pro Glu Ile Lys Leu Ser Ser Arg Leu Arg Gly Ile
        115                 120                 125

Phe Phe Cys Val Val Ala Gly Ile Ser Ala Thr Phe Leu Ile Val Leu
    130                 135                 140

Met Ile Ile Gly His Pro Phe Val Leu Leu Phe Asp Pro Tyr Arg Arg
145                 150                 155                 160

Lys Phe His His Phe Ile Ala Lys Leu Trp Ala Ser Ile Ser Ile Tyr
                165                 170                 175

Pro Phe Tyr Lys Ile Asn Ile Glu Gly Leu Glu Asn Leu Pro Ser Ser
            180                 185                 190

Asp Thr Pro Ala Val Tyr Val Ser Asn His Gln Ser Phe Leu Asp Ile
        195                 200                 205

Tyr Thr Leu Leu Ser Leu Gly Lys Ser Phe Lys Phe Ile Ser Lys Thr
    210                 215                 220

Gly Ile Phe Val Ile Pro Ile Ile Gly Trp Ala Met Ser Met Met Gly
225                 230                 235                 240

Val Val Pro Leu Lys Arg Met Asp Pro Arg Ser Gln Val Asp Cys Leu
                245                 250                 255

Lys Arg Cys Met Glu Leu Leu Lys Lys Gly Ala Ser Val Phe Phe Phe
            260                 265                 270

Pro Glu Gly Thr Arg Ser Lys Asp Gly Arg Leu Gly Ser Phe Lys Lys
        275                 280                 285

Gly Ala Phe Thr Val Ala Ala Lys Thr Gly Val Ala Val Val Pro Ile
    290                 295                 300

Thr Leu Met Gly Thr Gly Lys Ile Met Pro Thr Gly Ser Glu Gly Ile
305                 310                 315                 320

Leu Asn His Gly Asn Val Arg Val Ile Ile His Lys Pro Ile His Gly
                325                 330                 335

Ser Lys Ala Asp Val Leu Cys Asn Glu Ala Arg Ser Lys Ile Ala Glu
            340                 345                 350

Ser Met Asp Leu
        355

<210> SEQ ID NO 22
<211> LENGTH: 374
<212> TYPE: PRT
<213> ORGANISM: Zea mays

<400> SEQUENCE: 22

Met Ala Ile Pro Leu Val Leu Val Val Leu Pro Leu Gly Leu Leu Phe
1               5                   10                  15

Leu Leu Ser Gly Leu Ile Val Asn Ala Ile Gln Ala Val Leu Phe Val
            20                  25                  30

Thr Ile Arg Pro Phe Ser Lys Ser Phe Tyr Arg Ile Asn Arg Phe
         35                  40                  45

Leu Ala Glu Leu Leu Trp Leu Gln Leu Val Trp Val Asp Trp Trp
 50                  55                  60

Ala Gly Val Lys Val Gln Leu His Ala Asp Glu Thr Tyr Arg Ser
 65                  70                  75                  80

Met Gly Lys Glu His Ala Leu Ile Ile Ser Asn His Arg Ser Asp Ile
                 85                  90                  95

Asp Trp Leu Ile Gly Trp Ile Leu Ala Gln Arg Ser Gly Cys Leu Gly
                100                 105                 110

Ser Thr Leu Ala Val Met Lys Lys Ser Ser Lys Phe Leu Pro Val Ile
             115                 120                 125

Gly Trp Ser Met Trp Phe Ala Glu Tyr Leu Phe Leu Glu Arg Ser Trp
 130                 135                 140

Ala Lys Asp Glu Lys Thr Leu Lys Trp Gly Leu Gln Arg Leu Lys Asp
 145                 150                 155                 160

Phe Pro Arg Pro Phe Trp Leu Ala Leu Phe Val Glu Gly Thr Arg Phe
                 165                 170                 175

Thr Pro Ala Lys Leu Leu Ala Ala Gln Glu Tyr Ala Ala Ser Gln Gly
             180                 185                 190

Leu Pro Ala Pro Arg Asn Val Leu Ile Pro Arg Thr Lys Gly Phe Val
             195                 200                 205

Ser Ala Val Ser Ile Met Arg Asp Phe Val Pro Ala Ile Tyr Asp Thr
 210                 215                 220

Thr Val Ile Val Pro Lys Asp Ser Pro Gln Pro Thr Met Leu Arg Ile
225                 230                 235                 240

Leu Lys Gly Gln Ser Ser Val Ile His Val Arg Met Lys Arg His Ala
                245                 250                 255

Met Ser Glu Met Pro Lys Ser Asp Glu Asp Val Ser Lys Trp Cys Lys
            260                 265                 270

Asp Ile Phe Val Ala Lys Asp Ala Leu Leu Asp Lys His Leu Ala Thr
            275                 280                 285

Gly Thr Phe Asp Glu Glu Ile Arg Pro Ile Gly Arg Pro Val Lys Ser
 290                 295                 300

Leu Leu Val Thr Leu Phe Trp Ser Cys Leu Leu Phe Gly Ala Ile
305                 310                 315                 320

Glu Phe Phe Lys Trp Thr Gln Leu Leu Ser Thr Trp Arg Gly Val Ala
                325                 330                 335

Phe Thr Ala Ala Gly Met Ala Leu Val Thr Gly Val Met His Val Phe
            340                 345                 350

Ile Met Phe Ser Gln Ala Glu Arg Ser Ser Ser Ala Arg Ala Ala Arg
            355                 360                 365

Asn Arg Val Lys Lys Glu
    370

<210> SEQ ID NO 23
<211> LENGTH: 389
<212> TYPE: PRT
<213> ORGANISM: Arabidopsis thaliana

<400> SEQUENCE: 23

Met Val Ile Ala Ala Val Ile Val Pro Leu Gly Leu Leu Phe Phe
 1               5                  10                  15

Ile Ser Gly Leu Ala Val Asn Leu Phe Gln Ala Val Cys Tyr Val Leu

```
            20                  25                  30
Ile Arg Pro Leu Ser Lys Asn Thr Tyr Arg Lys Ile Asn Arg Val Val
                35                  40                  45
Ala Glu Thr Leu Trp Leu Glu Leu Val Trp Ile Val Asp Trp Trp Ala
 50                  55                  60
Gly Val Lys Ile Gln Val Phe Ala Asp Asn Glu Thr Phe Asn Arg Met
 65                  70                  75                  80
Gly Lys Glu His Ala Leu Val Val Cys Asn His Arg Ser Asp Ile Asp
                 85                  90                  95
Trp Leu Val Gly Trp Ile Leu Ala Gln Arg Ser Gly Cys Leu Gly Ser
                100                 105                 110
Ala Leu Ala Val Met Lys Lys Ser Lys Phe Leu Pro Val Ile Gly
                115                 120                 125
Trp Ser Met Trp Phe Ser Glu Tyr Leu Phe Leu Glu Arg Asn Trp Ala
                130                 135                 140
Lys Asp Glu Ser Thr Leu Lys Ser Gly Leu Gln Arg Leu Ser Asp Phe
145                 150                 155                 160
Pro Arg Pro Phe Trp Leu Ala Leu Phe Val Glu Gly Thr Arg Phe Thr
                165                 170                 175
Glu Ala Lys Leu Lys Ala Ala Gln Glu Tyr Ala Ala Ser Ser Glu Leu
                180                 185                 190
Pro Ile Pro Arg Asn Val Leu Ile Pro Arg Thr Lys Gly Phe Val Ser
                195                 200                 205
Ala Val Ser Asn Met Arg Ser Phe Val Pro Ala Ile Tyr Asp Met Thr
                210                 215                 220
Val Thr Ile Pro Lys Thr Ser Pro Pro Thr Met Leu Arg Leu Phe
225                 230                 235                 240
Lys Gly Gln Pro Ser Val His Val His Ile Lys Cys His Ser Met
                245                 250                 255
Lys Asp Leu Pro Glu Ser Asp Asp Ala Ile Ala Gln Trp Cys Arg Asp
                260                 265                 270
Gln Phe Val Ala Lys Asp Ala Leu Leu Asp Lys His Ile Ala Ala Asp
                275                 280                 285
Thr Phe Pro Gly Gln Gln Glu Gln Asn Ile Gly Arg Pro Ile Lys Ser
                290                 295                 300
Leu Ala Val Val Leu Ser Trp Ala Cys Val Leu Thr Leu Gly Ala Ile
305                 310                 315                 320
Lys Phe Leu His Trp Ala Gln Leu Phe Ser Ser Trp Lys Gly Ile Thr
                325                 330                 335
Ile Ser Ala Leu Gly Leu Gly Ile Ile Thr Leu Cys Met Gln Ile Leu
                340                 345                 350
Ile Arg Ser Ser Gln Ser Glu Arg Ser Thr Pro Ala Lys Val Val Pro
                355                 360                 365
Ala Lys Pro Lys Asp Asn His His Pro Glu Ser Ser Ser Gln Thr Glu
                370                 375                 380
Thr Glu Lys Glu Lys
385

<210> SEQ ID NO 24
<211> LENGTH: 376
<212> TYPE: PRT
<213> ORGANISM: Arabidopsis thaliana

<400> SEQUENCE: 24
```

Met Lys Ile Pro Ala Leu Val Phe Ile Pro Val Gly Val Leu Phe
1               5                   10                  15

Leu Ile Ser Gly Leu Ile Val Asn Ile Ile Gln Leu Val Phe Phe Ile
            20                  25                  30

Ile Val Arg Pro Phe Ser Arg Ser Leu Tyr Arg Arg Ile Asn Lys Asn
            35                  40                  45

Val Ala Glu Leu Leu Trp Leu Gln Leu Ile Trp Leu Phe Asp Trp Trp
50                  55                  60

Ala Cys Ile Lys Ile Asn Leu Tyr Val Asp Ala Glu Thr Leu Glu Leu
65                  70                  75                  80

Ile Gly Lys Glu His Ala Leu Val Leu Ser Asn His Arg Ser Asp Ile
                85                  90                  95

Asp Trp Leu Ile Gly Trp Val Met Ala Gln Arg Val Gly Cys Leu Gly
            100                 105                 110

Ser Ser Leu Ala Ile Met Lys Lys Glu Ala Lys Tyr Leu Pro Ile Ile
            115                 120                 125

Gly Trp Ser Met Trp Phe Ser Asp Tyr Ile Phe Leu Glu Arg Ser Trp
            130                 135                 140

Ala Lys Asp Glu Asn Thr Leu Lys Ala Gly Phe Lys Arg Leu Glu Asp
145                 150                 155                 160

Phe Pro Met Thr Phe Trp Leu Ala Leu Phe Val Glu Gly Thr Arg Phe
                165                 170                 175

Thr Gln Glu Lys Leu Glu Ala Ala Gln Glu Tyr Ala Ser Ile Arg Ser
            180                 185                 190

Leu Pro Ser Pro Arg Asn Val Leu Ile Pro Arg Thr Lys Gly Phe Val
            195                 200                 205

Ser Ala Val Ser Glu Ile Arg Ser Phe Val Pro Ala Ile Tyr Asp Cys
210                 215                 220

Thr Leu Thr Val His Asn Asn Gln Pro Thr Pro Thr Leu Leu Arg Met
225                 230                 235                 240

Phe Ser Gly Gln Ser Ser Glu Ile Asn Leu Gln Met Arg Arg His Lys
                245                 250                 255

Met Ser Glu Leu Pro Glu Thr Asp Asp Gly Ile Ala Gln Trp Cys Gln
            260                 265                 270

Asp Leu Phe Ile Thr Lys Asp Ala Gln Leu Glu Lys Tyr Phe Thr Lys
            275                 280                 285

Asp Val Phe Ser Asp Leu Glu Val His Gln Ile Asn Arg Pro Ile Lys
290                 295                 300

Pro Leu Ile Val Val Ile Trp Leu Gly Phe Leu Val Phe Gly Gly
305                 310                 315                 320

Phe Lys Leu Leu Gln Trp Leu Ser Ile Val Ala Ser Trp Lys Ile Ile
                325                 330                 335

Leu Leu Phe Val Phe Phe Leu Val Ile Ala Thr Ile Thr Met Gln Ile
            340                 345                 350

Leu Ile Gln Ser Ser Glu Ser Gln Arg Ser Thr Pro Ala Lys Arg Pro
            355                 360                 365

Leu Gln Glu Gln Leu Ile Ser Ala
    370                 375

<210> SEQ ID NO 25
<211> LENGTH: 390
<212> TYPE: PRT
<213> ORGANISM: Brassica napus

<400> SEQUENCE: 25

Met Ala Met Ala Ala Val Ile Val Pro Leu Gly Ile Leu Phe Phe
1               5                   10                  15

Ile Ser Gly Leu Val Val Asn Leu Leu Gln Ala Val Cys Tyr Val Leu
            20                  25                  30

Val Arg Pro Met Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
50                  55                  60

Gly Val Lys Ile Gln Val Phe Ala Asp Asp Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
                100                 105                 110

Ala Leu Ala Val Met Lys Lys Ser Ser Lys Phe Leu Pro Val Ile Gly
            115                 120                 125

Trp Ser Met Trp Phe Ser Glu Tyr Leu Phe Leu Glu Arg Asn Trp Ala
        130                 135                 140

Lys Asp Glu Ser Thr Leu Gln Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
210                 215                 220

Val Ala Ile Pro Lys Thr Ser Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Pro Glu Asp Glu Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Lys Glu Gln Asn Ile Gly Arg Pro Ile Lys Ser
    290                 295                 300

Leu Ala Val Val Ser Trp Ala Cys Leu Leu Thr Leu Gly Ala Met
305                 310                 315                 320

Lys Phe Leu His Trp Ser Asn Leu Phe Ser Ser Trp Lys Gly Ile Ala
                325                 330                 335

Leu Ser Ala Phe Gly Leu Gly Ile Ile Thr Leu Cys Met Gln Ile Leu
            340                 345                 350

Ile Arg Ser Ser Gln Ser Glu Arg Ser Thr Pro Ala Lys Val Ala Pro
        355                 360                 365

Ala Lys Pro Lys Asp Asn His Gln Ser Gly Pro Ser Ser Gln Thr Glu
    370                 375                 380

Val Glu Glu Lys Gln Lys
385                 390

<210> SEQ ID NO 26
<211> LENGTH: 306

<212> TYPE: PRT
<213> ORGANISM: Prunus dulcis

<400> SEQUENCE: 26

```
Met Gly Lys Glu His Ala Leu Val Ile Ser Asn His Arg Ser Asp Ile
1               5                   10                  15
Asp Trp Leu Val Gly Trp Val Leu Ala Gln Arg Ser Gly Cys Leu Gly
            20                  25                  30
Ser Ser Leu Ala Val Met Lys Lys Ser Ser Lys Phe Leu Pro Val Ile
        35                  40                  45
Gly Trp Ser Met Trp Phe Ser Glu Tyr Leu Phe Leu Glu Arg Ser Trp
    50                  55                  60
Ala Lys Asp Glu Gly Thr Leu Lys Ser Gly Val Gln Arg Leu Lys Asp
65                  70                  75                  80
Phe Pro Gln Pro Phe Trp Leu Ala Leu Phe Val Glu Gly Thr Arg Phe
                85                  90                  95
Thr Gln Ala Lys Leu Leu Ala Ala Gln Glu Tyr Ala Ala Ala Thr Gly
            100                 105                 110
Leu Pro Val Pro Arg Asn Val Leu Ile Pro Arg Thr Lys Gly Phe Val
        115                 120                 125
Thr Ala Val Ser Gln Met Arg Ser Phe Ala Pro Ala Ile Tyr Asp Val
    130                 135                 140
Thr Val Ala Ile Pro Lys Ser Ser Pro Ala Pro Thr Met Leu Arg Leu
145                 150                 155                 160
Phe Glu Gly Arg Pro Ser Val Val His Val His Ile Lys Arg His Val
                165                 170                 175
Met Arg Asp Leu Pro Glu Thr Asp Glu Ala Val Ala Gln Trp Cys Lys
            180                 185                 190
Asp Ile Phe Val Ala Lys Asp Ala Leu Leu Asp Lys His Thr Val Glu
        195                 200                 205
Gln Thr Phe Gly Asp Gln Gln Leu Lys Val Thr Gly Arg Pro Leu Lys
    210                 215                 220
Ser Leu Leu Val Val Thr Ala Trp Ala Cys Leu Leu Ile Leu Gly Ala
225                 230                 235                 240
Leu Lys Phe Leu Tyr Trp Ser Ser Leu Leu Ser Ser Trp Lys Gly Ile
                245                 250                 255
Ala Phe Ser Ala Leu Gly Leu Gly Val Val Thr Val Leu Met Gln Ile
            260                 265                 270
Leu Ile Arg Phe Ser Gln Ser Glu Arg Ser Thr Pro Ala Pro Val Ala
        275                 280                 285
Pro Thr Asn Asn Lys Asn Lys Gly Glu Ser Ser Gly Lys Pro Glu Lys
    290                 295                 300
Gln Gln
305
```

<210> SEQ ID NO 27
<211> LENGTH: 7642
<212> TYPE: DNA
<213> ORGANISM: Artificial Sequence
<220> FEATURE:
<223> OTHER INFORMATION: pSGI-NB55 vector that includes sll1752 LPAAT gene

<400> SEQUENCE: 27

```
cagttaccaa tgcttaatca gtgaggcacc tatctcagcg atctgtctat ttcgttcatc      60
catagttgcc tgactccccg tcgtgtagat aactacgata cgggagggct taccatctgg    120
```

```
ccccagtgct gcaatgatac cgcgagaccc acgctcaccg gctccagatt tatcagcaat    180
aaaccagcca gccggaaggg ccgagcgcag aagtggtcct gcaactttat ccgcctccat    240
ccagtctatt aattgttgcc gggaagctag agtaagtagt tcgccagtta atagtttgcg    300
caactgttgg gaagggcgat cggtgcgggc ctcttcgcta ttacgccagc tggcgaaagg    360
gggatgtgct gcaaggcgat taagttgggt aacgccaggg ttttcccagt cacgacgttg    420
taaaacgacg gccagtgaat tgggcccgac tgcctttggt ggtattaccg atgagtggca    480 cgttatttc accgctctgg ccgtgttgag catggtgctg gcaacgtgg tggctttagc    540 ccaaaccagc atgaaacgga tgttggccta ctcttccatc ggtcaagcag gctttgtgat    600
gattggccta gtggccggca gtgaagatgg ttacgccagc atggttttct acatgctcat    660
ctatctgttt atgaacctgg gggcgtttag ttgcattatt ctcttcaccc tccgcactgg    720
cagtgaccaa attagtgatt acgctggtct gtaccacaaa gacccctt gt taaccttggg    780 cttgagcatt tgtttattat ccttgggggg cattcctcct ctggcgggct ttttcggcaa    840
aatttacatc ttctgggccg gttggcaatc gggattgtat ggcctagtcc tacttggtct    900
ggttaccagt gtagttttcca tctactacta catccgggtg gtgaaaatga tggtggtgaa    960
ggagccccag gaaatgtccg aagtaatcaa aaattacccg gccatcaaat ggaatttacc   1020
cggcatgcgt cccctacagg tgggcattgt cgctactttg gttgctacct cgctggcagg   1080
tattctggct aatccctct ttaacctcgc caccgattc gtggtcagca ccaagatgtt   1140
gcagacagcc ctccagcaaa caggagaaac tccggcgatc gccatttccc atgatttacc   1200 ctagggtat caggaaatat tgctttgcag gcaaaagcca atgagtgtaa ctatagaaac   1260
cgatttaaag gagatccact agtcctgagg ctgaaatgag ctgttgacaa ttaatcatcc   1320
ggctcgtata atgtgtggaa ttgtgagcgg ataacaattt cacactaagg aggaaaaaaa   1380
ccatgaccaa ttctccctg gcgatcgacc ctgctgtcat tggcccttcc agggtttccc   1440
cctggctaat caaattaatt tatcccctag gcaccaggtt tttacattgg tattttggcc   1500
cgatcgccat ccatggtcag gagcattac cccgcagtgg cccgattatt ctggccccta   1560
cccaccgttc ccgttgggat gcaattttgc tttctttggc cgccggtcgg ggggtaactg   1620
gtcgagacct ccgttttatg gtggcggtga cggaagtgca gggtttacag ggttggttta   1680
ttcgccattt gggggattt cccgttgacg tgaaaaggcc ggaaatcagt agtgtgagtt   1740
atagtgtgca gttactccaa gcaggggaaa tgttggtcat ttttcctgag gggggcattt   1800
ttcgggatca acacactgtc catcccctca acggggtat tgggcgcatt gccatggaag   1860
tttgtaagca aaaccccaac actgacatta aagtgatccc agtgacgatc gcctacagtg   1920
acccctaccc aggcaaaggc acttcagtgg aaattaattt tggccagggc atcgccgcta   1980
gggactacga ccccagcacc atcaaggcta gctcccaaaa actgacccgt tgtttggccc   2040
atagaatgca gaacctttac agttccgaga atgtctctct gtgcgaggcg atcgccgctt   2100
cgtgattcta gatatctgca ggcctaagct ttatgcttgt aaaccgtttt gtgaaaaat    2160 ttttaaaata aaaagggga cctctagggt ccccaattaa ttagtaatat aatctattaa   2220
aggtcattca aaaggtcatc caccggatca attcccctgc tcgcgcaggc tgggtgccag   2280
gcccgatcct tggagccctt gccctcccgc acgatgatcg tgccgtgatc gaaatccaga   2340
tccttgaccc gcagttgcaa accctcactg atccgcatgc ccgttccata cagaagctgg   2400
gcgaacaaac gatgctcgcc ttccagaaaa ccgaggatgc gaaccacttc atccggggtc   2460
```

```
agcaccaccg gcaagcgccg cgacggccga ggtcttccga tctcctgaag ccagggcaga    2520
tccgtgcaca gcaccttgcc gtagaagaac agcaaggccg ccaatgcctg acgatgcgtg    2580
gagaccgaaa ccttgcgctc gttcgccagc caggacagaa atgcctcgac ttcgctgctg    2640
cccaaggttg ccgggtgacg cacaccgtgg aaacggatga aggcacgaac ccagtgggaca   2700 taagcctgtt cggttcgtaa gctgtaatgc aagtagcgta tgcgctcacg caactggtcc    2760
agaaccttga ccgaacgcag cggtggtaac ggcgcagtgg cggttttcat ggcttgttat    2820
gactgttttt ttggggtaca gtctatgcct cggtcgggca tccaagcagc aagcgcgtta    2880
cgccgtgggt cgatgtttga tgttatggag cagcaacgat gttacgcagc agggcagtcg    2940
ccctaaaaca aagttaaaca tcatgaggga agcggtgatc gccgaagtat cgactcaact    3000
atcagaggta gttggcgtca tcgagcgcca tctcgaaccg acgttgctgg ccgtacattt    3060
gtacggctcc gcagtggatg gcggcctgaa gccacacagt gatattgatt tgctggttac    3120
ggtgaccgta aggcttgatg aaacaacgcg gcgagctttg atcaacgacc ttttggaaac    3180
ttcggcttcc cctggagaga gcgagattct ccgcgctgta gaagtcacca ttgttgtgca    3240
cgacgacatc attccgtggc gttatccagc taagcgcgaa ctgcaatttg gagaatggca    3300
gcgcaatgac attcttgcag gtatcttcga gccagccacg atcgacattg atctggctat    3360
cttgctgaca aaagcaagag aacatagcgt tgccttggta ggtccagcgg cggaggaact    3420
ctttgatccg gttcctgaac aggatctatt tgaggcgcta aatgaaacct aacgctatg    3480 gaactcgccg cccgactggg ctggcgatga gcgaaatgta gtgcttacgt tgtcccgcat    3540
ttggtacagc gcagtaaccg gcaaaatcgc gccgaaggat gtcgctgccg actgggcaat    3600
ggagcgcctg ccggcccagt atcagcccgt catacttgaa gctagacagg cttatcttgg    3660
acaagaagaa gatcgcttgg cctcgcgcgc agatcagttg gaagaatttg tccactacgt    3720
gaaaggcgag atcaccaagg tagtcggcaa ataatgtcta acaattcgtt caagccgacg    3780
ccgcttcgcg gcgcggctta actcaagcgt tagatgcact aagcacataa ttgctcacag    3840
ccaaactatc aggtcaagtc tgcttttatt attttttaagc gtgcataata agccctacac    3900
aaattgggag atatatcatg aaaggctggc ttttcttgt tatcgcaata gttggcgaag     3960
taatcgcaac atccgcatta aaatctagcg agggctttac taagctgatc cggtggatga    4020 cctttttgaat gacctttaat agattatatt actaattaat tggggaccct agaggtcccc    4080 tttttttattt taaaaatttt ttcacaaaac ggtttacaag cataaagctt ccgcggtacc    4140
cgggaattcg ccctttcaag cttcagatca attcgcgcta acttacatta attgcgttgc    4200
gctcactgcc cgctttccag tcgggaaacc tgtcgtgcca gctgcattaa tgaatcggcc    4260
aacgcgcggg gagaggcggt ttgcgtattg ggcgccaggg tggttttct ttccaccagt     4320 gagacgggca acagctgatt gcccttcacc gcctggccct gagagagttg cagcaagcgg    4380
tccacgctgg tttgccccag caggcgaaaa tcctgtttga tggtggttaa cggcgggata    4440
taacatgagc tgtcttcggt atcgtcgtat cccactaccg agatatccgc accaacgcgc    4500
agcccggact cggtaatggc gcgcattgcg cccagcgcca tctgatcgtt ggcaaccagc    4560
atcgcagtgg gaacgatgcc ctcattcagc atttgcatgg tttgttgaaa accgacatg    4620 gcactccagt cgccttcccg ttccgctatc ggctgaattt gattgcgagt gagatattta    4680
tgccagccag ccagacgcag acgcgccgag acagaactta atgggcccgc taacagcgcg    4740
atttgctggt gacccaatgc gaccagatgc tccacgccca gtcgcgtacc gtcttcatgg    4800
gagaaaataa tactgttgat gggtgtctgg tcagagacat caagaaataa cgccggaaca    4860
```

```
ttagtgcagg cagcttccac agcaatggca tcctggtcat ccagcggata gttaatgatc    4920
agcccactga cgcgttgcgc gagaagattg tgcaccgccg ctttacaggc ttcgacgccg    4980
cttcgttcta ccatcgacac caccacgctg gcacccagtt gatcggcgcg agatttaatc    5040
gccgcgacaa tttgcgacgg cgcgtgcagg gccagactgg aggtggcaac gccaatcagc    5100
aacgactgtt tgcccgccag ttgttgtgcc acgcggttgg gaatgtaatt cagctccgcc    5160
atcgccgctt ccacttttc ccgcgttttc gcagaaacgt ggctggcctg gttcaccacg    5220
cgggaaacgg tctgataaga gacaccggca tactctgcga catcgtataa cgttactggt    5280
ttcacattca ccaccctgaa ttgactctct tccgggcgct atcatgccat accgcgaaag    5340
gttttgcacc attcgatggt gtcaacgtaa atgcatgccg cttcgccttc gcgcaagctt    5400
agaagggcga attccggaca tatggatctt gggggaaatt aagaccaaac tcgatgacct    5460
ccaaaaagat gtaacttctc ttaagatcga tatggcaacg gtgaaaaccg agttatctgc    5520
ggtcaggatg gagataggta cagtcaagga tgatgttaaa gatgtcaaag gcgggctaa    5580 tgctcaaatt tgggcgttga ttcttgccgt catcggagcc ataattacca ccttggtgcg    5640
ttttggcatt ttccctaatc cctaacaaaa aagcgaccag gcttttcttt caattgcccg    5700
atcgcctttg atattttccc aaaggataaa agctagtcca ttcagaatcg agccttaaag    5760
tactcccata ttggctagcc ccagaattac tccagcgccg aggatgtggc caaagctagc    5820
ggtgcccagc acagccccta aaccaaagcc gccaagaag ttagaggaag catgggggt    5880 gcccacattt tgttgtttga tggtcaattt accaaaggcg atcgccaaaa tgttgcaagc    5940
aatcatcacc ccagcaactt tagggctcca ggacagggtg gcgggaacgg cggtggccaa    6000
caaaaagcta tgcattgaga ttctccagaa taaagacggt ttttaaaggg atagccccac    6060
gctaatgggg gtctttaaaa atctcatctt acggggacgc tctgcccctg ggaaaccacc    6120
gttgcaatac ttaacaaatt ttcgttttta gcttggcaaa tgtctttggc aaaattggtt    6180
gatctggctt aaatcgtcag ttatttgccc tggaatagtc tggggacggg caattctgat    6240
cagatttacc cccaacgctt ccgccacttt ttgcttaacc aattctcccc cctgggcacc    6300
ggaggcttta gttaccaccc cttgaatttg ccattgttgc cacagggctt tttccaatgg    6360
ttcggctacg ggggggcgca aagcaatgat acggtcggaa gtaaacccag cggcgatcgc    6420
ctgggctagg cttggggat agggcagaat acgggcaaat agggcccagc ttggcgtaat    6480
catggtcata gctgtttcct gtgtgaaatt gttatccgct cacaattcca cacaacatac    6540
gagccggaag cataaagtgt aaagcctggg gtgcctaatg agtgagctaa ctcacattaa    6600
ttgcgttgcg ctcactgccc gctttccagt cgggaaacct gtcgtgccag ctgcattaat    6660
gaatcggcca acgcgcgggg agaggcggtt tgcgtattgg gcgctcttcc gcttcctcgc    6720
tcactgactc gctgcgctcg gtcgttcggc tgcggcgagc ggtatcagct cactcaaagg    6780
cggtaatacg gttatccaca gaatcagggg ataacgcagg aaagaacatg tgagcaaaag    6840
gccagcaaaa ggccaggaac cgtaaaaagg ccgcgttgct ggcgtttttc cataggctcc    6900
gcccccctga cgagcatcac aaaaatcgac gctcaagtca gaggtggcga aacccgacag    6960
gactataaag ataccaggcg tttccccctg gaagctccct cgtgcgctct cctgttccga    7020 cctgccgct taccggatac ctgtccgcct ttctcccttc gggaagcgtg gcgctttctc    7080
atagctcacg ctgtaggtat ctcagttcgg tgtaggtcgt tcgctccaag ctgggctgtg    7140
tgcacgaacc ccccgttcag cccgaccgct gcgccttatc cggtaactat cgtcttgagt    7200
```

| | | |
|---|---|---|
| ccaacccggt aagacacgac ttatcgccac tggcagcagc cactggtaac aggattagca | 7260 |
| gagcgaggta tgtaggcggt gctacagagt tcttgaagtg gtggcctaac tacggctaca | 7320 |
| ctagaaggac agtatttggt atctgcgctc tgctgaagcc agttaccttc ggaaaaagag | 7380 |
| ttggtagctc ttgatccggc aaacaaacca ccgctggtag cggtggtttt tttgtttgca | 7440 |
| agcagcagat tacgcgcaga aaaaaggat ctcaagaaga tcctttgatc ttttctacgg | 7500 |
| ggtctgacgc tcagtggaac gaaaactcac gttaagggat tttggtcatg agattatcaa | 7560 |
| aaaggatctt cacctagatc cttttaaatt aaaaatgaag ttttaaatca atctaaagta | 7620 |
| tatatgagta aacttggtct ga | 7642 |

<210> SEQ ID NO 28
<211> LENGTH: 90
<212> TYPE: DNA
<213> ORGANISM: Artificial Sequence
<220> FEATURE:
<223> OTHER INFORMATION: TrcY promoter

<400> SEQUENCE: 28

| | |
|---|---|
| ctgaaatgag ctgttgacaa ttaatcatcc ggctcgtata atgtgtggaa ttgtgagcgg | 60 |
| ataacaattt cacactaagg aggaaaaaaa | 90 |

<210> SEQ ID NO 29
<211> LENGTH: 39
<212> TYPE: DNA
<213> ORGANISM: Artificial Sequence
<220> FEATURE:
<223> OTHER INFORMATION: Primer NB395

<400> SEQUENCE: 29

| | |
|---|---|
| cactaaggag gaaaaaaaat gaccaattct cccctggcg | 39 |

<210> SEQ ID NO 30
<211> LENGTH: 34
<212> TYPE: DNA
<213> ORGANISM: Artificial Sequence
<220> FEATURE:
<223> OTHER INFORMATION: Primer NB396

<400> SEQUENCE: 30

| | |
|---|---|
| cctgcagata tctagaatca cgaagcggcg atcg | 34 |

<210> SEQ ID NO 31
<211> LENGTH: 8572
<212> TYPE: DNA
<213> ORGANISM: Artificial Sequence
<220> FEATURE:
<223> OTHER INFORMATION: YC63 expression/integration vector

<400> SEQUENCE: 31

| | |
|---|---|
| cagttaccaa tgcttaatca gtgaggcacc tatctcagcg atctgtctat ttcgttcatc | 60 |
| catagttgcc tgactccccg tcgtgtagat aactacgata cgggagggct taccatctgg | 120 |
| ccccagtgct gcaatgatac cgcgagaccc acgctcaccg gctccagatt tatcagcaat | 180 |
| aaaccagcca gccggaaggg ccgagcgcag aagtggtcct gcaactttat ccgcctccat | 240 |
| ccagtctatt aattgttgcc gggaagctag agtaagtagt tcgccagtta atagtttgcg | 300 |
| caactgttgg gaagggcgat cggtgcgggc ctcttcgcta ttacgccagc tggcgaaagg | 360 |
| gggatgtgct gcaaggcgat taagttgggt aacgccaggt tttcccagt cacgacgttg | 420 |
| taaaacgacg gccagtgaat tgggcccgac tgcctttggt ggtattaccg atgagtggca | 480 |

```
cgttattttc accgctctgg ccgtgttgag catggtgctg ggcaacgtgg tggctttagc      540
ccaaaccagc atgaaacgga tgttggccta ctcttccatc ggtcaagcag gctttgtgat      600
gattggccta gtggccggca gtgaagatgg ttacgccagc atggttttct acatgctcat      660
ctatctgttt atgaacctgg gggcgtttag ttgcattatt ctcttcaccc tccgcactgg      720
cagtgaccaa attagtgatt acgctggtct gtaccacaaa gacccttgt taaccttggg       780 cttgagcatt tgtttattat ccttgggggg cattcctcct ctggcgggct ttttcggcaa      840
aatttacatc ttctgggccg gttggcaatc gggattgtat ggcctagtcc tacttggtct      900
ggttaccagt gtagtttcca tctactacta catcccgggtg tgaaaatga tggtggtgaa     960 ggagccccag gaaatgtccg aagtaatcaa aaatttacccg gccatcaaat ggaatttacc    1020
cggcatgcgt cccctacagg tgggcattgt cgctactttg gttgctacct cgctggcagg    1080
tattctggct aatccccttct ttaacctcgc caccgattcc gtggtcagca ccaagatgtt    1140
gcagacagcc ctccagcaaa caggagaaac tccggcgatc gccatttccc atgatttacc    1200
ctaggggtat caggaaatat tgctttgcag gcaaaagcca atgagtgtaa ctatagaaac    1260
cgatttaaag gagatccact agtcctgagg ctgaaatgag ctgttgacaa ttaatcatcc    1320
ggctcgtata atgtgtggaa ttgtgagcgg ataacaattt cacactaagg aggaaaaaaa    1380
ccatggaaga cgccaaaaac ataaagaaag gcccggcgcc attctatccg ctggaagatg    1440
gaaccgctgg agagcaactg cataaggcta tgaagagata cgccctggtt cctggaacaa    1500
ttgcttttac agatgcacat atcgaggtgg acatcactta cgctgagtac ttcgaaatgt    1560
ccgttcggtt ggcagaagct atgaaacgat atgggctgaa tacaaatcac agaatcgtcg    1620
tatgcagtga aaactctctt caattctttta tgccggtgtt gggcgcgtta tttatcggag    1680
ttgcagttgc gcccgcgaac gacatttata atgaacgtga attgctcaac agtatgggca    1740
tttcgcagcc taccgtggtg ttcgtttcca aaaaggggtt gcaaaaaatt ttgaacgtgc    1800
aaaaaaagct cccaatcatc caaaaaatta ttatcatgga ttctaaaacg gattaccagg    1860
gatttcagtc gatgtacacg ttcgtcacat ctcatctacc tcccggtttt aatgaatacg    1920
attttgtgcc agagtccttc gatagggaca agacaattgc actgatcatg aactcctctg    1980
gatctactgg tctgcctaaa ggtgtcgctc tgcctcatag aactgcctgc gtgagattct    2040
cgcatgccag agatcctatt tttggcaatc aaatcattcc ggatactgcg attttaagtg    2100
ttgttccatt ccatcacggt tttggaatgt ttactacact cggatatttg atatgtggat    2160
ttcgagtcgt cttaatgtat agatttgaag aagagctgtt tctgaggagc cttcaggatt    2220
acaagattca agtgcgctg ctggtgccaa ccctattctc cttcttcgcc aaaagcactc     2280
tgattgacaa atacgattta tctaatttac acgaaattgc ttctggtggc gctcccctct    2340
ctaaggaagt cggggaagcg gttgccaaga ggttccatct gccaggtatc aggcaaggat    2400
atgggctcac tgagactaca tcagctattc tgattacacc cgaggggat gataaaccgg    2460 gcgcggtcgg taaagttgtt ccattttttg aagcgaaggt tgtggatctg gataccggga    2520
aaacgctggg cgttaatcaa agaggcgaac tgtgtgtgag aggtcctatg attatgtccg    2580
gttatgtaaa caatccggaa gcgaccaacg ccttgattga caaggatgga tggctacatt    2640
ctggagacat agcttactgg gacgaagacg aacacttctt catcgttgac cgcctgaagt    2700
ctctgattaa gtacaaaggc tatcaggtgg ctcccgctga attggaatcc atcttgctcc    2760 aacacccca catcttcgac gcaggtgtcg caggtcttcc cgacgatgac gccggtgaac    2820
```

```
ttcccgccgc cgttgttgtt ttggagcacg gaaagacgat gacggaaaaa gagatcgtgg    2880
attacgtcgc cagtcaagta acaaccgcga aaaagttgcg cggaggagtt gtgtttgtgg    2940
acgaagtacc gaaaggtctt accggaaaac tcgacgcaag aaaaatcaga gagatcctca    3000
taaaggccaa gaagggcgga agatcgccg tgtaattcta gatatctgca ggcctaagct     3060
ttatgcttgt aaaccgtttt gtgaaaaaat ttttaaaata aaaaggggga cctctagggt    3120
ccccaattaa ttagtaatat aatctattaa aggtcattca aaaggtcatc caccggatca    3180
attcccctgc tcgcgcaggc tgggtgccag gcccgatcct tggagccctt gccctcccgc    3240
acgatgatcg tgccgtgatc gaaatccaga tccttgaccc gcagttgcaa accctcactg    3300
atccgcatgc ccgttccata cagaagctgg gcgaacaaac gatgctcgcc ttccagaaaa    3360
ccgaggatgc gaaccacttc atccggggtc agcaccaccg gcaagcgccg cgacggccga    3420
ggtcttccga tctcctgaag ccagggcaga tccgtgcaca gcaccttgcc gtagaagaac    3480
agcaaggccg ccaatgcctg acgatgcgtg agaccgaaa ccttgcgctc gttcgccagc     3540
caggacagaa atgcctcgac ttcgctgctg cccaaggttg ccgggtgacg cacaccgtgg    3600
aaacggatga aggcacgaac ccagtggaca taagcctgtt cggttcgtaa gctgtaatgc    3660
aagtagcgta tgcgctcacg caactggtcc agaaccttga ccgaacgcag cggtggtaac    3720
ggcgcagtgg cggttttcat ggcttgttat gactgttttt ttggggtaca gtctatgcct    3780
cggtcgggca tccaagcagc aagcgcgtta cgccgtgggt cgatgtttga tgttatggag    3840
cagcaacgat gttacgcagc agggcagtcg ccctaaaaca aagttaaaca tcatgaggga    3900
agcggtgatc gccgaagtat cgactcaact atcagaggta gttggcgtca tcgagcgcca    3960
tctcgaaccg acgttgctgg ccgtacattt gtacggctcc gcagtggatg gcggcctgaa    4020
gccacacagt gatattgatt tgctggttac ggtgaccgta aggcttgatg aaacaacgcg    4080
gcgagctttg atcaacgacc ttttggaaac ttcggcttcc cctggagaga gcgagattct    4140
ccgcgctgta gaagtcacca ttgttgtgca cgacgacatc attccgtggc gttatccagc    4200
taagcgcgaa ctgcaatttg gagaatggca gcgcaatgac attcttgcag gtatcttcga    4260
gccagccacg atcgacattg atctggctat cttgctgaca aaagcaagag aacatagcgt    4320
tgccttggta ggtccagcgg cggaggaact ctttgatccg gttcctgaac aggatctatt    4380
tgaggcgcta aatgaaacct taacgctatg gaactcgccg cccgactggg ctggcgatga    4440
gcgaaatgta gtgcttacgt tgtcccgcat ttggtacagc gcagtaaccg gcaaaatcgc    4500
gccgaaggat gtcgctgccg actgggcaat ggagcgcctg ccggcccagt atcagcccgt    4560
catacttgaa gctagacagg cttatcttgg acaagaagaa gatcgcttgg cctcgcgcgc    4620
agatcagttg gaagaatttg tccactacgt gaaaggcgag atcaccaagg tagtcggcaa    4680
ataatgtcta acaattcgtt caagccgacg ccgcttcgcg gcgcggctta actcaagcgt    4740
tagatgcact aagcacataa ttgctcacag ccaaactatc aggtcaagtc tgcttttatt    4800
atttttaagc gtgcataata agccctacac aaattgggag atatatcatg aaaggctggc    4860
tttttcttgt tatcgcaata gttggcgaag taatcgcaac atccgcatta aaatctagcg    4920
agggctttac taagctgatc cggtggatga ccttttgaat gacctttaat agattatatt    4980
actaattaat tggggaccct agaggtcccc ttttttattt taaaaatttt ttcacaaaac    5040
ggtttacaag cataaagctt ccgcggtacc cgggaattcg ccctttcaag cttcagatca    5100
attcgcgcta acttacatta attgcgttgc gctcactgcc cgctttccag tcgggaaacc    5160
tgtcgtgcca gctgcattaa tgaatcggcc aacgcgcggg gagaggcggt ttgcgtattg    5220
```

```
ggcgccaggg tggttttttct tttcaccagt gagacgggca acagctgatt gcccttcacc    5280
gcctggccct gagagagttg cagcaagcgg tccacgctgg tttgcccag caggcgaaaa     5340 tcctgtttga tggtggttaa cggcgggata taacatgagc tgtcttcggt atcgtcgtat    5400
cccactaccg agatatccgc accaacgcgc agcccggact cggtaatggc gcgcattgcg    5460
cccagcgcca tctgatcgtt ggcaaccagc atcgcagtgg aacgatgcc ctcattcagc     5520 atttgcatgg tttgttgaaa accggacatg cactccagt cgccttcccg ttccgctatc     5580
ggctgaattt gattgcgagt gagatattta tgccagccag ccagacgcag acgcgccgag    5640
acagaactta atgggcccgc taacagcgcg atttgctggt gacccaatgc gaccagatgc    5700
tccacgccca gtcgcgtacc gtcttcatgg gagaaaataa tactgttgat gggtgtctgg    5760
tcagagacat caagaaataa cgccggaaca ttagtgcagg cagcttccac agcaatggca    5820
tcctggtcat ccagcggata gttaatgatc agcccactga cgcgttgcgc gagaagattg    5880
tgcaccgccg ctttacaggc ttcgacgccg cttcgttcta ccatcgacac caccacgctg    5940
gcacccagtt gatcggcgcg agatttaatc gccgcgacaa tttgcgacgg cgcgtgcagg    6000
gccagactgg aggtggcaac gccaatcagc aacgactgtt tgcccgccag ttgttgtgcc    6060
acgcggttgg gaatgtaatt cagctccgcc atcgccgctt ccacttttc ccgcgttttc      6120 gcagaaacgt ggctggcctg gttcaccacg cgggaaacgg tctgataaga gacaccggca    6180
tactctgcga catcgtataa cgttactggt ttcacattca ccaccctgaa ttgactctct    6240
tccgggcgct atcatgccat accgcgaaag gttttgcacc attcgatggt gtcaacgtaa    6300
atgcatgccg cttcgccttc gcgcaagctt agaagggcga attccggaca tatggatctt    6360
gggggaaatt aagaccaaac tcgatgacct ccaaaaagat gtaacttctc ttaagatcga    6420 tatgcaacg gtgaaaaccg agttatctgc ggtcaggatg gagataggta cagtcaagga    6480
tgatgttaaa gatgtcaaag ggcgggctaa tgctcaaatt tgggcgttga ttcttgccgt    6540
catcggagcc ataattacca ccttggtgcg ttttggcatt ttccctaatc cctaacaaaa    6600
aagcgaccag gcttttcttt caattgcccg atcgcctttg atattttccc aaaggataaa    6660
agctagtcca ttcagaatcg agccttaaag tactcccata ttggctagcc ccagaattac    6720
tccagcgccg aggatgtggc caaagctagc ggtgcccagc acagccccta aaccaaagcc    6780
gccaaagaag ttagaggaag gcatgggggt gcccacattt tgttgtttga tggtcaattt    6840
accaaaggcg atcgccaaaa tgttgcaagc aatcatcacc ccagcaactt tagggctcca    6900
ggacagggtg gcgggaacgg cggtggccaa caaaaagcta tgcattgaga ttctccagaa    6960
taaagacggt ttttaagggg atagccccac gctaatgggg gtctttaaaa atctcatctt    7020
acggggacgc tctgccctg ggaaccaccg gttgcaatac ttaacaaatt ttcgttttta      7080
gcttggcaaa tgtctttggc aaaattggtt gatctggctt aaatcgtcag ttatttgccc    7140
tggaatagtc tggggacggg caattctgat cagatttacc cccaacgctt ccgccacttt    7200
ttgcttaacc aattctcccc cctgggcacc ggaggcttta gttaccaccc cttgaatttg    7260
ccattgttgc cacagggctt tttccaatgg ttcggctacg gggggggcgca aagcaatgat    7320 acggtcggaa gtaaacccag cggcgatcgc ctgggctagg gcttggggat agggcagaat    7380
acgggcaaat agggcccagc ttggcgtaat catggtcata gctgtttcct gtgtgaaatt    7440
gttatccgct cacaattcca cacaacatac gagccggaag cataaagtgt aaagcctggg    7500
gtgcctaatg agtgagctaa ctcacattaa ttgcgttgcg ctcactgccc gctttccagt    7560
```

```
cgggaaacct gtcgtgccag ctgcattaat gaatcggcca acgcgcgggg agaggcggtt    7620
tgcgtattgg gcgctcttcc gcttcctcgc tcactgactc gctgcgctcg gtcgttcggc    7680
tgcggcgagc ggtatcagct cactcaaagg cggtaatacg gttatccaca gaatcagggg    7740
ataacgcagg aaagaacatg tgagcaaaag gccagcaaaa ggccaggaac cgtaaaaagg    7800
ccgcgttgct ggcgtttttc cataggctcc gcccccctga cgagcatcac aaaaatcgac    7860
gctcaagtca gaggtggcga aacccgacag gactataaag ataccaggcg tttccccctg    7920
gaagctccct cgtgcgctct cctgttccga ccctgccgct taccggatac ctgtccgcct    7980
ttctcccttc gggaagcgtg gcgctttctc atagctcacg ctgtaggtat ctcagttcgg    8040
tgtaggtcgt tcgctccaag ctgggctgtg tgcacgaacc ccccgttcag cccgaccgct    8100
gcgccttatc cggtaactat cgtcttgagt ccaacccggt aagacacgac ttatcgccac    8160
tggcagcagc cactggtaac aggattagca gagcgaggta tgtaggcggt gctacagagt    8220
tcttgaagtg gtggcctaac tacggctaca ctagaaggac agtatttggt atctgcgctc    8280
tgctgaagcc agttaccttc ggaaaaagag ttggtagctc ttgatccggc aaacaaacca    8340
ccgctggtag cggtggtttt tttgtttgca agcagcagat tacgcgcaga aaaaaggat    8400 ctcaagaaga tcctttgatc ttttctacgg gtctgacgc tcagtggaac gaaaactcac    8460
gttaagggat tttggtcatg agattatcaa aaaggatctt cacctagatc cttttaaatt    8520
aaaaatgaag ttttaaatca atctaaagta tatatgagta aacttggtct ga            8572

<210> SEQ ID NO 32
<211> LENGTH: 1032
<212> TYPE: DNA
<213> ORGANISM: Synechocystis PCC6803

<400> SEQUENCE: 32
tatttgcccg tattctgccc tatccccaag ccctagccca ggcgatcgcc gctgggttta      60
cttccgaccg tatcattgct ttgcgccccc ccgtagccga accattggaa aaagccctgt     120
ggcaacaatg gcaaattcaa ggggtggtaa ctaaagcctc cggtgcccag gggggagaat     180
tggttaagca aaaagtggcg gaagcgttgg gggtaaatct gatcagaatt gcccgtcccc     240
agactattcc agggcaaata actgacgatt taagccagat caaccaattt tgccaaagac     300
atttgccaag ctaaaaacga aaatttgtta agtattgcaa cggtggtttc ccaggggcag     360
agcgtccccg taagatgaga ttttaaaga ccccccattag cgtggggcta tccctttaaa    420 aaccgtctttt attctggaga atctcaatgc atagcttttt gttggccacc gccgttcccg     480
ccaccctgtc ctggagccct aaagttgctg gggtgatgat tgcttgcaac attttggcga     540
tcgcctttgg taaattgacc atcaaacaac aaaatgtggg cacccccatg ccttcctcta     600
acttctttgg cggctttggt ttaggggctg tgctgggcac cgctagcttt ggccacatcc     660
tcggcgctgg agtaattctg gggctagcca atatgggagt actttaaggc tcgattctga     720
atggactagc tttatccttt tgggaaaata tcaaggcga tcgggcaatt gaaagaaaag     780
cctggtcgct ttttgttag ggattaggga aaatgccaaa acgcaccaag gtggtaatta     840
tggctccgat gacggcaaga atcaacgccc aaatttgagc attagcccgc cctttgacat     900
ctttaacatc atccttgact gtacctatct ccatcctgac cgcagataac tcggttttca     960
ccgttgccat atcgatctta agagaagtta catcttttg gaggtcatcg agtttggtct    1020
taatttcccc ca                                                         1032
```

```
<210> SEQ ID NO 33
<211> LENGTH: 824
<212> TYPE: DNA
<213> ORGANISM: Synechocystis PCC6803

<400> SEQUENCE: 33
cctttaaatc ggtttctata gttacactca ttggcttttg cctgcaaagc aatatttcct      60
gataccccta gggtaaatca tgggaaatgg cgatcgccgg agtttctcct gtttgctgga     120
gggctgtctg caacatcttg gtgctgacca cggaatcggt ggcgaggtta aagaggggat     180
tagccagaat acctgccagc gaggtagcaa ccaaagtagc gacaatgccc acctgtaggg     240
gacgcatgcc gggtaaattc catttgatgg ccgggtaatt tttgattact tcggacattt     300
cctggggctc cttcaccacc atcattttca ccacccggat gtagtagtag atggaaacta     360
cactggtaac cagaccaagt aggactaggc catacaatcc cgattgccaa ccggcccaga     420
agatgtaaat tttgccgaaa agcccgcca  gaggaggaat gcccccaag  gataataaac     480 aaatgctcaa gcccaaggtt aacaagggggt ctttgtggta cagaccagcg taatcactaa     540
tttggtcact gccagtgcgg agggtgaaga gaataatgca actaaacgcc cccaggttca     600
taaacagata gatgagcatg tagaaaacca tgctggcgta accatcttca ctgccggcca     660
ctaggccaat catcacaaag cctgcttgac cgatggaaga gtaggccaac atccgtttca     720
tgctggtttg ggctaaagcc accacgttgc ccagcaccat gctcaacacg gccagagcgg     780
tgaaaataac gtgccactca tcggtaatac caccaaaggc agtc                      824

<210> SEQ ID NO 34
<211> LENGTH: 31
<212> TYPE: DNA
<213> ORGANISM: Artificial Sequence
<220> FEATURE:
<223> OTHER INFORMATION: Primer NB393

<400> SEQUENCE: 34
ttctagatat ctgcaggcct aagctttatg c                                    31

<210> SEQ ID NO 35
<211> LENGTH: 34
<212> TYPE: DNA
<213> ORGANISM: Artificial Sequence
<220> FEATURE:
<223> OTHER INFORMATION: Primer NB394

<400> SEQUENCE: 35 ttttttttcct ccttagtgtg aaattgttat ccgc                                34

<210> SEQ ID NO 36
<211> LENGTH: 6414
<212> TYPE: DNA
<213> ORGANISM: Artificial Sequence
<220> FEATURE:
<223> OTHER INFORMATION: pSGI-NB158 vector

<400> SEQUENCE: 36
cctgaggctg aaatgagctg ttgacaatta atcatccggc tcgtataatg tgtggaattg      60
tgagcggata caatttcac  actaaggagg aaaaaaacca tggcgaacgg tagcgctgtc     120
tctctgaaga gcggctcctt gaatacgcaa gaggacactt cttcttcccc accgccacgc     180
gcgttcatca accaattacc cgactggtcc atgttattga cggcgattac cactgtcttt     240
gttgccgcag agaaacagtg gactatgtta gaccgcaaga gcaagcgctc cgatatgtta     300
```

```
gtggattctt ttggcatgga acgcattgtg caggatggct tagtgtttcg tcaatctttt    360
agcattcgtt cttatgaaat cggtgcagat cgtcgtgcat ccattgaaac cttaatgaac    420
catctgcagg aaactagctt gaatcattgc aaatccattc gcttgttgaa tgagggtttt    480
ggtcgcaccc ccgagatgtg caaacgtgac ttgatctggg tggttacccg catgcacatc    540
atggtcaacc gctaccctac ctggggtgat accgttgaga ttaacacttg ggtttcccaa    600
agcggcaaga atggtatggg tcgtgattgg ctgatttccg actgtaatac cggcgaaatc    660
ctgatccgcg cgacgtctgc atgggcgatg atgaaccaaa agacccgtcg tctgtctaaa    720
ctgccttacg aagtcagcca agagattgct ccgcacttcg tcgacagccc tcccgtgatc    780
gaggacggcg accgtaagtt acacaagttc gatgtgaaaa ccggcgacag catccgtaaa    840
ggtttgactc cgcgttggaa tgacttagat gttaatcagc acgttaacaa cgttaagtat    900
atcggctgga tcttagagag catgccgacc gaggtcttgg aaactcatga actgtgtttc    960
ttaactctgg agtatcgtcg cgagtgcggt cgcgatagcg tgctggaatc tgtgaccgcg   1020
atggatcctt ctaatgaagg tggtcgctcc cactaccagc atttactgcg cttggaggac   1080
ggtactgaca tcgttaaggg ccgcactgag tggcgtccaa agaatgcccg gaatattggt   1140
gccattagta ccggtaaaac cagtaatggt aatcccgcca gttaataacc tttcaagctt   1200
cagatcaatt cgcgctaact tacattaatt gcgttgcgct cactgcccgc tttccagtcg   1260
ggaaacctgt cgtgccagct gcattaatga atcggccaac gcgcggggag aggcggtttg   1320
cgtattgggc gccagggtgg ttttccttt caccagtgag acgggcaaca gctgattgcc   1380
cttcaccgcc tggccctgag agagttgcag caagcggtcc acgctggttt gccccagcag   1440
gcgaaaatcc tgtttgatgg tggttaacgg cgggatataa catgagctgt cttcggtatc   1500
gtcgtatccc actaccgaga tatccgcacc aacgcgcagc ccggactcgg taatggcgcg   1560
cattgcgccc agcgccatct gatcgttggc aaccagcatc gcagtgggaa cgatgccctc   1620
attcagcatt tgcatggttt gttgaaaacc ggacatggca ctccagtcgc cttcccgttc   1680
cgctatcggc tgaatttgat tgcgagtgag atatttatgc cagccagcca gacgcagacg   1740
cgccgagaca gaacttaatg ggcccgctaa cagcgcgatt tgctggtgac ccaatgcgac   1800
cagatgctcc acgcccagtc gcgtaccgtc ttcatgggag aaaataatac tgttgatggg   1860
tgtctggtca gagacatcaa gaaataacgc cggaacatta gtgcaggcag cttccacagc   1920
aatggcatcc tggtcatcca gcggatagtt aatgatcagc ccactgacgc gttgcgcgag   1980
aagattgtgc accgccgctt tacaggcttc gacgccgctt cgttctacca tcgacaccac   2040
cacgctggca cccagttgat cggcgcgaga tttaatcgcc gcgacaattt gcgacggcgc   2100
gtgcagggcc agactggagg tggcaacgcc aatcagcaac gactgtttgc ccgccagttg   2160
ttgtgccacg cggttgggaa tgtaattcag ctccgccatc gccgcttcca ctttttcccg   2220
cgttttcgca gaaacgtggc tggcctggtt caccacgcgg gaaacggtct gataagagac   2280
accggcatac tctgcgacat cgtataacgt tactggtttc acattcacca ccctgaattg   2340
actctcttcc gggcgctatc atgccatacc gcgaaaggtt ttgcaccatt cgatggtgtc   2400
aacgtaaatg catgccgctt cgccttcgcg caagcttaga agggcgaatt ccggaccaca   2460
agataaaaat atatcatcat gaacaataaa actgtctgct tacataaaca gtaatacaag   2520
gggtgttatg agccatattc aacgggaaac gtcttgctcg aggccgcgat taaattccaa   2580
catggatgct gatttatatg ggtataaatg ggctcgcgat aatgtcgggc aatcaggtgc   2640
gacaatctat cgattgtatg ggaagcccga tgcgccagag ttgtttctga acatggcaa    2700
```

-continued

```
aggtagcgtt gccaatgatg ttacagatga gatggtcaga ctaaactggc tgacggaatt     2760
tatgcctctt ccgaccatca agcatttat ccgtactcct gatgatgcat ggttactcac      2820
cactgcgatc cccgggaaaa cagcattcca ggtattagaa gaatatcctg attcaggtga    2880
aaatattgtt gatgcgctgg cagtgttcct gcgccggttg cattcgattc ctgtttgtaa    2940
ttgtcctttt aacagcgatc gcgtatttcg tctcgctcag gcgcaatcac gaatgaataa    3000
cggtttggtt gatgcgagtg attttgatga cgagcgtaat ggctggcctg ttgaacaagt    3060
ctggaaagaa atgcataagc ttttgccatt ctcaccggat tcagtcgtca ctcatggtga    3120
tttctcactt gataaccta ttttgacga ggggaaatta ataggttgta ttgatgttgg      3180
acgagtcgga atcgcagacc gataccagga tcttgccatc ctatggaact gcctcggtga   3240
gttttctcct tcattacaga aacggctttt tcaaaaatat ggtattgata atcctgatat    3300
gaataaattg cagtttcatt tgatgctcga tgagtttttc taatcagaat tggttaattg    3360
gttgtaacac tggcagagca ttacgctgac ttgacgggac ggcggcccgg tatggatggc   3420
accgatgcgg aatcccaaca gattgccttt gacaacaatg tggcctggaa taacctgggg  3480
gatttgtcca ccaccaccca acgggcctac acttcggcta ttagcacaga cacagtgcag   3540
agtgtttatg gcgttaatct ggaaaaaaac gataacattc ccattgtttt tgcgtggccc   3600
attttttccca ccacccttaa tcccacagat tttcaggtaa tgcttaacac ggggggaaatt 3660
gtcaccccgg tgatcgcctc tttgattccc aacagtgaat acaacgaacg gcaaacggta   3720
gtaattacgg gcaattttgg taatcgttta accccaggca cggagggagc gatttatccc   3780
gtttccgtag gcacagtgtt ggacagtact cctttggaaa tggtgggacc caacggcccg   3840
gtcagtgcgg tgggtattac cattgatagt ctcaacccct acgtggccgg caatggtccc   3900
aaaattgtcg ccgctaagtt agaccgcttc agtgacctgg gggaaggggc tcccctctgg   3960
ttagccacca atcaaaataa cagtggcggg gatttatatg gagaccaagc ccaatttcgt   4020
ttgcgaattt acaccagcgc cggtttttcc cccgatggca ttgccagttt actacccaca   4080
gaatttgaac ggtatttca actccaagcg gaagatatta cgggacggac agttatccta    4140
acccaaactg gtgttgatta tgaaattccc ggctttggtc tggtgcaggt gttggggctg   4200
gcggatttgg ccggggttca ggacagctat gacctgactt acatcgaaga tcatgacaac   4260
tattacgaca ttatcctcaa aggggacgaa gccgcagttc gccaaattaa gagggttgct   4320
ttgccctccg aaggggatta ttcggcggtt tataatcccg gtggccccgg caatgatcca   4380
gagaatggtc cccatgttc agctactgac ggggtggtgc gtaacggcaa aagcaccgcc    4440
ggacatcagc gctagcggag tgtatactgg cttactatgt tggcactgat gagggtgtca   4500
gtgaagtgct tcatgtggca ggagaaaaaa ggctgcaccg gtgcgtcagc agaatatgtg   4560
atacaggata tattccgctt cctcgctcac tgactcgcta cgctcggtcg ttcgactgcg   4620
gcgagcggaa atggcttacg aacggggcgg agatttcctg gaagatgcca ggaagatact   4680
taacagggaa gtgagagggc cgcggcaaag ccgttttcc ataggctccg ccccctgac     4740
aagcatcacg aaatctgacg ctcaaatcag tggtggcgaa acccgacagg actataaaga   4800
taccaggcgt ttccccctgg cggctccctc gtgcgctctc ctgttcctgc ctttcggttt   4860
accggtgtca ttccgctgtt atggccgcgt ttgtctcatt ccacgcctga cactcagttc   4920
cgggtaggca gttcgctcca agctggactg tatgcacgaa ccccccgttc agtccgaccg   4980
ctgcgcctta tccggtaact atcgtcttga gtccaacccg gaaagacatg caaaagcacc   5040
```

```
actggcagca gccactggta attgatttag aggagttagt cttgaagtca tgcgccggtt    5100
aaggctaaac tgaaaggaca agttttggtg actgcgctcc tccaagccag ttacctcggt    5160
tcaaagagtt ggtagctcag agaaccttcg aaaaaccgcc ctgcaaggcg ttttttcgt     5220 tttcagagca agagattacg cgcagaccaa aacgatctca agaagatcat cttattaatc    5280
agataaaata tttctagatt tcagtgcaat ttatctcttc aaatgtagca cctgaagtca    5340
gccccatacg atataagttg taattctcat gtttgacagc ttatcatcga taagctttaa    5400
tgcggtagtt tatcacagtt aaattattgc tgaagcggaa tccctggtta atgccgccgc    5460
cgatgccaat tgcattctcc aagtggggca cattgaacgc ttcaacccgg catttttaga    5520
gctaaccaaa attctcaaaa cggaagagtt attggcgatc gaagcccatc gcatgagtcc    5580
ctattcccag cgggccaatg atgtctccgt ggtattggat ttgatgatcc atgacattga    5640
cctgttgctg gaattggtgg gttcggaagt ggttaaactg tccgccagtg gcagtcgggc    5700
ttctgggtca ggatatttgg attatgtcac cgctacgtta ggcttctcct ccggcattgt    5760
ggccaccctc accgccagta aggtcaccca tcgtaaaatt cgttccatcg ccgcccactg    5820
caaaaattcc ctcaccgaag cggattttct caataacgaa attttgatcc atcgccaaac    5880
caccgctgat tggagcgcgg actatggcca ggtattgtat cgccaggatg gtctaatcga    5940
aaaggtttac accagtaata ttgaacctct ccacgctgaa ttagaacatt ttattcattg    6000
tgttagggga ggtgatcaac cctcagtggg gggagaacag gccctcaagg ccctgaagtt    6060
agccagttta attgaagaaa tggccctgga cagtcaggaa tggcatgggg gggaagttgt    6120
gacagaatat caagatgcca ccctggccct cagtgcgagt gtttaaatca acttaattaa    6180
tgcaattatt gcgagttcaa actcgataac tttgtgaaat attactgttg aattaatcta    6240
tgactattca atacaccccc ctagccgatc gcctgttggc ctacctcgcc gccgatcgcc    6300
taaatctcag cgccaagagt agttccctca acaccagtat tctgctcagc agtgacctat    6360
tcaatcagga aggggaatt gtaacagcca actatggctt tgatggttat atgg           6414
```

<210> SEQ ID NO 37
<211> LENGTH: 37
<212> TYPE: DNA
<213> ORGANISM: Artificial Sequence
<220> FEATURE:
<223> OTHER INFORMATION: Primer NB470

<400> SEQUENCE: 37
agagaatggt cccccatgtt cagctactga cggggtg                              37

<210> SEQ ID NO 38
<211> LENGTH: 56
<212> TYPE: DNA
<213> ORGANISM: Artificial Sequence
<220> FEATURE:
<223> OTHER INFORMATION: Primer NB471

<400> SEQUENCE: 38
ggattccgct tcagcaataa tttaactgtg ataaactacc gcattaaagc ttatcg         56

<210> SEQ ID NO 39
<211> LENGTH: 57
<212> TYPE: DNA
<213> ORGANISM: Artificial Sequence
<220> FEATURE:
<223> OTHER INFORMATION: Primer NB466

<400> SEQUENCE: 39

```
gggcgaattc cggaccacaa gataaaaata tatcatcatg aacaataaaa ctgtctg        57
```

<210> SEQ ID NO 40
<211> LENGTH: 34
<212> TYPE: DNA
<213> ORGANISM: Artificial Sequence
<220> FEATURE:
<223> OTHER INFORMATION: Primer NB467

<400> SEQUENCE: 40

```
ggtgccatcc ataccgggcc gccgtcccgt caag                                 34
```

<210> SEQ ID NO 41
<211> LENGTH: 989
<212> TYPE: DNA
<213> ORGANISM: Synechocystis PCC6803

<400> SEQUENCE: 41

```
attgctgaag cggaatccct ggttaatgcc gccgccgatg ccaattgcat tctccaagtg     60
gggcacattg aacgcttcaa cccggcattt ttagagctaa ccaaaattct caaaacggaa    120
gagttattgg cgatcgaagc ccatcgcatg agtccctatt cccagcgggc caatgatgtc    180
tccgtggtat tggatttgat gatccatgac attgacctgt tgctggaatt ggtgggttcg    240
gaagtggtta aactgtccgc cagtggcagt cgggcttctg ggtcaggata tttggattat    300
gtcaccgcta cgttaggctt ctcctccggc attgtggcca ccctcaccgc cagtaaggtc    360
acccatcgta aaattcgttc catcgccgcc cactgcaaaa attccctcac cgaagcggat    420
tttctcaata cgaaattttt gatccatcgc caaaccaccg ctgattggag cgcggactat    480
ggccaggtat tgtatcgcca ggatggtcta atcgaaaagg tttacaccag taatattgaa    540
cctctccacg ctgaattaga acattttatt cattgtgtta ggggaggtga tcaaccctca    600
gtgggggagag aacaggccct caaggccctg aagttagcca gtttaattga agaaatggcc    660
ctggacagtc aggaatggca tggggggggaa gttgtgacag aatatcaaga tgccaccctg    720
gccctcagtg cgagtgttta aatcaactta attaatgcaa ttattgcgag ttcaaactcg    780
ataactttgt gaaatattac tgttgaatta atctatgact attcaataca ccccctagc    840
cgatcgcctg ttggcctacc tcgccgccga tcgcctaaat ctcagcgcca agagtagttc    900
cctcaacacc agtattctgc tcagcagtga cctattcaat caggaagggg gaattgtaac    960
agccaactat ggctttgatg gttatatgg                                       989
```

<210> SEQ ID NO 42
<211> LENGTH: 989
<212> TYPE: DNA
<213> ORGANISM: Synechocystis PCC6803

<400> SEQUENCE: 42

```
ccggtatgga tggcaccgat gcggaatccc aacagattgc ctttgacaac aatgtggcct     60
ggaataacct gggggatttg tccaccacca cccaacgggc ctacacttcg gctattagca    120
cagacacagt gcagagtgtt tatggcgtta atctggaaaa aaacgataac attcccattg    180
ttttttgcgtg gccatttttt cccaccaccc ttaatcccac agattttcag gtaatgctta    240
acacggggga aattgtcacc ccggtgatcg cctctttgat tcccaacagt gaatacaacg    300
aacggcaaac ggtagtaatt acgggcaatt ttggtaatcg tttaaccccca ggcacggagg    360
gagcgattta tcccgtttcc gtaggcacag tgttggacag tactccttttg gaaatggtgg   420
```

```
gacccaacgg cccggtcagt gcggtgggta ttaccattga tagtctcaac ccctacgtgg      480
ccggcaatgg tcccaaaatt gtcgccgcta agttagaccg cttcagtgac ctggggggaag    540 gggctcccct ctggttagcc accaatcaaa ataacagtgg cggggattta tatggagacc     600
aagcccaatt tcgtttgcga atttacacca gcgccggttt ttcccccgat ggcattgcca     660
gtttactacc cacagaattt gaacggtatt ttcaactcca agcggaagat attacgggac     720
ggacagttat cctaacccaa actggtgttg attatgaaat tcccggcttt ggtctggtgc     780
aggtgttggg gctggcggat ttggccgggg ttcaggacag ctatgacctg acttacatcg     840
aagatcatga caactattac gacattatcc tcaaggggga cgaagccgca gttcgccaaa     900
ttaagagggt tgctttgccc tccgaagggg attattcggc ggtttataat cccggtggcc     960
ccggcaatga tccagagaat ggtcccccca                                      989

<210> SEQ ID NO 43
<211> LENGTH: 1089
<212> TYPE: DNA
<213> ORGANISM: Cuphea carthagenensis

<400> SEQUENCE: 43
atggcgaacg gtagcgctgt ctctctgaag agcggctcct tgaatacgca agaggacact      60
tcttcttccc caccgccacg cgcgttcatc aaccaattac ccgactggtc catgttattg     120
acggcgatta ccactgtctt tgttgccgca gagaaacagt ggactatgtt agaccgcaag     180
agcaagcgct ccgatatgtt agtggattct tttggcatgg aacgcattgt gcaggatggc     240
ttagtgtttc gtcaatcttt tagcattcgt tcttatgaaa tcggtgcaga tcgtcgtgca     300
tccattgaaa ccttaatgaa ccatctgcag gaaactagct tgaatcattg caaatccatt     360
cgcttgttga tgaggggttt tggtcgcacc cccgagatgt gcaaacgtga cttgatctgg     420
gtggttaccc gcatgcacat catggtcaac cgctacccta cctgggtgaa taccgttgag     480
attaacactt gggtttccca aagcggcaag aatggtatgg tcgtgattg gctgatttcc      540 gactgtaata ccggcgaaat cctgatccgc gcgacgtctg catgggcgat gatgaaccaa     600
aagacccgtc gtctgtctaa actgccttac gaagtcagcc aagagattgc tccgcacttc     660
gtcgacagcc ctcccgtgat cgaggacggc gaccgtaagt tacacaagtt cgatgtgaaa     720
accggcgaca gcatccgtaa aggttttgact ccgcgttgga tgacttaga tgttaatcag     780 cacgttaaca acgttaagta tatcggctgg atcttagaga gcatgccgac cgaggtcttg     840
gaaactcatg aactgtgttt cttaactctg gagtatcgtc gcgagtgcgg tcgcgatagc     900
gtgctggaat ctgtgaccgc gatggatcct tctaatgaag gtggtcgctc ccactaccag     960
catttactgc gcttggagga cggtactgac atcgttaagg gccgcactga gtggcgtcca    1020
aagaatgccc ggaatattgg tgccattagt accggtaaaa ccagtaatgg taatcccgcc    1080
agttaataa                                                            1089

<210> SEQ ID NO 44
<211> LENGTH: 361
<212> TYPE: PRT
<213> ORGANISM: Cuphea carthagenensis

<400> SEQUENCE: 44

Met Ala Asn Gly Ser Ala Val Ser Leu Lys Ser Gly Ser Leu Asn Thr
1               5                   10                  15

Gln Glu Asp Thr Ser Ser Ser Pro Pro Arg Ala Phe Ile Asn Gln
            20                  25                  30
```

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Ser
 50                  55                  60

Asp Met Leu Val Asp Ser Phe Gly Met Glu Arg Ile Val Gln Asp Gly
 65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
        115                 120                 125

Arg Thr Pro Glu Met Cys Lys Arg Asp Leu Ile Trp Val Val Thr Arg
130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
        195                 200                 205

Pro Tyr Glu Val Ser Gln Glu Ile Ala Pro His Phe Val Asp Ser Pro
210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Asn Val Lys Tyr Ile Gly Trp Ile Leu
            260                 265                 270

Glu Ser Met Pro Thr Glu Val Leu Glu Thr His Glu Leu Cys Phe Leu
        275                 280                 285

Thr Leu Glu Tyr Arg Arg Glu Cys Gly Arg Asp Ser Val Leu Glu Ser
290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
        355                 360

<210> SEQ ID NO 45
<211> LENGTH: 42
<212> TYPE: DNA
<213> ORGANISM: Artificial Sequence
<220> FEATURE:
<223> OTHER INFORMATION: Primer NB462

<400> SEQUENCE: 45
ctttgatggt tatatggcct gaggctgaaa tgagctgttg ac        42

<210> SEQ ID NO 46
<211> LENGTH: 47

```
<212> TYPE: DNA
<213> ORGANISM: Artificial Sequence
<220> FEATURE:
<223> OTHER INFORMATION: Primer NB463

<400> SEQUENCE: 46
gatctgaagc ttgaaaggtt attaactggc gggattacca ttactgg        47

<210> SEQ ID NO 47
<211> LENGTH: 47
<212> TYPE: DNA
<213> ORGANISM: Artificial Sequence
<220> FEATURE:
<223> OTHER INFORMATION: Primer NB464

<400> SEQUENCE: 47
gtaatcccgc cagttaataa cctttcaagc ttcagatcaa ttcgcgc        47

<210> SEQ ID NO 48
<211> LENGTH: 39
<212> TYPE: DNA
<213> ORGANISM: Artificial Sequence
<220> FEATURE:
<223> OTHER INFORMATION: Primer NB465

<400> SEQUENCE: 48
atatttttat cttgtggtcc ggaattcgcc cttctaagc                 39

<210> SEQ ID NO 49
<211> LENGTH: 57
<212> TYPE: DNA
<213> ORGANISM: Artificial Sequence
<220> FEATURE:
<223> OTHER INFORMATION: Primer NB466

<400> SEQUENCE: 49
gggcgaattc cggaccacaa gataaaaata tatcatcatg aacaataaaa ctgtctg    57

<210> SEQ ID NO 50
<211> LENGTH: 34
<212> TYPE: DNA
<213> ORGANISM: Artificial Sequence
<220> FEATURE:
<223> OTHER INFORMATION: Primer NB467

<400> SEQUENCE: 50
ggtgccatcc ataccgggcc gccgtcccgt caag                      34

<210> SEQ ID NO 51
<211> LENGTH: 6663
<212> TYPE: DNA
<213> ORGANISM: Artificial Sequence
<220> FEATURE:
<223> OTHER INFORMATION: pSGI-NB19 vector

<400> SEQUENCE: 51
cccccgtgct atgactagcg gcgatcgcca taccggccac gaccatttgc attggatccc    60
caacggcggc cacaacttcc atggcattga gatgcgggga atgatgttct agactctgac   120
gcaccaaagc caattttttgt tgatggttgc aatggggatg actactgttc actttgcccc   180
cagcgtcaat gcctagacct agcagtaccc ccagggctgt ggtagtgccc cccaccacgc   240
attcgcttag cactaagtaa ctttcggcat gttcctgggc taactgtgcg ccccactgca   300
aaccctgctg aaaaagatgc tccaccaggg ccaacggtaa cgcttgccct gtggaaagac   360
```

```
agcgggcggg ttgtccgtct agattgatga ctggcaccgc tgggggaatg ggtaaaccag    420
agttaaataa ataaaccgga gtatggaggg catccaccaa cgctttggtg atgaacactg    480
gggaaacccc agaaatgagg ggaggtaagg gataggttgc ccctgccgta gttcccttga    540
ttaaaaattc cgcatcggcg atcgccgtca attttcgatc agcggggggtt ttacccgccg    600
cagaaatgcc cggaattaaa ccagtttccg taaagcccaa cacacagaca aacaccggtg    660
gacagtggcc atggcgctca atccaggata aagcttggtc agactgggta taaactgtca    720
acatatttct gcaagagtgg gcccatgcac ccctatttgt ttattttttct aaatacattc    780
aaatatgtat ccgctcatga gacaataacc ctgataaatg cttcaataat acgaggagga    840
aaaaaaaatg cgctcacgca actggtccag aaccttgacc gaacgcagcg gtggtaacgg    900
cgcagtggcg gttttcatgg cttgttatga ctgttttttt gtacagtcta tgcctcgggc    960
atccaagcag caagcgcgtt acgccgtggg tcgatgtttg atgttatgga gcagcaacga   1020
tgttacgcag cagggcagtc gccctaaaac aaagttaggt ggctcaagta tgggcatcat   1080
tcgcacatgt aggctcggcc ctgaccaagt caaatccatg cgggctgctc ttgatctttt   1140
cggtcgtgag ttcggtgacg tagccaccta ctcccaacat cagccggact ccgattacct   1200
cgggaacttg ctccgtagta agacattcat cgcgcttgct gccttcgacc aagaagcggt   1260
tgttggcgct ctcgcggctt acgttctgcc caagtttgag cagccgcgta gtgagatcta   1320
tatctatgat ctcgcagtct ccggcgagca ccggaggcag ggcattgcca ccgcgctcat   1380
caatctcctc aagcatgagg ccaacgcgct tggtgcttat gtgatctacg tgcaagcaga   1440
ttacggtgac gatcccgcag tggctctcta tacaaagttg gcatacggg aagaagtgat    1500
gcactttgat atcgacccaa gtaccgccac ctaagcagag cttacgctga gcgcgcagat   1560
cagttggaag aatttgtcca ctacgtgaaa ggcgagatca ccaaggtagt cggcaaataa   1620
tgtctaacaa ttcgttcaag ccgacgccgc ttcgcggcgc ggcttaactc aagcgttaga   1680
tgcactaagc acataattgc tcacagccaa actatcaggt caagtctgct tttattattt   1740
ttaagcgtgc ataataagcc ctacacaaat tgggagatat atcatgaaag gctggctttt   1800
tcttgttatc gcaatagttg gcgaagtaat cgcaacatcc gcattaaaat ctagcgaggg   1860
ctttactaag ctgatccggt ggatgacctt ttgaatgacc tttaatagat tatattacta   1920
attaattggg gacccctagag gtccccttttt ttatttttaaa aattttttca caaaacggtt   1980
tacaagcata aagcttaggc cgtttaaacc aattgcggga agaaattaca gcttttgccg   2040
ctggcctaca gagtttagga gttaccccccc atcaacacct ggccatttttc gccgacaaca   2100
gccccccggtg gtttatcgcc gatcaaggca gtatgttggc tggagccgtc aacgccgtcc   2160
gttctgccca gcagagcgc caggaattac tctacatcct agaagacagc aacagccgta   2220
ctttaatcgc agaaaatcgg caaaccctaa gcaaattggc cctagatggc gaaaccattg   2280
acctgaaact aatcatcctc ctcaccgatg aagaagtggc agaggacagc gccattcccc   2340
aatataactt tgcccaggtc atggccctag ggccggcaa atccccact cccgttcccc   2400
gccaggaaga agatttagcc accctgatct acacctccgg caccacagga caacccaaag   2460
gggtgatgct cagccacggt aatttattgc accagtacg ggaattggat tcggtgatta   2520
ttccccgccc cggcgatcag gtgttgagca ttttgccctg ttggcactcc ctagaaagaa   2580
gcgccgaata ttttcttctt tcccggggct gcacgatgaa ctacaccagc attcgccatt   2640
tcaaggggga tgtgaaggac attaaacccc atcacattgt cggtgtgccc cggctgtggg   2700
aatccctcta cgaagggggta caaaaaacgt tccgagggcg aattctgcag atatccatca   2760
```

```
cactggcggc cgctcgagca tgcatctaga gggcccaatt cgccctatag tgagtcgtat    2820
tacaattcac tggccgtcgt tttacaacgt cgtgactggg aaaaccctgg cgttacccaa    2880
cttaatcgcc ttgcagcaca tccccctttc gccagctggc gtaatagcga agaggcccgc    2940
accgatcgcc cttcccaaca gttgcgcagc ctgaatggcg aatggacgcg ccctgtagcg    3000
gcgcattaag cgcggcgggt gtggtggtta cgcgcagcgt gaccgctaca cttgccagcg    3060
ccctagcgcc cgctcctttc gctttcttcc cttcctttct cgccacgttc gccggctttc    3120
cccgtcaagc tctaaatcgg ggctcccttt agggttccg atttagtgct ttacggcacc     3180
tcgaccccaa aaaacttgat tagggtgatg gttcacgtag tgggccatcg ccctgataga    3240 cggttttcg cccttttgacg ttggagtcca cgttctttaa tagtggactc ttgttccaaa    3300
ctggaacaac actcaaccct atctcggtct attcttttga tttataaggg attttgccga    3360
tttcggccta ttggttaaaa atgagctga tttaacaaaa atttaacgcg aattttaaca     3420
aaattcaggg cgcaagggct gctaaaggaa gcggaacacg tagaaagcca gtccgcagaa    3480
acggtgctga ccccggatga atgtcagcta ctgggctatc tggacaaggg aaaacgcaag    3540
cgcaaagaga aagcaggtag cttgcagtgg gcttacatgg cgatagctag actgggcggt    3600
tttatggaca gcaagcgaac cggaattgcc agctggggcg ccctctggta aggttgggaa    3660
gccctgcaaa gtaaactgga tggctttctt gccgccaagg atctgatggc gcaggggatc    3720
aagatctgat caagagacag gatgaggatc gtttcgcatg attgaacaag atggattgca    3780
cgcaggttct ccggccgctt gggtggagag gctattcggc tatgactggg cacaacagac    3840
aatcggctgc tctgatgccg ccgtgttccg gctgtcagcg caggggcgcc cggttctttt    3900
tgtcaagacc gacctgtccg gtgccctgaa tgaactgcag gacgaggcag cgcggctatc    3960
gtggctggcc acgacgggcg ttccttgcgc agctgtgctc gacgttgtca ctgaagcggg    4020
aagggactgg ctgctattgg gcgaagtgcc ggggcaggat ctcctgtcat cccaccttgc    4080
tcctgccgag aaagtatcca tcatggctga tgcaatgcgg cggctgcata cgcttgatcc    4140
ggctacctgc ccattcgacc accaagcgaa acatcgcatc gagcgagcac gtactcggat    4200
ggaagccggt cttgtcgatc aggatgatct ggacgaagag catcagggc tcgcgccagc      4260 cgaactgttc gccaggctca aggcgcgcat gcccgacggc gaggatctcg tcgtgaccca    4320
tggcgatgcc tgcttgccga atatcatggt ggaaaatggc cgcttttctg gattcatcga    4380
ctgtggccgg ctgggtgtgg cggaccgcta tcaggacata gcgttggcta cccgtgatat    4440
tgctgaagag cttggcggcg aatgggctga ccgcttcctc gtgctttacg gtatcgccgc    4500
tcccgattcg cagcgcatcg ccttctatcg ccttcttgac gagttcttct gaattgaaaa    4560
aggaagagta tgagtattca acatttccgt gtcgccctta ttcccttttt tgcggcattt    4620
tgccttcctg tttttgctca cccagaaacg ctggtgaaag taaaagatgc tgaagatcag    4680
ttgggtgcac gagtgggtta catcgaactg gatctcaaca gcggtaagat ccttgagagt    4740
tttcgccccg aagaacgttt tccaatgatg agcacttta aagttctgct atgtggcgcg     4800
gtattatccc gtattgacgc cgggcaagag caactcggtc gccgcataca ctattctcag    4860
aatgacttgg ttgagtactc accagtcaca gaaaagcatc ttacggatgg catgacagta    4920
agagaattat gcagtgctgc cataaccatg agtgataaca ctgcggccaa cttacttctg    4980
acaacgatcg gaggaccgaa ggagctaacc gcttttttgc acaacatggg gatcatgta     5040 actcgccttg atcgttggga accggagctg aatgaagcca taccaaacga cgagcgtgac    5100
```

```
accacgatgc ctgtagcaat ggcaacaacg ttgcgcaaac tattaactgg cgaactactt    5160
actctagctt cccggcaaca attaatagac tggatggagg cggataaagt tgcaggacca    5220
cttctgcgct cggcccttcc ggctggctgg tttattgctg ataaatctgg agccggtgag    5280
cgtgggtctc gcggtatcat tgcagcactg gggccagatg gtaagccctc ccgtatcgta    5340
gttatctaca cgacggggag tcaggcaact atggatgaac gaaatagaca gatcgctgag    5400
ataggtgcct cactgattaa gcattggtaa ctgtcagacc aagtttactc atatatactt    5460
tagattgatt taaaacttca tttttaattt aaaaggatct aggtgaagat cctttttgat    5520
aatctcatga ccaaaatccc ttaacgtgag ttttcgttcc actgagcgtc agacccgta     5580
gaaaagatca aggatcttc ttgagatcct ttttttctgc gcgtaatctg ctgcttgcaa     5640
acaaaaaaac caccgctacc agcggtggtt tgtttgccgg atcaagagct accaactctt    5700
tttccgaagg taactggctt cagcagagcg cagataccaa atactgttct tctagtgtag    5760
ccgtagttag gccaccactt caagaactct gtagcaccgc ctacatacct cgctctgcta    5820
atcctgttac cagtggctgc tgccagtggc gataagtcgt gtcttaccgg gttggactca    5880
agacgatagt taccggataa ggcgcagcgg tcgggctgaa cggggggttc gtgcacacag    5940
cccagcttgg agcgaacgac ctacaccgaa ctgagatacc tacagcgtga gctatgagaa    6000
agcgccacgc ttcccgaagg gagaaaggcg gacaggtatc cggtaagcgg cagggtcgga    6060
acaggagagc gcacgaggga gcttccaggg ggaaacgcct ggtatcttta tagtcctgtc    6120
gggtttcgcc acctctgact tgagcgtcga ttttgtgat gctcgtcagg ggggcggagc     6180
ctatggaaaa acgccagcaa cgcggccttt ttacggttcc tggccttttg ctggccttt     6240
gctcacatgt tctttcctgc gttatcccct gattctgtgg ataacgtat taccgccttt     6300
gagtgagctg ataccgctcg ccgcagccga acgaccgagc gcagcgagtc agtgagcgag    6360
gaagcggaag agcgcccaat acgcaaaccg cctctccccg cgcgttggcc gattcattaa    6420
tgcagctggc acgacaggtt cccgactgg aaagcgggca gtgagcgcaa cgcaattaat     6480
gtgagttagc tcactcatta ggcaccccag gctttacact ttatgcttcc ggctcgtatg    6540
ttgtgtggaa ttgtgagcgg ataacaattt cacacaggaa acagctatga ccatgattac    6600
gccaagcttg gtaccgagct cggatccact agtaacggcc gccagtgtgc tggaattcgc    6660
cct                                                                  6663

<210> SEQ ID NO 52
<211> LENGTH: 25
<212> TYPE: DNA
<213> ORGANISM: Artificial Sequence
<220> FEATURE:
<223> OTHER INFORMATION: Primer NB1

<400> SEQUENCE: 52
ctcgagcccc cgtgctatga ctagc                                          25

<210> SEQ ID NO 53
<211> LENGTH: 28
<212> TYPE: DNA
<213> ORGANISM: Artificial Sequence
<220> FEATURE:
<223> OTHER INFORMATION: Primer NB9

<400> SEQUENCE: 53
ctcgagcccg gaacgttttt tgtaccccc                                      28
```

```
<210> SEQ ID NO 54
<211> LENGTH: 362
<212> TYPE: PRT
<213> ORGANISM: Cuphea decandra

<400> SEQUENCE: 54

Met Gly Ile Asn Gly Ser Ser Val Gly Leu Lys Ser Gly Ser Leu Lys
1               5                   10                  15

Thr Gln Glu Asp Thr Pro Ser Ser Pro Pro Arg Thr Phe Ile Asn
            20                  25                  30

Gln Leu Pro Asp Trp Ser Met Leu Leu Ala Ala Ile Thr Thr Val Phe
                35                  40                  45

Leu Ala Ala Glu Lys Gln Trp Met Met Leu Asp Trp Lys Pro Lys Arg
        50                  55                  60

Pro Asp Met Leu Val Asp Pro Phe Gly Leu Gly Arg Ile Val Gln Asp
65                  70                  75                  80

Gly Leu Val Phe Arg Gln Asn Phe Ser Ile Arg Ser Tyr Glu Ile Gly
                85                  90                  95

Ala Asp Arg Thr Ala Ser Ile Glu Thr Leu Met Asn His Leu Gln Glu
            100                 105                 110

Thr Ala Leu Asn His Val Lys Ser Ala Gly Leu Leu Asn Asp Gly Phe
        115                 120                 125

Gly Arg Thr Pro Glu Met Tyr Lys Arg Asp Leu Ile Trp Val Val Ala
130                 135                 140

Lys Met Gln Val Met Val Asn Arg Tyr Pro Thr Trp Gly Asp Thr Val
145                 150                 155                 160

Glu Val Asn Thr Trp Val Ala Lys Ser Gly Lys Asn Gly Met Arg Arg
                165                 170                 175

Asp Trp Leu Ile Ser Asp Cys Asn Thr Gly Glu Ile Leu Thr Arg Ala
            180                 185                 190

Ser Ser Val Trp Val Met Met Asn Gln Lys Thr Arg Arg Leu Ser Lys
        195                 200                 205

Ile Pro Asp Glu Val Arg His Glu Ile Glu Pro His Phe Val Asp Ser
210                 215                 220

Pro Pro Val Ile Glu Asp Asp Arg Lys Leu Pro Lys Leu Asp Glu
225                 230                 235                 240

Lys Thr Ala Asp Ser Ile Arg Lys Gly Leu Thr Pro Arg Trp Asn Asp
                245                 250                 255

Leu Asp Val Asn Gln His Val Asn Asn Val Lys Tyr Ile Gly Trp Ile
            260                 265                 270

Leu Glu Ser Thr Pro Gln Glu Val Leu Glu Thr Gln Glu Leu Cys Ser
        275                 280                 285

Leu Thr Leu Glu Tyr Arg Arg Glu Cys Gly Arg Asp Ser Val Leu Glu
290                 295                 300

Ser Leu Thr Ala Val Asp His Ser Gly Lys Gly Ser Gly Ser Asn Phe
305                 310                 315                 320

Gln His Leu Leu Arg Leu Glu Asp Gly Gly Glu Ile Val Lys Gly Arg
                325                 330                 335

Thr Glu Trp Arg Pro Lys Asn Ala Val Ile Asn Gly Ala Val Ala Pro
            340                 345                 350

Gly Glu Thr Ser Pro Gly Asn Ser Val Ser
        355                 360

<210> SEQ ID NO 55
<211> LENGTH: 356
```

```
<212> TYPE: PRT
<213> ORGANISM: Cuphea paucipetela

<400> SEQUENCE: 55

Met Ala Asn Gly Ser Ala Val Ser Leu Lys Asp Gly Ser Leu Glu Thr
1               5                   10                  15

Gln Glu Gly Thr Ser Ser Ser His Pro Pro Arg Thr Phe Ile Asn
            20                  25                  30

Gln Leu Pro Asp Trp Ser Met Leu Leu Ser Ala Ile Thr Thr Val Phe
            35                  40                  45

Val Ala Ala Glu Lys Gln Trp Thr Met Leu Asp Arg Lys Ser Lys Arg
50                  55                  60

Pro Asp Met Leu Val Glu Pro Phe Val Gln Asp Gly Val Ser Phe Arg
65                  70                  75                  80

Gln Ser Phe Ser Ile Arg Ser Tyr Glu Ile Gly Ala Asp Arg Thr Ala
                85                  90                  95

Ser Ile Glu Thr Leu Met Asn Ile Phe Gln Glu Thr Ser Leu Asn His
            100                 105                 110

Cys Lys Ser Leu Gly Leu Leu Asn Asp Gly Phe Gly Arg Thr Pro Glu
        115                 120                 125

Met Cys Lys Arg Asp Leu Ile Trp Val Val Thr Lys Met Gln Ile Glu
    130                 135                 140

Val Asn Arg Tyr Pro Thr Trp Gly Asp Thr Ile Glu Val Thr Thr Trp
145                 150                 155                 160

Val Ser Glu Ser Gly Lys Asn Gly Met Ser Arg Asp Trp Leu Ile Ser
                165                 170                 175

Asp Cys His Thr Gly Glu Ile Leu Ile Arg Ala Thr Ser Val Trp Ala
            180                 185                 190

Met Met Asn Gln Lys Thr Arg Arg Leu Ser Lys Ile Pro Asp Glu Val
        195                 200                 205

Arg Gln Glu Ile Val Pro Tyr Phe Val Asp Ser Ala Pro Val Ile Glu
    210                 215                 220

Asp Asp Arg Lys Leu His Lys Leu Asp Val Lys Thr Gly Asp Ser Ile
225                 230                 235                 240

Arg Asn Gly Leu Thr Pro Arg Trp Asn Asp Leu Asp Val Asn Gln His
                245                 250                 255

Val Asn Asn Val Lys Tyr Ile Gly Trp Ile Leu Lys Ser Val Pro Thr
            260                 265                 270

Glu Val Phe Val Thr Gln Glu Leu Cys Gly Leu Thr Leu Glu Tyr Arg
        275                 280                 285

Arg Glu Cys Arg Arg Asp Ser Val Leu Glu Ser Val Thr Ala Met Asp
    290                 295                 300

Pro Ser Lys Glu Gly Asp Arg Ser Leu Tyr Gln His Leu Leu Arg Leu
305                 310                 315                 320

Glu Asn Gly Ala Asp Ile Ala Leu Gly Arg Thr Glu Trp Arg Pro Lys
                325                 330                 335

Asn Ala Gly Thr Asn Gly Ala Ile Ser Thr Thr Lys Thr Ser Pro Gly
            340                 345                 350

Asn Ser Val Ser
        355

<210> SEQ ID NO 56
<211> LENGTH: 267
<212> TYPE: PRT
<213> ORGANISM: Elaeis oleifera
```

<400> SEQUENCE: 56

| Asn | Ser | Ile | Pro | Asp | Trp | Ser | Met | Leu | Leu | Ala | Ala | Val | Thr | Thr | Ile |
|---|---|---|---|---|---|---|---|---|---|---|---|---|---|---|---|
| 1 | | | | 5 | | | | | 10 | | | | | 15 | |

Phe Leu Ala Ala Glu Lys Gln Trp Thr Leu Leu Asp Trp Lys Pro Arg
            20                  25                30

Arg Pro Asp Met Leu Thr Asp Ala Phe Ser Leu Gly Glu Ile Val Gln
        35                  40                45

Asp Gly Leu Val Phe Arg Gln Asn Phe Ser Ile Arg Ser Tyr Glu Ile
 50                  55                60

Gly Ala Asp Arg Thr Ala Ser Ile Glu Thr Leu Met Asn His Leu Gln
65              70                75                80

Glu Thr Val Leu Asn His Val Arg Asn Ala Gly Leu Leu Gly Asp Gly
            85                90              95

Phe Gly Ala Thr Pro Glu Met Ser Lys Arg Asn Leu Ile Trp Val Val
        100              105              110

Thr Lys Met Gln Val Leu Ile Glu His Tyr Pro Ser Trp Gly Asp Val
        115              120              125

Val Glu Val Asp Thr Trp Val Gly Ala Ser Gly Lys Asn Gly Met Arg
 130                 135              140

Arg Asp Trp His Val Arg Asp Tyr Arg Thr Gly Gln Thr Ile Pro Arg
145              150              155              160

Ala Thr Ser Ile Trp Val Met Met Asn Lys His Thr Arg Lys Leu Ser
            165              170              175

Lys Met Pro Glu Glu Val Arg Ala Glu Ile Gly Pro Tyr Phe Met Glu
        180              185              190

His Ala Thr Ile Val Asp Glu Asp Ser Gly Lys Leu Pro Lys Leu Asp
        195              200              205

Asp Asp Thr Ala Asp Tyr Ile Lys Trp Gly Leu Thr Pro Arg Trp Ser
 210                 215              220

Asp Leu Asp Val Asn Gln His Val Asn His Val Lys Tyr Ile Gly Trp
225              230              235              240

Ile Leu Glu Ser Ala Pro Ile Ser Ile Leu Glu Asn His Asn Trp Ala
            245              250              255

Ser Leu Ile Leu Asp Thr Gly Arg Asn Trp Asn
        260              265

<210> SEQ ID NO 57
<211> LENGTH: 417
<212> TYPE: PRT
<213> ORGANISM: Elaeis guineensis

<400> SEQUENCE: 57

Met Val Ala Ser Ile Val Ala Trp Ala Phe Phe Pro Thr Pro Ser Phe
1              5                  10              15

Ser Pro Thr Ala Ser Ala Lys Ala Ser Lys Thr Ile Gly Glu Gly Ser
            20                  25                30

Glu Asn Leu Asn Val Arg Gly Ile Ile Ala Lys Pro Thr Ser Ser Ser
        35                  40                45

Ala Ala Lys Gln Gly Lys Val Met Ala Gln Ala Val Pro Lys Ile Asn
 50                  55                60

Gly Ala Lys Val Gly Leu Lys Ala Glu Ser Gln Lys Ala Glu Glu Asp
65              70              75                80

Ala Ala Pro Ser Ser Ala Pro Arg Thr Phe Tyr Asn Gln Leu Pro Asp
            85                90              95

```
Trp Ser Val Leu Leu Ala Ala Val Thr Thr Ile Phe Leu Ala Ala Glu
            100                 105                 110

Lys Gln Trp Thr Leu Leu Asp Trp Lys Pro Arg Arg Pro Asp Met Leu
        115                 120                 125

Thr Gly Ala Phe Ser Leu Gly Lys Ile Val Gln Asp Gly Leu Val Phe
    130                 135                 140

Arg Gln Asn Phe Ser Ile Arg Ser Tyr Glu Ile Gly Ala Asp Arg Thr
145                 150                 155                 160

Ala Ser Ile Glu Thr Leu Met Asn His Leu Gln Glu Thr Ala Leu Asn
                165                 170                 175

His Val Arg Asn Ala Gly Leu Leu Gly Asp Gly Phe Gly Ala Thr Pro
            180                 185                 190

Glu Met Ser Lys Arg Asn Leu Ile Trp Val Val Thr Lys Met Gln Val
        195                 200                 205

Leu Ile Glu His Tyr Pro Ser Trp Gly Asp Val Val Glu Val Asp Thr
    210                 215                 220

Trp Val Gly Ala Ser Gly Lys Asn Gly Met Arg Arg Asp Trp His Val
225                 230                 235                 240

Arg Asp Tyr Arg Thr Gly Gln Thr Ile Leu Arg Ala Thr Ser Ile Trp
                245                 250                 255

Val Met Met Asp Lys His Thr Arg Lys Leu Ser Lys Met Pro Glu Glu
            260                 265                 270

Val Arg Ala Glu Ile Gly Pro Tyr Phe Met Glu His Ala Ala Ile Val
        275                 280                 285

Asp Glu Asp Ser Arg Lys Leu Pro Lys Leu Asp Asp Thr Ala Asp
    290                 295                 300

Tyr Ile Lys Trp Gly Leu Thr Pro Arg Trp Ser Asp Leu Asp Val Asn
305                 310                 315                 320

Gln His Val Asn Asn Val Lys Tyr Ile Gly Trp Ile Leu Glu Ser Ala
                325                 330                 335

Pro Ile Ser Ile Leu Glu Asn His Glu Leu Ala Ser Met Thr Leu Glu
            340                 345                 350

Tyr Arg Arg Glu Cys Gly Arg Asp Ser Val Leu Gln Ser Leu Thr Ala
        355                 360                 365

Val Ala Asn Asp Cys Thr Gly Gly Leu Pro Glu Ala Ser Ile Glu Cys
    370                 375                 380

Gln His Leu Leu Gln Leu Glu Cys Gly Ala Glu Ile Val Arg Gly Arg
385                 390                 395                 400

Thr Gln Trp Arg Pro Arg Arg Ala Ser Gly Pro Thr Ser Ala Gly Ser
                405                 410                 415

Ala

<210> SEQ ID NO 58
<211> LENGTH: 40
<212> TYPE: DNA
<213> ORGANISM: Artificial Sequence
<220> FEATURE:
<223> OTHER INFORMATION: Primer NB460

<400> SEQUENCE: 58
gtttatcaca gttaaattat tgctgaagcg gaatccctgg                          40

<210> SEQ ID NO 59
<211> LENGTH: 38
<212> TYPE: DNA
<213> ORGANISM: Artificial Sequence
```

```
<220> FEATURE:
<223> OTHER INFORMATION: Primer NB461

<400> SEQUENCE: 59
cagcctcagg ccatataacc atcaaagcca tagttggc                              38

<210> SEQ ID NO 60
<211> LENGTH: 32
<212> TYPE: DNA
<213> ORGANISM: Artificial Sequence
<220> FEATURE:
<223> OTHER INFORMATION: Primer NB468

<400> SEQUENCE: 60
gggacggcgg cccggtatgg atggcaccga tg                                    32

<210> SEQ ID NO 61
<211> LENGTH: 40
<212> TYPE: DNA
<213> ORGANISM: Artificial Sequence
<220> FEATURE:
<223> OTHER INFORMATION: Primer NB87

<400> SEQUENCE: 61
caattggcat gcacccctat ttgtttattt ttctaaatac                            40

<210> SEQ ID NO 62
<211> LENGTH: 47
<212> TYPE: DNA
<213> ORGANISM: Artificial Sequence
<220> FEATURE:
<223> OTHER INFORMATION: Primer NB88

<400> SEQUENCE: 62
caattggttt aaacggccta agctttatgc ttgtaaaccg ttttgtg                    47

<210> SEQ ID NO 63
<211> LENGTH: 35
<212> TYPE: DNA
<213> ORGANISM: Artificial Sequence
<220> FEATURE:
<223> OTHER INFORMATION: Primer NB5

<400> SEQUENCE: 63
gatcgacgta taaactgtca acatatttct gcaag                                 35
```